(12) United States Patent
Wen

(10) Patent No.: US 11,992,381 B2
(45) Date of Patent: *May 28, 2024

(54) ORTHODONTIC PLANNING SYSTEMS

(71) Applicant: uLab Systems, Inc., Redwood City, CA (US)

(72) Inventor: Huafeng Wen, Redwood Shores, CA (US)

(73) Assignee: uLab Systems, Inc., Memphis, TN (US)

( * ) Notice: Subject to any disclaimer, the term of this patent is extended or adjusted under 35 U.S.C. 154(b) by 348 days.

This patent is subject to a terminal disclaimer.

(21) Appl. No.: 16/735,983

(22) Filed: Jan. 7, 2020

(65) Prior Publication Data

US 2020/0146775 A1    May 14, 2020

Related U.S. Application Data

(63) Continuation of application No. 15/386,280, filed on Dec. 21, 2016, now Pat. No. 10,548,690, which is a continuation-in-part of application No. 15/230,193, filed on Aug. 5, 2016, now Pat. No. 10,335,250, and a continuation-in-part of application No. 15/230,139, filed on Aug. 5, 2016, now Pat. No. 10,624,717, and a continuation-in-part of application No. 15/230,170, filed on Aug. 5, 2016, now Pat. No. 11,583,365, and a continuation-in-part of application No. 15/230,216,
(Continued)

(51) Int. Cl.
*A61C 7/00* (2006.01)
*A61C 7/08* (2006.01)
*G16H 30/20* (2018.01)
*G16H 50/50* (2018.01)

(52) U.S. Cl.
CPC ............. *A61C 7/002* (2013.01); *A61C 7/08* (2013.01); *G16H 30/20* (2018.01); *G16H 50/50* (2018.01)

(58) Field of Classification Search
CPC .................................. A61C 7/002; A61C 7/08
See application file for complete search history.

(56) References Cited

U.S. PATENT DOCUMENTS 3,521,355 A    7/1970  Pearlman
4,068,379 A    1/1978  Miller et al.
(Continued)

FOREIGN PATENT DOCUMENTS

CA    2557573    7/2012
CN    1997324    7/2007
(Continued)

OTHER PUBLICATIONS

U.S. Appl. No. 15/230,139, filed Aug. 5, 2016.
(Continued)

*Primary Examiner* — Ralph A Lewis
(74) *Attorney, Agent, or Firm* — Levine Bagade Han LLP

(57) ABSTRACT

Systems and methods are disclosed for treating teeth to correct for malocclusions. This may be accomplished in one variation by receiving a scanned dental model of a subject's dentition, determining a treatment plan having a plurality of incremental movements for repositioning one or more teeth of the subject's dentition, and fabricating one or more aligners correlating to a first subset of the plurality of incremental movements.

22 Claims, 36 Drawing Sheets

Related U.S. Application Data filed on Aug. 5, 2016, now Pat. No. 10,631,953, and a continuation-in-part of application No. 15/230,251, filed on Aug. 5, 2016, now Pat. No. 10,357,336.

(60) Provisional application No. 62/238,514, filed on Oct. 7, 2015, provisional application No. 62/238,560, filed on Oct. 7, 2015, provisional application No. 62/238,554, filed on Oct. 7, 2015, provisional application No. 62/238,539, filed on Oct. 7, 2015, provisional application No. 62/238,532, filed on Oct. 7, 2015.

(56) References Cited

U.S. PATENT DOCUMENTS

| | | | |
|---|---|---|---|
| 4,597,739 | A | 7/1986 | Rosenberg |
| 4,889,485 | A | 12/1989 | Iida |
| 4,983,334 | A | 1/1991 | Adell |
| 5,055,039 | A | 10/1991 | Abbatte et al. |
| 5,186,623 | A | 2/1993 | Breads et al. |
| 5,259,762 | A | 11/1993 | Farrell |
| 5,506,607 | A | 4/1996 | Sanders et al. |
| 5,691,905 | A | 11/1997 | Dehoff et al. |
| 5,863,198 | A | 1/1999 | Doyle |
| 5,975,893 | A | 11/1999 | Chishti et al. |
| 6,120,287 | A | 9/2000 | Chen |
| 6,183,248 | B1 | 2/2001 | Chishti et al. |
| 6,210,162 | B1 | 4/2001 | Chishti et al. |
| 6,217,325 | B1 | 4/2001 | Chishti et al. |
| 6,227,850 | B1 | 5/2001 | Chishti et al. |
| 6,227,851 | B1 | 5/2001 | Chishti et al. |
| 6,250,918 | B1 | 6/2001 | Sachdeva et al. |
| 6,293,790 | B1 | 9/2001 | Hilliard |
| 6,299,440 | B1 | 10/2001 | Phan et al. |
| 6,309,215 | B1 | 10/2001 | Phan et al. |
| 6,315,553 | B1 | 11/2001 | Sachdeva et al. |
| 6,386,878 | B1 | 5/2002 | Pavlovskaia et al. |
| 6,390,812 | B1 | 5/2002 | Chishti et al. |
| 6,394,801 | B2 | 5/2002 | Chishti et al. |
| 6,398,548 | B1 | 6/2002 | Chishti et al. |
| 6,454,565 | B2 | 9/2002 | Phan et al. |
| 6,463,344 | B1 | 10/2002 | Pavloskaia |
| 6,471,511 | B1 | 10/2002 | Chishti et al. |
| 6,485,298 | B2 | 11/2002 | Chishti et al. |
| 6,488,499 | B1 | 12/2002 | Miller |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,582,227 | B2 | 6/2003 | Phan et al. |
| 6,602,070 | B2 | 8/2003 | Miller et al. |
| 6,607,382 | B1 | 8/2003 | Kuo et al. |
| 6,626,666 | B2 | 9/2003 | Chishti et al. |
| 6,629,840 | B2 | 10/2003 | Chishti et al. |
| 6,682,346 | B2 | 1/2004 | Chishti et al. |
| 6,688,885 | B1 | 2/2004 | Sachdeva |
| 6,699,037 | B2 | 3/2004 | Chishti et al. |
| 6,702,575 | B2 | 3/2004 | Hilliard |
| 6,705,861 | B2 | 3/2004 | Chishti et al. |
| 6,705,863 | B2 | 3/2004 | Phan et al. |
| 6,722,880 | B2 | 4/2004 | Chishti et al. |
| 6,729,876 | B2 | 5/2004 | Chishti et al. |
| 6,761,560 | B2 | 7/2004 | Miller |
| 6,783,360 | B2 | 8/2004 | Chishti |
| 6,786,721 | B2 | 9/2004 | Chishti et al. |
| 6,802,713 | B1 | 10/2004 | Chishti et al. |
| 6,830,450 | B2 | 12/2004 | Knopp et al. |
| 6,846,179 | B2 | 1/2005 | Chapouland et al. |
| 6,857,429 | B2 | 2/2005 | Eubank |
| 6,886,566 | B2 | 5/2005 | Eubank |
| 6,964,564 | B2 | 11/2005 | Phan et al. |
| 7,011,517 | B2 | 3/2006 | Nicozisis |
| 7,029,275 | B2 | 4/2006 | Rubbert et al. |
| 7,037,108 | B2 | 5/2006 | Chishti et al. |
| 7,040,896 | B2 | 5/2006 | Pavlovskaia et al. |
| 7,056,115 | B2 | 6/2006 | Phan et al. |
| 7,059,850 | B1 | 6/2006 | Phan et al. |
| 7,063,533 | B2 | 6/2006 | Phan et al. |
| 7,074,038 | B1 | 7/2006 | Miller |
| 7,077,647 | B2 | 7/2006 | Choi et al. |
| 7,092,784 | B1 | 8/2006 | Simkins |
| 7,104,790 | B2 | 9/2006 | Cronauer |
| 7,121,825 | B2 | 10/2006 | Chishti et al. |
| 7,125,248 | B2 | 10/2006 | Phan et al. |
| 7,134,874 | B2 | 11/2006 | Chishti et al. |
| 7,156,661 | B2 | 1/2007 | Choi et al. |
| 7,160,110 | B2 | 1/2007 | Imgrund et al. |
| 7,172,417 | B2 | 2/2007 | Sporbert et al. |
| 7,192,275 | B2 | 3/2007 | Miller |
| 7,220,122 | B2 | 5/2007 | Chishti |
| 7,320,592 | B2 | 1/2008 | Chishti et al. |
| 7,326,051 | B2 | 2/2008 | Miller |
| 7,331,783 | B2 | 2/2008 | Chishti et al. |
| 7,347,688 | B2 | 3/2008 | Kopelman et al. |
| 7,416,407 | B2 | 8/2008 | Cronauer |
| 7,434,582 | B2 | 10/2008 | Eubank |
| 7,435,083 | B2 | 10/2008 | Chishti et al. |
| 7,442,041 | B2 | 10/2008 | Imgrund et al. |
| 7,458,812 | B2 | 12/2008 | Sporbert et al. |
| 7,476,100 | B2 | 1/2009 | Kuo |
| 7,481,121 | B1 | 1/2009 | Cao |
| 7,553,157 | B2 | 6/2009 | Abolfathi et al. |
| 7,559,328 | B2 | 7/2009 | Eubank |
| 7,578,673 | B2 | 8/2009 | Wen et al. |
| 7,590,462 | B2 | 9/2009 | Rubbert et al. |
| 7,637,262 | B2 | 12/2009 | Bailey |
| 7,641,828 | B2 | 1/2010 | Desimone et al. |
| 7,658,610 | B2 | 2/2010 | Knopp |
| 7,689,398 | B2 | 3/2010 | Cheng et al. |
| 7,717,708 | B2 | 5/2010 | Sachdeva et al. |
| 7,771,195 | B2 | 8/2010 | Knopp et al. |
| 7,802,987 | B1 | 9/2010 | Phan et al. |
| 7,824,180 | B2 | 11/2010 | Abolfathi et al. |
| 7,826,646 | B2 | 11/2010 | Pavlovskaia et al. |
| 7,840,247 | B2 | 11/2010 | Liew et al. |
| 7,841,858 | B2 | 11/2010 | Knopp et al. |
| 7,845,938 | B2 | 12/2010 | Kim et al. |
| 7,854,609 | B2 | 12/2010 | Chen et al. |
| 7,878,801 | B2 | 2/2011 | Abolfathi et al. |
| 7,878,804 | B2 | 2/2011 | Korytov et al. |
| 7,878,805 | B2 | 2/2011 | Moss et al. |
| 7,883,334 | B2 | 2/2011 | Li et al. |
| 7,901,207 | B2 | 3/2011 | Knopp et al. |
| 7,905,724 | B2 | 3/2011 | Kuo et al. |
| 7,914,283 | B2 | 3/2011 | Kuo |
| 7,942,672 | B2 | 5/2011 | Kuo |
| 7,943,079 | B2 | 5/2011 | Desimone et al. |
| 7,957,824 | B2 | 6/2011 | Boronvinskih et al. |
| 7,987,099 | B2 | 7/2011 | Kuo et al. |
| 8,001,972 | B2 | 8/2011 | Eubank |
| 8,002,543 | B2 | 8/2011 | Kang et al. |
| 8,021,147 | B2 | 9/2011 | Sporbert et al. |
| 8,033,282 | B2 | 10/2011 | Eubank |
| 8,038,444 | B2 | 10/2011 | Kitching et al. |
| 8,070,487 | B2 | 12/2011 | Chishti et al. |
| 8,075,306 | B2 | 12/2011 | Kitching et al. |
| 8,099,268 | B2 | 1/2012 | Kitching et al. |
| 8,099,305 | B2 | 1/2012 | Kuo et al. |
| 8,105,080 | B2 | 1/2012 | Chishti et al. |
| 8,123,519 | B2 | 2/2012 | Schultz |
| 8,152,518 | B2 | 4/2012 | Kuo |
| 8,152,523 | B2 | 4/2012 | Sporbert et al. |
| 8,177,551 | B2 | 5/2012 | Sachdeva et al. |
| 8,235,713 | B2 | 8/2012 | Phan et al. |
| 8,272,866 | B2 | 9/2012 | Chun et al. |
| 8,275,180 | B2 | 9/2012 | Kuo et al. |
| 8,292,617 | B2 | 10/2012 | Brandt et al. |
| 8,303,302 | B2 | 11/2012 | Teasdale |
| 8,348,665 | B2 | 1/2013 | Kuo |
| 8,356,993 | B1 | 1/2013 | Marston |
| 8,401,686 | B2 | 3/2013 | Moss et al. |
| 8,401,826 | B2 | 3/2013 | Cheng et al. |
| 8,439,672 | B2 | 5/2013 | Matov et al. |
| 8,439,673 | B2 | 5/2013 | Korytov et al. |

(56) References Cited

U.S. PATENT DOCUMENTS

| | | |
|---|---|---|
| 8,444,412 B2 | 5/2013 | Baughman et al. |
| 8,465,280 B2 | 6/2013 | Sachdeva et al. |
| 8,469,705 B2 | 6/2013 | Sachdeva et al. |
| 8,469,706 B2 | 6/2013 | Kuo |
| 8,496,474 B2 | 7/2013 | Chishti et al. |
| 8,512,037 B2 | 8/2013 | Andreiko |
| 8,517,726 B2 | 8/2013 | Kakavand et al. |
| 8,535,580 B2 | 9/2013 | Puttler et al. |
| 8,562,337 B2 | 10/2013 | Kuo et al. |
| 8,562,338 B2 | 10/2013 | Kitching et al. |
| 8,562,340 B2 | 10/2013 | Chishti et al. |
| 8,636,509 B2 | 1/2014 | Miller |
| 8,636,510 B2 | 1/2014 | Kitching et al. |
| 8,690,568 B2 | 4/2014 | Chapoulaud et al. |
| 8,708,697 B2 | 4/2014 | Li et al. |
| 8,734,149 B2 | 5/2014 | Phan et al. |
| 8,734,150 B2 | 5/2014 | Chishti et al. |
| 8,738,165 B2 | 5/2014 | Cinader, Jr. et al. |
| 8,765,031 B2 | 7/2014 | Li et al. |
| 8,777,611 B2 | 7/2014 | Cios |
| 8,780,106 B2 | 7/2014 | Chishti et al. |
| 8,807,999 B2 | 8/2014 | Kuo et al. |
| 8,858,226 B2 | 10/2014 | Phan et al. |
| 8,864,493 B2 | 10/2014 | Leslie-Martin et al. |
| 8,899,976 B2 | 12/2014 | Chen et al. |
| 8,899,978 B2 | 12/2014 | Kitching et al. |
| 8,930,219 B2 | 1/2015 | Trosien et al. |
| 8,936,464 B2 | 1/2015 | Kopelman |
| 8,998,608 B2 | 1/2015 | Trosien et al. |
| 8,944,812 B2 | 2/2015 | Kuo et al. |
| 8,961,173 B2 | 2/2015 | Miller |
| 8,986,003 B2 | 3/2015 | Valoir |
| 8,992,215 B2 | 3/2015 | Chapoulaud et al. |
| 9,004,915 B2 | 4/2015 | Moss et al. |
| 9,022,781 B2 | 5/2015 | Kuo et al. |
| 9,026,238 B2 | 5/2015 | Kraemer et al. |
| 9,060,829 B2 | 6/2015 | Sterental et al. |
| 9,107,722 B2 | 8/2015 | Matov et al. |
| 9,119,691 B2 | 9/2015 | Namiranian et al. |
| 9,119,696 B2 | 9/2015 | Giordano et al. |
| 9,161,823 B2 | 10/2015 | Morton et al. |
| 9,161,824 B2 | 10/2015 | Chishti et al. |
| 9,204,942 B2 | 12/2015 | Phan et al. |
| 9,211,166 B2 | 12/2015 | Kuo et al. |
| 9,241,774 B2 | 1/2016 | Li et al. |
| 9,301,814 B2 | 4/2016 | Kaza et al. |
| 9,320,575 B2 | 4/2016 | Chishti et al. |
| 9,326,830 B2 | 5/2016 | Kitching et al. |
| 9,326,831 B2 | 5/2016 | Cheang |
| 9,333,052 B2 | 5/2016 | Miller |
| 9,345,557 B2 | 5/2016 | Anderson et al. |
| 9,351,809 B2 | 5/2016 | Phan et al. |
| 9,364,297 B2 | 6/2016 | Kitching et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,492,245 B2 | 11/2016 | Sherwood et al. |
| 9,820,829 B2 | 11/2017 | Kuo |
| 9,844,420 B2 | 12/2017 | Cheang |
| 9,917,868 B2 | 3/2018 | Ahmed |
| 9,922,170 B2 | 3/2018 | Trosien et al. |
| 10,011,050 B2 | 7/2018 | Kitching et al. |
| 10,022,204 B2 | 7/2018 | Cheang |
| 10,335,250 B2 | 7/2019 | Wen |
| 10,357,336 B2 | 7/2019 | Wen |
| 10,357,342 B2 | 7/2019 | Wen |
| 10,548,690 B2 * | 2/2020 | Wen ................. G16H 30/20 |
| 10,588,723 B2 | 3/2020 | Falkel |
| 10,624,717 B2 | 4/2020 | Wen |
| 10,631,953 B2 | 4/2020 | Wen |
| 10,881,486 B2 | 1/2021 | Wen |
| 10,925,698 B2 | 2/2021 | Falkel |
| 10,952,821 B2 | 3/2021 | Falkel |
| 11,051,913 B2 | 7/2021 | Wen |
| 11,096,763 B2 | 8/2021 | Akopov et al. |
| 11,207,161 B2 | 12/2021 | Brant |
| 11,348,257 B2 | 5/2022 | Lang |
| 11,364,098 B2 | 6/2022 | Falkel |
| 11,553,989 B2 | 1/2023 | Wen et al. |
| 11,583,365 B2 | 2/2023 | Wen |
| 11,638,628 B2 | 5/2023 | Wen |
| 11,663,383 B2 | 5/2023 | Cao |
| 11,707,180 B2 | 7/2023 | Falkel |
| 11,771,524 B2 | 10/2023 | Wen |
| 11,833,006 B2 | 12/2023 | Wen |
| 2001/0002310 A1 | 5/2001 | Chishti et al. |
| 2002/0009686 A1 | 1/2002 | Loc et al. |
| 2002/0010568 A1 | 1/2002 | Rubbert et al. |
| 2002/0025503 A1 | 2/2002 | Chapoulaud et al. |
| 2002/0042038 A1 | 4/2002 | Miller et al. |
| 2002/0051951 A1 | 5/2002 | Chishti et al. |
| 2002/0072027 A1 | 6/2002 | Chisti |
| 2002/0094503 A1 | 7/2002 | Chishti et al. |
| 2002/0110776 A1 | 8/2002 | Abels et al. |
| 2002/0150859 A1 | 11/2002 | Imgrund et al. |
| 2002/0177108 A1 | 11/2002 | Pavlovskaia et al. |
| 2003/0003416 A1 | 1/2003 | Chishti et al. |
| 2003/0008259 A1 | 1/2003 | Kuo et al. |
| 2003/0039940 A1 | 2/2003 | Miller |
| 2003/0059736 A1 | 3/2003 | Lai et al. |
| 2003/0190576 A1 | 10/2003 | Phan et al. |
| 2003/0207224 A1 | 11/2003 | Lotte |
| 2004/0023188 A1 | 2/2004 | Pavlovskaia et al. |
| 2004/0029068 A1 | 2/2004 | Sachdeva et al. |
| 2004/0038168 A1 | 2/2004 | Choi et al. |
| 2004/0134599 A1 | 7/2004 | Wang et al. |
| 2004/0142299 A1 | 7/2004 | Miller |
| 2004/0152036 A1 | 8/2004 | Abolfathi |
| 2004/0166456 A1 | 8/2004 | Chishti et al. |
| 2004/0166462 A1 | 8/2004 | Phan et al. |
| 2004/0166463 A1 | 8/2004 | Wen et al. |
| 2004/0197728 A1 | 10/2004 | Abolfathi et al. |
| 2004/0202983 A1 | 10/2004 | Tricca et al. |
| 2004/0219471 A1 | 11/2004 | Cleary et al. |
| 2004/0229183 A1 | 11/2004 | Knopp et al. |
| 2004/0242987 A1 | 12/2004 | Liew et al. |
| 2004/0253562 A1 | 12/2004 | Knopp |
| 2005/0010450 A1 | 1/2005 | Hultgren et al. |
| 2005/0019721 A1 | 1/2005 | Chishti |
| 2005/0048432 A1 | 3/2005 | Choi et al. |
| 2005/0095552 A1 | 5/2005 | Sporbert et al. |
| 2005/0095562 A1 | 5/2005 | Sporbert et al. |
| 2005/0118555 A1 | 6/2005 | Sporbert et al. |
| 2005/0153255 A1 | 7/2005 | Sporbert et al. |
| 2005/0192835 A1 | 9/2005 | Kuo et al. |
| 2005/0238967 A1 | 10/2005 | Rogers et al. |
| 2005/0241646 A1 | 11/2005 | Sotos et al. |
| 2005/0244781 A1 | 11/2005 | Abels et al. |
| 2005/0244782 A1 | 11/2005 | Chishti et al. |
| 2005/0271996 A1 | 12/2005 | Sporbert et al. |
| 2006/0003283 A1 | 1/2006 | Miller et al. |
| 2006/0035197 A1 | 2/2006 | Hishimoto |
| 2006/0068353 A1 | 3/2006 | Abolfathi et al. |
| 2006/0078840 A1 | 4/2006 | Robson |
| 2006/0078841 A1 | 4/2006 | Desimone et al. |
| 2006/0084030 A1 | 4/2006 | Phan et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0147872 A1 | 7/2006 | Andreiko |
| 2006/0177789 A1 | 8/2006 | O'Bryan |
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2006/0275736 A1 | 12/2006 | Wen et al. |
| 2007/0003907 A1 | 1/2007 | Chishti et al. |
| 2007/0238065 A1 | 10/2007 | Sherwood et al. |
| 2007/0264606 A1 | 11/2007 | Muha et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |

(56) References Cited

U.S. PATENT DOCUMENTS

| | | |
|---|---|---|
| 2008/0051650 A1 | 2/2008 | Massie et al. |
| 2008/0057461 A1 | 3/2008 | Cheng et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0115791 A1 | 5/2008 | Heine |
| 2008/0118882 A1 | 5/2008 | Su |
| 2008/0141534 A1 | 6/2008 | Hilliard |
| 2008/0182220 A1 | 7/2008 | Chishti et al. |
| 2008/0206702 A1 | 8/2008 | Hedge et al. |
| 2008/0215176 A1 | 9/2008 | Borovinskih et al. |
| 2008/0233528 A1 | 9/2008 | Kim et al. |
| 2008/0233530 A1 | 9/2008 | Cinader |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2008/0280247 A1 | 11/2008 | Sachdeva et al. |
| 2008/0305451 A1 | 12/2008 | Kitching et al. |
| 2008/0305453 A1 | 12/2008 | Kitching et al. |
| 2009/0081604 A1 | 3/2009 | Fisher |
| 2009/0117510 A1 | 5/2009 | Minium |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1 | 11/2009 | Kuo |
| 2009/0291408 A1 | 11/2009 | Stone-Collonge et al. |
| 2010/0036682 A1 | 2/2010 | Trosien et al. |
| 2010/0055635 A1 | 3/2010 | Kakavand |
| 2010/0086890 A1 | 4/2010 | Kuo |
| 2010/0138025 A1 | 6/2010 | Morton et al. |
| 2010/0167225 A1 | 7/2010 | Kuo |
| 2010/0173266 A1 | 7/2010 | Lu et al. |
| 2010/0179789 A1 | 7/2010 | Sachdeva et al. |
| 2010/0239992 A1 | 9/2010 | Brandt et al. |
| 2010/0280798 A1 | 11/2010 | Pattijn et al. |
| 2011/0005527 A1 | 1/2011 | Andrew et al. |
| 2011/0015591 A1 | 1/2011 | Hanson et al. |
| 2011/0020761 A1 | 1/2011 | Kalili |
| 2011/0039223 A1 | 2/2011 | Li |
| 2011/0091832 A1 | 4/2011 | Kim et al. |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0159451 A1 | 6/2011 | Kuo et al. |
| 2011/0165533 A1 | 7/2011 | Li et al. |
| 2011/0269092 A1 | 11/2011 | Kuo et al. |
| 2011/0269097 A1 | 11/2011 | Sporbert et al. |
| 2011/0270588 A1 | 11/2011 | Kuo et al. |
| 2011/0281229 A1 | 11/2011 | Abolfathi |
| 2012/0035901 A1 | 2/2012 | Kitching et al. |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0225401 A1 | 9/2012 | Kitching et al. |
| 2012/0227750 A1 | 9/2012 | Tucker |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0004634 A1 | 1/2013 | McCaskey et al. |
| 2013/0022255 A1 | 1/2013 | Chen et al. |
| 2013/0052625 A1 | 2/2013 | Wagner |
| 2013/0078593 A1 | 3/2013 | Andreiko |
| 2013/0081271 A1 | 4/2013 | Farzin-Nia et al. |
| 2013/0085018 A1 | 4/2013 | Jensen et al. |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1 | 8/2013 | Bailey et al. |
| 2013/0204583 A1 | 8/2013 | Matov et al. |
| 2013/0230819 A1 | 9/2013 | Arruda |
| 2013/0231899 A1 | 9/2013 | Khardekar et al. |
| 2013/0236848 A1 | 9/2013 | Arruda |
| 2013/0266906 A1 | 10/2013 | Soo |
| 2013/0302742 A1 | 11/2013 | Li et al. |
| 2013/0308846 A1 | 11/2013 | Chen et al. |
| 2013/0317800 A1 | 11/2013 | Wu et al. |
| 2013/0323665 A1 | 12/2013 | Dinh et al. |
| 2013/0325431 A1 | 12/2013 | See et al. |
| 2014/0023980 A1 | 1/2014 | Kitching et al. |
| 2014/0072926 A1 | 3/2014 | Valoir |
| 2014/0073212 A1 | 3/2014 | Lee |
| 2014/0076332 A1 | 3/2014 | Luco |
| 2014/0122027 A1 | 5/2014 | Andreiko et al. |
| 2014/0124968 A1 | 5/2014 | Kim |
| 2014/0167300 A1 | 6/2014 | Lee |
| 2014/0172375 A1 | 6/2014 | Grove |
| 2014/0178830 A1 | 6/2014 | Widu |
| 2014/0193765 A1 | 7/2014 | Kitching et al. |
| 2014/0193767 A1 | 7/2014 | Li et al. |
| 2014/0229878 A1 | 8/2014 | Wen et al. |
| 2014/0242532 A1 | 8/2014 | Arruda |
| 2014/0255864 A1 | 9/2014 | Machata et al. |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching |
| 2014/0315154 A1 | 10/2014 | Jung et al. |
| 2014/0067335 A1 | 11/2014 | Andreiko |
| 2014/0329194 A1 | 11/2014 | Sachdeva et al. |
| 2014/0349242 A1 | 11/2014 | Phan et al. |
| 2014/0358497 A1 | 12/2014 | Kuo et al. |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0025907 A1 | 1/2015 | Trosien et al. |
| 2015/0044623 A1 | 2/2015 | Rundlett |
| 2015/0044627 A1 | 2/2015 | German |
| 2015/0057983 A1 | 2/2015 | See et al. |
| 2015/0064641 A1 | 3/2015 | Gardner |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182303 A1 | 7/2015 | Abraham et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238280 A1 | 8/2015 | Wu et al. |
| 2015/0238282 A1 | 8/2015 | Kuo et al. |
| 2015/0238283 A1 | 8/2015 | Tanugula et al. |
| 2015/0238284 A1 | 8/2015 | Wu et al. |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0305831 A1 | 10/2015 | Cosse |
| 2015/0305919 A1 | 10/2015 | Stubbs et al. |
| 2015/0313687 A1 | 11/2015 | Blees et al. |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula et al. |
| 2015/0342464 A1 | 12/2015 | Wundrak et al. |
| 2015/0351870 A1 | 12/2015 | Mah |
| 2015/0351871 A1 | 12/2015 | Chishti et al. |
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |

(56) References Cited

U.S. PATENT DOCUMENTS

| | | |
|---|---|---|
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0074138 A1 | 3/2016 | Kitching et al. |
| 2016/0095668 A1 | 4/2016 | Kuo et al. |
| 2016/0095670 A1 | 4/2016 | Witte et al. |
| 2016/0106521 A1 | 4/2016 | Tanugula et al. |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135925 A1 | 5/2016 | Mason et al. |
| 2016/0135926 A1 | 5/2016 | Djamchidi |
| 2016/0135927 A1 | 5/2016 | Boltunov et al. |
| 2016/0157961 A1 | 6/2016 | Lee |
| 2016/0166363 A1 | 6/2016 | Varsano |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0199216 A1 | 7/2016 | Cam et al. |
| 2016/0203604 A1 | 7/2016 | Gupta et al. |
| 2016/0206402 A1 | 7/2016 | Kitching et al. |
| 2016/0220200 A1 | 8/2016 | Sanholm et al. |
| 2016/0228213 A1 | 8/2016 | Tod et al. |
| 2016/0256240 A1 | 9/2016 | Shivapuja et al. |
| 2016/0310235 A1 | 10/2016 | Derakhshan et al. |
| 2016/0338799 A1 | 11/2016 | Wu et al. |
| 2016/0367339 A1 | 12/2016 | Khardekar et al. |
| 2017/0007359 A1 | 1/2017 | Kopelman et al. |
| 2017/0065373 A1 | 3/2017 | Martz et al. |
| 2017/0079748 A1 | 3/2017 | Andreiko |
| 2017/0100207 A1 | 4/2017 | Wen |
| 2017/0100208 A1 | 4/2017 | Wen |
| 2017/0100209 A1 | 4/2017 | Wen |
| 2017/0100210 A1 | 4/2017 | Wen |
| 2017/0100211 A1 | 4/2017 | Wen |
| 2017/0100214 A1 | 4/2017 | Wen |
| 2017/0224444 A1 | 8/2017 | Viecilli et al. |
| 2017/0231721 A1 | 8/2017 | Akeel et al. |
| 2017/0325911 A1 | 11/2017 | Marshall |
| 2018/0014912 A1 | 1/2018 | Radmand |
| 2018/0028065 A1 | 2/2018 | Elbaz et al. |
| 2018/0042708 A1 | 2/2018 | Caron et al. |
| 2018/0055611 A1 | 3/2018 | Sun et al. |
| 2018/0078335 A1 | 3/2018 | Falkel |
| 2018/0078343 A1 | 3/2018 | Falkel |
| 2018/0078344 A1 | 3/2018 | Falkel |
| 2018/0078347 A1 | 3/2018 | Falkel |
| 2018/0092714 A1 | 4/2018 | Kitching et al. |
| 2018/0092715 A1 | 4/2018 | Kitching et al. |
| 2018/0125610 A1 | 5/2018 | Carrier, Jr. et al. |
| 2018/0158544 A1 | 6/2018 | Trosien et al. |
| 2018/0161126 A1 | 6/2018 | Marshall et al. |
| 2018/0168781 A1 | 6/2018 | Kopelman et al. |
| 2018/0174367 A1 | 6/2018 | Marom et al. |
| 2018/0333226 A1 | 11/2018 | Tsai et al. |
| 2018/0344431 A1 | 12/2018 | Kuo et al. |
| 2019/0008612 A1 | 1/2019 | Kitching et al. |
| 2019/0046297 A1 | 2/2019 | Kopelman et al. |
| 2019/0090987 A1 | 3/2019 | Hung |
| 2019/0231478 A1 | 8/2019 | Kopelman |
| 2019/0321135 A1 | 10/2019 | Wen |
| 2019/0343602 A1 | 11/2019 | Wen |
| 2019/0350680 A1 | 11/2019 | Chekh et al. |
| 2019/0358002 A1 | 11/2019 | Falkel |
| 2019/0388189 A1 | 12/2019 | Shivapuja et al. |
| 2020/0000552 A1 | 1/2020 | Mednikov et al. |
| 2020/0047868 A1 | 2/2020 | Young et al. |
| 2020/0081413 A1 | 3/2020 | Georg et al. |
| 2020/0105028 A1 | 4/2020 | Gao et al. |
| 2020/0170762 A1 | 6/2020 | Falkel |
| 2020/0205936 A1 | 7/2020 | Wen |
| 2020/0214801 A1 | 7/2020 | Wang et al. |
| 2020/0253693 A1 | 8/2020 | Wen |
| 2020/0316856 A1 | 10/2020 | Mojdeh et al. |
| 2020/0345459 A1 | 11/2020 | Schueller et al. |
| 2020/0357186 A1 | 11/2020 | Pokotilov et al. |
| 2020/0360120 A1 | 11/2020 | Inoue et al. |
| 2021/0106404 A1 | 4/2021 | Wen |
| 2021/0153981 A1 | 5/2021 | Falkel |
| 2021/0186668 A1 | 6/2021 | Falkel |
| 2021/0244518 A1 | 8/2021 | Ryu et al. |
| 2021/0282899 A1 | 9/2021 | Wen |
| 2021/0369417 A1 | 12/2021 | Wen et al. |
| 2021/0393376 A1 | 12/2021 | Wu et al. |
| 2022/0054232 A1 | 2/2022 | Wen et al. |
| 2022/0265395 A1 | 8/2022 | Falkel |
| 2022/0266577 A1 | 8/2022 | Sharma et al. |
| 2022/0409338 A1 | 12/2022 | Cao et al. |
| 2023/0053766 A1 | 2/2023 | Cao et al. |
| 2023/0058890 A1 | 2/2023 | Kenworthy |
| 2023/0233288 A1 | 7/2023 | Wen |
| 2023/0240808 A1 | 8/2023 | Schueller et al. |
| 2023/0320565 A1 | 10/2023 | Falkel |
| 2023/0380936 A1 | 11/2023 | Wen |
| 2023/0380938 A1 | 11/2023 | Sharma et al. |

FOREIGN PATENT DOCUMENTS

| | | |
|---|---|---|
| CN | 101427256 | 5/2009 |
| CN | 101636122 | 1/2010 |
| CN | 1973291 | 9/2010 |
| CN | 101528152 | 12/2012 |
| CN | 103932807 | 7/2014 |
| CN | 106580509 | 4/2017 |
| EP | 1474062 | 4/2011 |
| EP | 2056734 | 9/2015 |
| HK | 40004866 B | 8/2022 |
| JP | 2005-515826 | 6/2005 |
| JP | 2006-500999 | 1/2006 |
| JP | 2008-532563 | 8/2008 |
| JP | 2009-202031 | 9/2009 |
| JP | 4323322 | 9/2009 |
| JP | 2010-502246 | 1/2010 |
| JP | 2010-528748 | 8/2010 |
| JP | 4566746 | 10/2010 |
| JP | 2012-139540 | 7/2012 |
| JP | 5015197 | 8/2012 |
| JP | 5015765 | 8/2012 |
| JP | 5149898 | 2/2013 |
| JP | 2013-081785 | 5/2013 |
| JP | 5291218 | 9/2013 |
| JP | 2007-525289 | 9/2017 |
| JP | 2019-013463 | 1/2019 |
| JP | 2019-529042 | 10/2019 |
| JP | 2019-537033 | 12/2019 |
| KR | 2004-46323 | 10/2009 |
| KR | 10-1450866 | 10/2014 |
| KR | 2018-0090481 | 8/2018 |
| WO | WO 2001/082192 | 11/2001 |
| WO | WO 2002/047571 | 6/2002 |
| WO | WO 2003/063721 | 8/2003 |
| WO | WO 2004/028391 | 4/2004 |
| WO | WO 2005/086058 | 9/2005 |
| WO | WO 2004/098379 | 11/2005 |
| WO | WO 2006/050452 | 5/2006 |
| WO | WO 2006/096558 | 9/2006 |
| WO | WO 2008/026064 | 3/2008 |
| WO | WO 2008/118546 | 10/2008 |
| WO | WO 2008/149222 | 12/2008 |
| WO | WO 2009/057937 | 5/2009 |
| WO | WO 2009/068892 | 6/2009 |
| WO | WO 2016/004415 | 1/2016 |
| WO | WO 2017/062207 | 4/2017 |
| WO | WO 2017/062208 | 4/2017 |
| WO | WO 2017/062209 | 4/2017 |
| WO | WO 2017/062210 | 4/2017 |
| WO | WO 2018/057622 | 3/2018 |
| WO | WO 2018/112273 | 6/2018 |
| WO | WO 2018/118200 | 6/2018 |
| WO | WO 2021/105878 | 6/2021 |

(56) References Cited

FOREIGN PATENT DOCUMENTS

| WO | WO 2021/247145 | 12/2021 |
| WO | WO 2021/247950 | 12/2021 |
| WO | WO 2022/040671 | 2/2022 |
| WO | WO 2022/178514 | 8/2022 |
| WO | WO 2023/023417 | 2/2023 |
| WO | WO 2023/023418 | 2/2023 |
| WO | WO 2023/230460 | 11/2023 |

OTHER PUBLICATIONS

U.S. Appl. No. 15/230,170, filed Aug. 5, 2016.
U.S. Appl. No. 15/230,193, filed Aug. 5, 2016.
U.S. Appl. No. 15/230,216, filed Aug. 5, 2016.
U.S. Appl. No. 15/230,251, filed Aug. 5, 2016.
U.S. Appl. No. 15/386,280, filed Dec. 21, 2016.
U.S. Appl. No. 15/710,469, filed Sep. 20, 2017.
U.S. Appl. No. 15/710,604, filed Sep. 20, 2017.
U.S. Appl. No. 15/710,666, filed Sep. 20, 2017.
U.S. Appl. No. 15/710,703, filed Sep. 20, 2017.
U.S. Appl. No. 16/410,368, filed May 13, 2019.
U.S. Appl. No. 16/423,840, filed May 28, 2019.
U.S. Appl. No. 16/435,028, filed Jun. 7, 2019.
U.S. Appl. No. 16/657,639, filed Oct. 18, 2019.
U.S. Appl. No. 16/735,983, filed Jan. 7, 2020.
U.S. Appl. No. 16/783,055, filed Feb. 5, 2020.
U.S. Appl. No. 16/799,046, filed Feb. 24, 2020.
U.S. Appl. No. 16/803,184, filed Feb. 27, 2020.
U.S. Appl. No. 17/130,384, filed Dec. 22, 2020.
U.S. Appl. No. 17/162,748, filed Jan. 29, 2021.
U.S. Appl. No. 17/176,835, filed Feb. 16, 2021.
U.S. Appl. No. 17/228,406, filed Apr. 12, 2021.
U.S. Appl. No. 17/337,157, filed Jun. 2, 2021.
U.S. Appl. No. 17/404,894, filed Aug. 17, 2021.
U.S. Appl. No. 17/462,198, filed Aug. 31, 2021.
U.S. Appl. No. 17/651,382, filed Feb. 16, 2022.
U.S. Appl. No. 17/658,183, filed Apr. 6, 2022.
U.S. Appl. No. 17/662,819, filed May 10, 2022.
U.S. Appl. No. 17/664,777, filed May 24, 2022.
U.S. Appl. No. 17/664,854, filed May 24, 2022.
Kovach, I. V. et al., "Clinic, diagnosis, treatment, prevention, prosthetics various dentofacial anomalies and deformities," DMA, 2018.

\* cited by examiner

ORTHODONTIC PLANNING SYSTEMS

CROSS-REFERENCE TO RELATED APPLICATIONS

This application is a continuation of U.S. patent application Ser. No. 15/386,280 filed Dec. 21, 2016 (now U.S. Pat. No. 10,548,690), which is a continuation-in-part of U.S. patent application Ser. No. 15/230,139 filed Aug. 5, 2016 (now U.S. Pat. No. 10,624,717), which claims the benefit of priority to U.S. Prov. App. 62/238,554 filed Oct. 7, 2015; a continuation-in-part of U.S. patent application Ser. No. 15/230,170 filed Aug. 5, 2016, which claims the benefit of priority to U.S. Prov. App. 62/238,560 filed Oct. 7, 2015; a continuation-in-part of U.S. patent application Ser. No. 15/230,193 filed Aug. 5, 2016 (now U.S. Pat. No. 10,335,250), which claims the benefit of priority to U.S. Prov. App. 62/238,532 filed Oct. 7, 2015; a continuation-in-part of U.S. patent application Ser. No. 15/230,216 filed Aug. 5, 2016 (now U.S. Pat. No. 10,631,953), which claims the benefit of priority to U.S. Prov. App. 62/238,514 filed Oct. 7, 2015; and a continuation-in-part of U.S. patent application Ser. No. 15/230,251 filed Aug. 5, 2016 (now U.S. Pat. No. 10,357,336), which claims the benefit of priority to U.S. Prov. App. 62/238,539 filed Oct. 7, 2015. Each of these applications is incorporated herein by reference in its entirety.

FIELD OF THE INVENTION

The present invention relates to methods and apparatus for computerized orthodontics. More particularly, the present invention relates to methods and apparatus for planning orthodontic treatments and fabricating one or more dental appliances such as retainers and aligners using three-dimensional (3D) printing processes.

BACKGROUND OF THE INVENTION

Orthodontics is a specialty of dentistry that is concerned with the study and treatment of malocclusions which can result from tooth irregularities, disproportionate facial skeleton relationships, or both. Orthodontics treats malocclusion through the displacement of teeth via bony remodeling and control and modification of facial growth.

This process has been traditionally accomplished by using static mechanical force to induce bone remodeling, thereby enabling teeth to move. In this approach, braces having an archwire interface with brackets are affixed to each tooth. As the teeth respond to the pressure applied via the archwire by shifting their positions, the wires are again tightened to apply additional pressure. This widely accepted approach to treating malocclusions takes about twenty-four months on average to complete, and is used to treat a number of different classifications of clinical malocclusion. Treatment with braces is complicated by the fact that it is uncomfortable and/or painful for patients, and the orthodontic appliances are perceived as unaesthetic, all of which creates considerable resistance to use. Further, the treatment time cannot be shortened by increasing the force, because too high a force results in root resorption, as well as being more painful. The average treatment time of twenty-four months is very long, and further reduces usage. In fact, some estimates provide that less than half of the patients who could benefit from such treatment elect to pursue orthodontics.

Kesling introduced the tooth positioning appliance in 1945 as a method of refining the final stage of orthodontic finishing after removal of the braces (debanding). The positioner was a one-piece pliable rubber appliance fabricated on the idealized wax set-ups for patients whose basic treatment was complete. Kesling also predicted that certain major tooth movements could also be accomplished with a series of positioners fabricated from sequential tooth movements on the set-up as the treatment progressed. However, this idea did not become practical until the advent of three-dimensional (3D) scanning and use of computers by companies including Align Technologies and as well as OrthoClear, ClearAligner, and ClearCorrect to provide greatly improved aesthetics since the devices are transparent.

However for traditional trim model to individual tooth, the gum geometry is lost and the fake gum is recreated, often remodeled by a technician. Hence, the gum geometry may not be accurate at first and an animation of gum changes over time due to lack of a physical model is even harder to model. Such inaccurate modeling causes the resulting aligner to be mismatched resulting in devices which are too large or too small resulting in patient discomfort.

Another problem is that without the real gum as the reference, some so-called modeled treatments cannot be achieved in reality resulting in potential errors, e.g., a tooth movement can occur within a mis-modeled gingival, however, the tooth movement may actually be moved exteriorly of a patient's real gingival.

Another problem of trimming and hole filling and creating an individual tooth and gum model is there is little information that can define the real boundary of two teeth. Such trim and fill models force the boundary surfaces to be defined even if they are arbitrary.

Depending on what boundary surface is defined, the movement can be restricted or relax, meaning some real life movement can be achieved; however, due to such inaccuracies, the modeling software is unable to model accurately due to models colliding into each other. This may cause the real treatment outcome to create gaps between teeth and further requiring final refinements which increase cost and patient dissatisfaction. On the other hand, if the modeled movement is relax, the software may enable movements which are physically impossible in reality and this may cause the modeled device to push teeth into one another unable to move. This may also cause the plastic shell of the aligner to sometimes stretch so much that the shell applies an uncomfortable amount of force, which could be painful, to a patient.

Another problem of trim and hole fill is the filling of the geometry like a real tooth, for below, the below lines are likely of boundary surfaces modeled, such models look like a real tooth; however, such sharp boundaries cause deeper undercuts which, once printed and thermal formed to have a plastic shell, make removal of the plastic shell from the printed model difficult due to the deep undercuts. To compensate for this, a bevel object is typcially created to fill the clevis increasing inaccuracy and costs.

Another problem of trim and hole filling is the model size is too large to communicate between the user and manufacturer thus requiring that the model size be reduced resulting in missing model details. These inaccuracies could misguide professionals, e.g., the full complex model may not show a gap between two adjacent teeth however the reduced model may show one.

These 3D scanning and computerized planning treatments are cumbersome and time consuming. Accordingly, there exists a need for an efficient and cost effective procedure for planning the orthodontic treatment of a patient.

SUMMARY OF THE INVENTION

In treating a patient to correct for one or more conditions with their dentition, the steps of digitally scanning the patient's dentition, planning the treatment, and/or optionally fabricating the treatment devices, such as aligners to correct positioning of one or more teeth, may be performed directly at the provider's office.

One method for treating a subject, as described herein, may generally comprise receiving a scanned dental model of a subject's dentition, determining a treatment plan having a plurality of incremental movements for repositioning one or more teeth of the subject's dentition, and fabricating one or more aligners correlating to a first subset of the plurality of incremental movements.

In one variation, this may further comprise reassessing the subject's dentition after a predetermined period of time to monitor the repositioning of the one or more teeth.

In another variation, this may further comprise fabricating one or more additional aligners correlating to a second subset of the plurality of incremental movements.

In another variation, this may further comprise treating the one or more teeth via a non-aligner corrective measure.

In another variation, this may further comprise receiving an input from the subject relating to the treatment plan.

In another variation, determining the treatment plan may further comprise applying a label to one or more teeth within the dental model, simulating a rolling ball process along an exterior of the one or more teeth and gums within the dental model, determining a boundary between each of the one or more teeth and gums based on a path or trajectory of the rolling ball process, assigning a hard or soft region to each of the one or more teeth and gums within the dental model, and moving a position of the one or more teeth within the dental model to correct for malocclusions in developing a treatment plan.

In another variation, determining the treatment plan may further comprise determining a movement for a plurality of digital tooth models in the dental model for correcting the malocclusions via a tooth movement manager module, assigning a sphere of influence on each of the tooth models to set a proximity distance between each tooth model via a collision manager module, monitoring an actual state of each each tooth of the subject, comparing the actual state of each tooth against an expected state of each tooth model via a tooth manager module, and adjusting the movement of one or more teeth based on a comparison of the actual state and the expected state if a deviation is detected.

In another variation, fabricating one or more aligners may further comprise generating a free-form structure having a lattice structure which matches at least part of a surface of the dentition, wherein the lattice structure defines a plurality of open spaces such that the free-form structure is at least partially transparent, and manufacturing the lattice structure by impregnating or covering a coating into or upon the lattice structure such that the oral appliance is formed.

In another variation, fabricating one or more aligners may further comprise fabricating a support structure which corresponds to an outer surface of the dentition, forming one or more oral appliances upon an exterior surface of the support structure such that an interior of the one or more oral appliances conform to the dentition, and removing the support structure from the interior of the one or more oral appliances.

In another variation, fabricating one or more aligners may further comprise calculating a rule-based cutting loop path on the model for determining a path for trimming a mold replicating the patient's dentition, applying a drape wall from the cutting loop on the model to reduce a complexity of the model, determining a position of a cutting instrument relative to the mold for trimming the mold, generating a computer numerical control code based on the drape wall and position of the cutting instrument, and fabricating the mold based on the generated computer numerical control code.

Systems and methods are disclosed for treating teeth to correct for malocclusions. This may be accomplished by applying a series of labels to a digital dental model and applying a rolling ball process to identify tooth boundaries separating one tooth from a neighboring tooth. The rolling ball process may also be used to determine the crown/gum margin. The user may further assign regions to the dental model to indicate hard regions (hard regions have a criteria where they cannot change their shape) and soft regions (soft regions have a criteria where they can deform with an attached hard region). With the dental model labeled and defined, the user may then generate a treatment plan for moving the labeled and defined tooth or teeth relative to one another to correct for any malocclusions. Upon approval of the treatment plan, a series of 3D printed dental appliances or aligners to be worn in series by the patient may be fabricated to ultimately move the tooth or teeth to a desired position.

One method for planning a treatment for correcting malocclusions may generally comprise receiving a scanned dental model of a subject's dentition and then applying a label to one or more teeth within the dental model. The rolling ball process may be simulated along an exterior of the one or more teeth and gums within the dental model for determining a boundary between each of the one or more teeth and gums based on a path or trajectory of the rolling ball process. The hard or soft regions may be assigned to each of the one or more teeth and gums within the dental model and a position of the one or more teeth within the dental model may be moved by the user to correct for malocclusions in developing a treatment plan. Once approved (e.g., by the patient and/or user), one or more prostheses or aligners may be fabricated to move the one or more teeth according to the treatment plan.

Moving a position of the one or more teeth in developing the treatment plan generally comprises morphing a new dental model from the dental model. As described, the one or more prostheses or aligners may be fabricated, e.g., via 3D printing the one or more aligners, so that the entire process of may be accomplished in a single visit by the subject to a dental office.

In another example for planning a treatment for correcting malocclusions, the method may generally comprise directly scanning a subject's dentition to create a digitized dental model and having the user apply a label to one or more teeth within the dental model. The simulated ball may be rolled digitally along an exterior of the one or more teeth and gums within the dental model for determining a boundary between each of the one or more teeth and gums based on a path or trajectory of the rolling ball process. The hard region may be assigned to each of the one or more teeth and a soft region may be similarly assigned to gums within the dental model. Then a position of the one or more teeth may be moved within the dental model to correct for malocclusions in developing a treatment plan.

As described, once the treatment plan has been approved (e.g., by the patient and/or user), one or more prostheses or aligners may be fabricated to move the one or more teeth according to the treatment plan and the entire process of may be accomplished in a single visit by the subject to a dental office.

Advantages of the system may include one or more of the following. The system allows close control by the treating professional at each stage by allowing specific movements from one stage to the next stage. In one example, it is desirable in some settings to synchronize the movement and operation of the individual tooth models to have a few tooth models operate in a choreographed manner as dictated by a treating professional. Having this choreographed movement is not typically possible through manual control where the tooth models move randomly and independently. The present control method and/or system are ideal for use in moving a number of tooth models and to provide synchronized tooth movement. Such a method may be non-swarming to avoid any collisions between the teeth and to also avoid the appearance of merely random movements, at least in some applications. Rather, it is desirable for the tooth models to each react safely to environmental conditions such as changes in bone structure and soft tissue during group tooth movement of choreographed tooth models.

The system is also provided for controlling tooth movement of a plurality of biological objects (tooth models). The system includes a plurality of tooth models each including computer code controlling its movement. The system also includes a tooth movement control system (TMCS) with a processor executing a dental manager module and with memory scoring a different tooth movement plan for each of the tooth models. In practice, the tooth movement plans are stored in the memory of each of the tooth models (e.g., a different tooth movement plan for each tooth model). Then, during tooth movement operation, each of the local control modules independently controls the tooth model to execute the tooth movement plan stored in the memory of the tooth model.

In some cases, the local control module of each of the tooth models operates to periodically compare a present position of the tooth model with the tooth movement plan and, based on the comparing, modifying control of the tooth model. In these cases, modifying of the control may include altering a tooth movement speed or selecting a new way point for the tooth model in the tooth movement plan as a target. In other cases, the local control of each of the tooth models may operate to detect another one of the tooth models within a safety envelope about the tooth model and, in response, communicate a collision warning message to the detected one of the tooth models to cause the detected one of the tooth models to alter its course to move out of the safety envelope. In some specific implementations, the tooth models are teeth, and the local control module of each of the tooth models operates to detect pitch and roll of the tooth and, when the pitch or the roll exceeds a predefined maximum, switches operations of the tooth to a safe operating mode.

The description also teaches a tooth movement control method. In this control method, an initial step may be to receive a tooth movement plan unique to each of the teeth for a plurality of teeth. A next step may involve concurrently operating the teeth to execute the tooth movement plans. The method further includes providing a communications channel between pairs of the teeth with a first one of the teeth detecting a second one of the teeth in a predefined space proximal to the first one of the teeth. The method also includes, with the first one of the teeth, transmitting a message to the second tooth over the communication channel between the first and second teeth causing the second tooth to change position to avoid collision.

In some implementations of the method, the tooth movement plans may include a plurality of way points for each of the teeth. In such implementations, the method may further include, during the operating of the teeth to execute the tooth movement plans, adjusting tooth movement speed or course of one of the teeth based on comparison of a present position and one of the way points. The tooth movement plans may further include an elapsed time period for each of the way points, and then, the adjusting of the tooth movement speed or course may be performed when the elapsed time is exceeded by the one of the teeth.

In some implementations of the method, the teeth movements are decomposed to different movement metrics, e.g. a tooth movement can be decomposed to tip, rotation around long axis, bodily movement, etc. The artificial intelligence network, usually a neural network is built, such network having different neurons and weights can be adjusted, where treated cases are the learning set of such neural network. By inputting each case and adjusting the network weights to make the network more predictable to the treatment outcome, when a new case comes, the designed movement may be run through the network and an ideal and more predictable movement design is achieved. The more training cases are provided, the more robust network can be achieved.

In one embodiment, each tooth executes rules that as a group conforms to one or more of the following goals or objectives:

1. Adherence to Andrews' Six Keys To Occlusion;
2. Root cannot move more than 0.5 mm per month;
3. Conform to a U or V formation;
4. Open the bite;
5. No interproximal reduction;
6. Avoid moving any implant tooth;
7. Define sub-group of teeth that move together as a unit.

The system allows close control by the treating professional at each stage by allowing specific movements from one stage to the next stage. In one example, it is desirable in some settings to synchronize the movement and operation of the tooth models to have tooth models operate in a choreographed manner as dictated by a treating professional, which is not possible through manual control where the tooth models move randomly and independently.

The present control method and/or system may be ideal for use in moving a number of tooth models and to provide synchronized tooth movement. Such a method would be non-swarming since it is desirable to avoid collisions and to also avoid the appearance of merely random movement (at least in some applications) of the tooth models. Rather, it is desirable for the tooth models to each react safely to environmental conditions such as changes in bone structure and soft tissue during group tooth movement of choreographed tooth models.

Turning now to fabricating free-form structures including oral appliances or aligners, one method for fabricating an oral appliance may generally comprise capturing a three-dimensional representation of a dentition of a subject and generating a free-form structure having a lattice structure which matches at least part of a surface of the dentition, wherein the lattice structure defines a plurality of open spaces such that the free-form structure is at least partially transparent. The lattice structure may then be manufactured by impregnating or covering a coating into or upon the lattice structure such that the oral appliance is formed.

One or more oral appliances may thus be manufactured where each subsequent oral appliance is configured to impart a movement of one or more teeth of the subject and is intended to be worn by the subject to correct for any malocclusions.

Generally, the oral appliance may comprise the lattice structure which is configured to match at least part of a surface of a dentition of the subject, wherein the lattice structure defines a plurality of open spaces such that the free-form structure is at least partially transparent. A coating may impregnate or cover into or upon the lattice structure and at least one dental attachment structure may be formed as part of the lattice structure, wherein the dental attachment structure is located in proximity to one or more teeth to be moved.

The system provides free-form structures fitting the surface of a body part, which are at least partially made by additive manufacturing. The free-form structures may comprise a basic structure which includes a lattice structure and a coating material provided thereon. The lattice structure may be impregnated in and/or enclosed by the coating material which may include, e.g., polymeric or ceramic materials and metals. Furthermore, the coating material may include different regions of varying thickness or other features incorporated into the material. The polymer may include a number of different types, e.g., silicone, polyurethane, polyepoxide, polyamides, or blends thereof, etc. In alternative embodiments, the lattice structure may be impregnated in and/or enclosed by a foamed solid.

In certain embodiments, the lattice structure may be defined by a plurality of unit cells with a size between, e.g., 1 and 20 mm. In other embodiments, the lattice structure may be provided with varying unit cell geometries having cell varying dimensions and/or varying structure densities. In other embodiments, the lattice structure may be comprised of at least two separate lattice structure parts movably connected to each other and integrated into the structure.

In certain embodiments, the free-form structure may further include one or more external and/or internal sensors (e.g. pressure and/or temperature sensors) and/or one or more external and/or internal markers (e.g. position markers). Such markers can be read externally to determine current tooth movement to help the practitioner in deciding future movement adjustments, if needed.

In certain embodiments, the free-form structure may further include one or more agents disposed externally and/or internally such as various chemicals or drugs, e.g., tooth whitening materials, insulin which can be slowly delivered orally to a diabetic patient, etc. Such chemicals, drugs, or medicine can also be incorporated to loosen up the gums and/or tendons to enable teeth move faster, wound treatments, etc.

In certain embodiments, the free-form structure may further comprise one or more external and/or internal locators so that, when such a device is misplaced, the user can use a mobile computer to detect the location and find the device. The locator can include any number of devices, e.g., magnets, wireless proximity detectors, optical proximity detectors, etc.

The free-form structures can also be further configured to have different stiffness values in different regions of the structure utilizing a number of different configurations.

In one aspect, systems and methods are disclosed for fabricating one or more oral appliances by capturing a three dimensional representation of a body part of a subject such as the dentition and creating a removable inner support structure. One or more of the oral appliances may be fabricated directly upon one or more corresponding support structures. Once the oral appliance has been completed, the inner support structure may be removed to leave the dental appliance that fits over one or more teeth for correcting malocclusions in the dentition.

One method for fabricating an oral appliance may generally comprise capturing a three dimensional representation of a dentition of a subject, fabricating a support structure which corresponds to an outer surface of the dentition, forming one or more oral appliances upon an exterior surface of the support structure such that an interior of the one or more oral appliances conform to the dentition, and removing the support structure from the interior of the one or more oral appliances.

The one or more oral appliances may be formed in a sequence configured to move one or more teeth of the subject to correct for malocclusions. Moreover, the support structure may be fabricated from a first material and the one or more oral appliances may be fabricated from a second material different from the first material.

Generally, the oral appliance assembly may comprise the support structure having an exterior surface which corresponds to an outer surface of the dentition of the subject, wherein the support structure is fabricated from a first material, and the oral appliance formed upon the exterior surface of the support structure via three dimensional printing such that an interior of the formed oral appliance conforms to the dentition of the subject, wherein the oral appliance is fabricated from a second material different from the first material.

The support structure is generally removable from the interior of the formed oral appliance such that the oral appliance is positionable upon the dentition. Furthermore, a plurality of oral appliances may be formed where each oral appliance is formed in a sequence configured to move one or more teeth of the subject to correct for malocclusions. Accordingly, each oral appliance may be formed upon a plurality of corresponding support structures.

The structures according to the present invention can have a different stiffness in different parts of the structure and can be made transparent, even though they are made at least partially via additive manufacturing. The free-form structures according to the present invention can further be made as a single part, and may further comprise internal or external sensors.

Systems and methods are disclosed for cutting and trimming dental molds and oral appliances by receiving a digital model of teeth, determining a cutting loop path and applying a drape wall to the cutting loop to generate a simplified tooth base in a dental mold having an inner arch curve and an outer arch curve. The oral appliance may be formed on the dental mold and a cutter may be applied using a single sweeping motion across the inner and outer arch curves.

The system enables an easy way to cut and trim tooth models. The system allows close control by the treating professional at each stage by allowing specific movements from one stage to the next stage. The system can form aligners quickly and efficiently due to the drape wall simplification. The CNC machines can manufacture each shell as a custom device for many stages of tooth movement. The mold can be cut/trimmed using inexpensive 2D cutting machines, if needed. Additionally, the resulting oral appliances (aligners, shells, etc.) can be removed from the positive mold with minimal force, reducing risk of shell tear from excessive removal force.

Generally, one embodiment for a method of forming an oral appliance may comprise receiving a digital model of a patient's dentition, calculating a rule-based cutting loop path on the model for determining a path for trimming a mold replicating the patient's dentition, applying a drape wall from the cutting loop on the model to reduce a complexity of the model, determining a position of a cutting instrument relative to the mold for trimming the mold, generating a computer numerical control code based on the drape wall and position of the cutting instrument, and fabricating the mold based on the generated computer numerical control code.

Another embodiment for a method of forming an oral appliance may generally comprise receiving a digital model of a patient's dentition, calculating a rule-based cutting loop path on the model for determining a path for trimming a mold replicating the patient's dentition, applying a drape wall from the cutting loop on the model to reduce a complexity of the model, determining a predetermined height of a base of the model, generating a computer numerical control code of the model, and fabricating the mold based on the generated computer numerical control code.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

DETAILED DESCRIPTION OF THE INVENTION

Figure 1A:
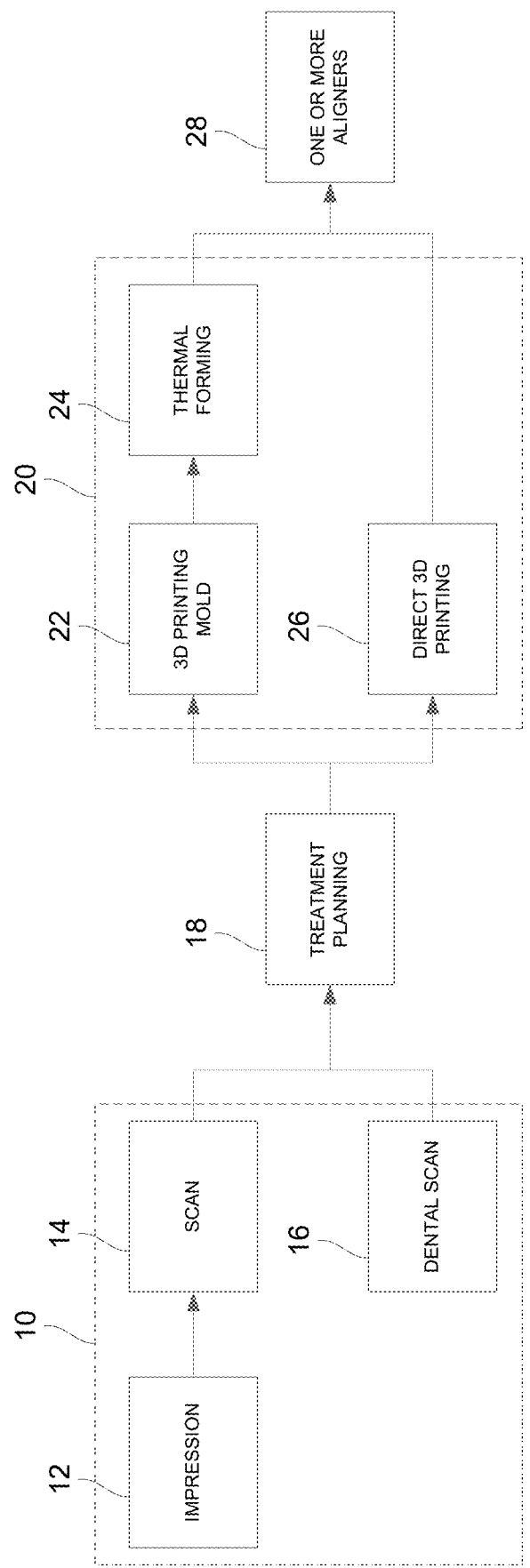
FIG. 1A shows an exemplary process for scanning the patient's dentition, treatment planning, and then fabricating one or more aligners for effecting patient treatment.

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In treating a patient to correct for one or more conditions with their dentition, the steps of digitally scanning the patient's dentition, planning the treatment, and/or optionally fabricating the treatment devices, such as aligners to correct positioning of one or more teeth, may be performed directly at the provider's office.

As shown in the exemplary process of FIG. 1A, the step of scanning the patient's dentition 10 may be performed using a number of different processes, as described in further detail herein. With the resulting digital images of the patient's dentition, the treatment planning 18 to correct for the positioning, misalignment, malocclusion, etc. of any one or more teeth may be performed using any of the processes described herein. Conventional treatment planning typically creates an entire treatment plan starting with the initial positioning of the patient's dentition and formulating a treatment based on a stepped realignment of the dentition. This stepped realignment is then used to create an entire array of aligners starting with an initial aligner and ending with a final aligner for use through the entire treatment process.

However, the treatment planning 18 and fabrication process 20 described herein may be performed on a variable treatment path. That is, while the initial treatment planning 18 may be based upon the initial positioning of the patient's dentition, the step-by-step process for subsequent treatments is variable such that the final treatment step is not pre-determined. Rather, the alignment of the dentition is determined at intermediate steps in which the patient may (or may not) come back to the practitioner's office for reassessments and potentially new scans and aligners for one or more intermediate treatment steps. In this manner, additional aligners or other treatment processes may be created during each visit to the practitioner by the patient. Hence, the entire treatment process is created as the treatment progresses thus leading to the treatment planning 18 and fabrication process 20 as an iterative process rather than an entire treatment sequence pre-determined at the treatment outset.

Figure 1B:
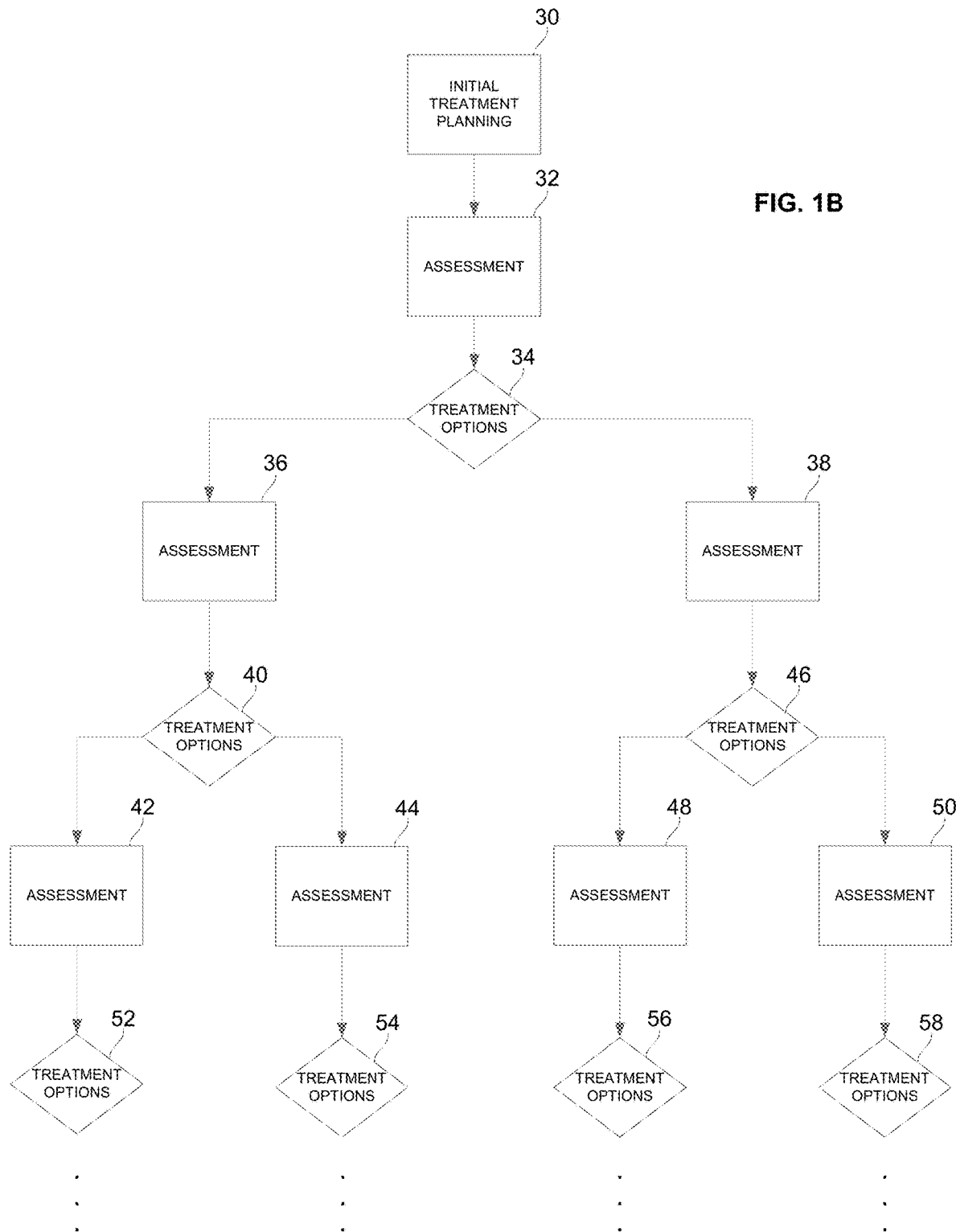
FIG. 1B shows an example of a flow diagram illustrating how an initial treatment planning may be reassessed and additional treatment options may be generated or considered during additional treatment planning.

An example is shown in the flow diagram of FIG. 1B which illustrates how the initial treatment planning 30 may be performed and one or more initial aligners may be fabricated for use by the patient. After initial treatment, the patient may be assessed 32 and additional treatment options 34 may be generated or considered during additional treatment planning. Based on the assessment 32, various treatment options may be considered and the patient re-assessed 36, 38, for example, after a predetermined period of time. The assessment may be formed by the practitioner based on the progress or lack of progress of moving the patient's tooth or teeth to a desired position. Additionally, the patient may also collaborate with the practitioner to provide their own assessments, thoughts, etc. so that the practitioner may consider not only the physiological data but also the collaboration provided by the patient.

Depending on which treatment option was pursued, additional treatment options 40, 46 may be considered and their corresponding outcome re-assessed 42, 44, 48, 50 again depending on which treatment option was pursued. Depending upon the assessment and, if needed, the patient may again be provided with treatment options 52, 54, 56, 58 and the process may be continued at predetermined intervals until the desired outcome is reached. Because the treatment process is not predetermined from the start to the end of the entire treatment and the treatment options may be varied, the aligners may be fabricated with only a few at a time. This also provides flexibility to the practitioner to alter the treatment mid-course without having an entire array of pre-fabricated aligners un-used.

Returning to FIG. 1A, the fabrication process 20 itself may be accomplished through different methods. In one example, the model of the partially corrected patient dentition may be formed as a positive mold, e.g., via a 3D printing mold 22 and corresponding aligner or aligners may be thermal formed 24 upon the positive molds. In another example, the one or more aligners may be directly formed, e.g., direct 3D printing 26. In either case, the resulting one or more aligners 28 may be formed for use by the patient.

Scanning the Dentition

Obtaining a digital model of the patient's dentition for facilitating the treatment planning may be accomplished in a number of different ways. The patient may have their dentition scanned at another location and forwarded to the treatment provider or their dentition may be scanned directly at the treatment provider's location. In either case, the patient's dentition may be digitally scanned through any number of suitable scanning devices. For example, the patient may have their dentition (including teeth, soft tissue, or both) scanned by an MRI scanner, X-ray machine, intra-oral scanner, etc. The resulting scanned images may be saved or uploaded to a computer system and used to generate a digital image of the teeth which may be used for planning the treatment to correct for the positioning, misalignment, malocclusion, etc. of any one or more teeth. Alternatively, the patient's dentition may be cast to obtain an impression which may then be used to create a positive mold. The resulting positive mold reflecting the patient's dentition may then be scanned to obtain the corresponding digital image.

Treatment Planning

The treatment planning process may be implemented after receiving and analyzing the scanned dental model of a patient's dentition. The scanned dental model may be accordingly processed to enable the development of a treatment plan which can be readily implemented for fabricating one or more positioners for use in effecting sequential tooth movements.

Figure 2A:
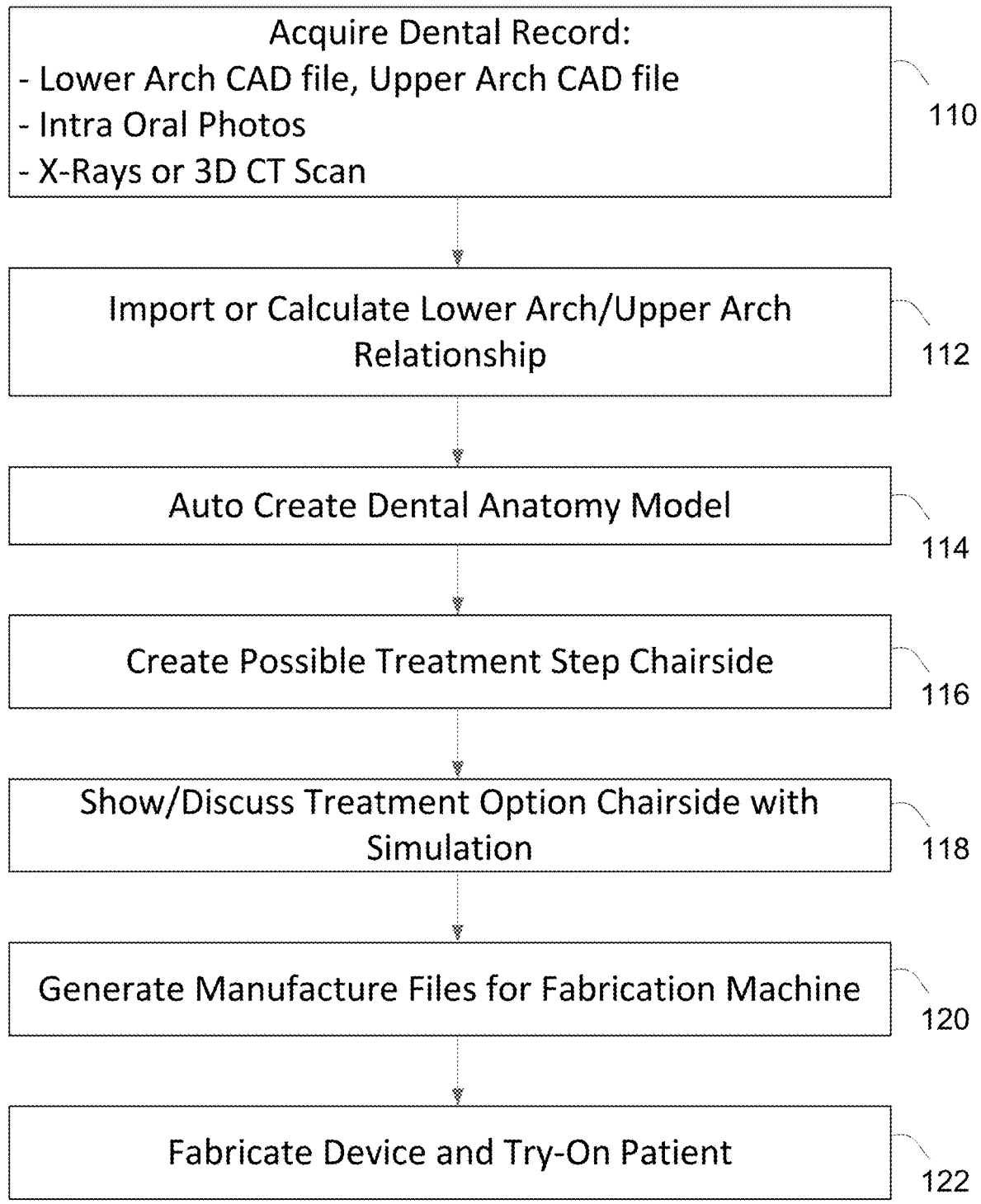
FIG. 2A shows a flow diagram of one exemplary method for a tooth modeling system.

FIG. 2A shows an exemplary overall tooth modeling process which may be used in planning the treatment for correcting malocclusions in a patient. The process shown may involve initially acquiring a patient's dental record 110 in the form of, e.g., lower arch and/or upper arch CAD files, intra oral photos, X-rays or 3D CT scans, etc. The lower arch and/or upper arch CAD files may be created, for instance, through a number of different methods, such as taking lower and upper impressions of the patient's dentition, X-rays, etc.

Once the dental records are acquired, the lower arch and upper arch relationship may be imported or calculated 112 for registration by one or more computing devices and a flexible dental anatomy model may be auto created 114 by one or more processors located locally in proximity to where the patient is treated, e.g., dental office, or remotely from the patient location. Once the dental anatomy model has been digitally created and confirmed to fit and that the arch model can open and close as expected, one or more possible treatments may be created in real-time chairside of the patient 116 and the one or more treatment options may be may be shown and/or discussed with the patient chairside 118 where simulations of the treatment options may also be shown and/or discussed for potentially altering the treatment plan as needed. The simulations of treatment options may be displayed to the patient using any number of electronic display methods.

Following the discussion of the treatment options with the patient, the treatment plan (with any alterations) may be used to generate manufacturing files for the fabrication machinery 120, e.g., 3D printing machines, thermal forming, laser sintering, etc. Because the resulting one or more positioners may be fabricated locally in proximity to the patient (e.g., dental office, clinic, nearby facility, etc.) the one or more resulting positioners for use by the patient may be fabricated locally allowing for the patient to try on the one or more positioners 122 during the same visit.

Such a treatment plan may have particular advantages over conventional planning and treatment plans including one or more of the following:
- exact treatment may be developed right way and discussed with the patient in real time;
- practitioner has full control of the treatment plan options which are easy to create;
- real gum modeling may be implemented;
- one or more positioners may be fabricated locally allowing the patient to try-on during the same visit;
- easy to incorporate other treatment methods, e.g. indirect bonding bracket, rubber bands, hooks, retainers, etc. in combination with one or more positioners.

Figure 2B:
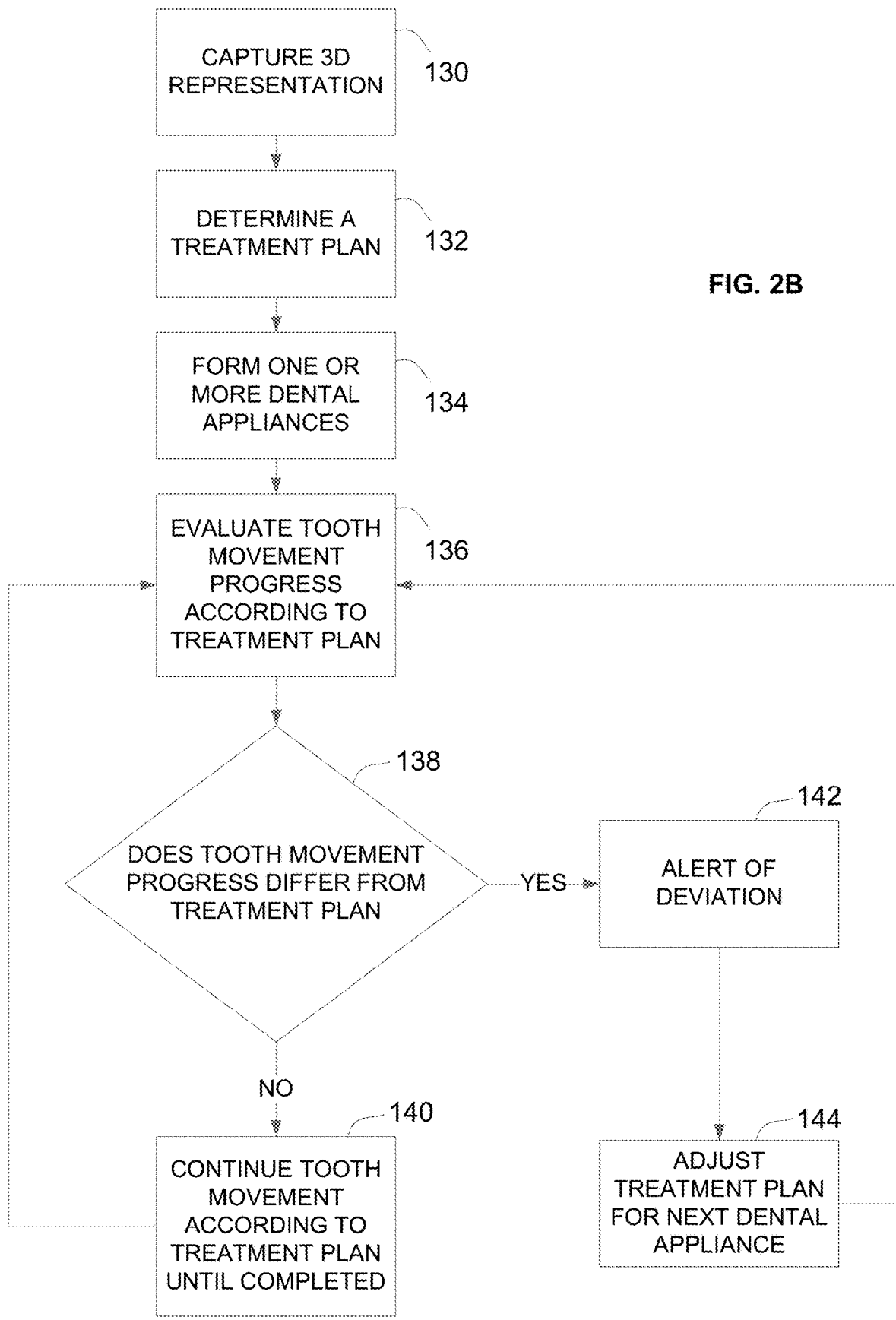
FIG. 2B shows another exemplary method for adjusting a treatment process when results deviate from the initial treatment plan.

Even in the event that a treatment plan has been developed and implemented for a patient, as shown and described for FIG. 2A, the actual progress of the tooth movement(s) may not correspond to the treatment plan or the actual progress may begin to deviate from the treatment plan. Because of this variability, not all of the positioners or aligners may be fabricated at the start of the treatment but the positioners may instead be fabricated in preset stages for use by the patient until a subsequent visit to the practitioner, e.g., every six weeks, where a new set of positioners may be fabricated for subsequent treatments. FIG. 2B shows an example of this staged treatment planning where the treatment plan may be adjusted during the actual treatment according to any changes or deviations by the patient's progress. Furthermore, the implementation of a staged treatment planning process also enables the practitioner to employ other devices or methods (e.g., brackets, wires, etc.) for correcting malocclusions in addition to or in place of the fabricated positioners.

As described above, the patient's dentition may be scanned or otherwise recorded to capture a three-dimensional (3D) representation 130 of the patient's dentition and an initial treatment plan may be determined 132 for forming one or more dental appliances 134 for correcting any malocclusions. Rather than fabricating the dental appliances for the entire treatment process, a staged number of appliances may be initially fabricated for use by the patient until their subsequent visit. The practitioner may evaluate the patient's tooth movement progress at subsequent visits according to the treatment plan 136 as originally developed. In determining whether the patient's tooth movement progress differs from the treatment plan 138, the practitioner may compare the treatment plan with the patient's actual tooth movement(s) to determine whether they correlate with one another. Such a comparison may be done in a number of ways, e.g., visually by the practitioner or the patient's dentition may be scanned again and the captured 3D representation of the treated dentition may be digitally compared against the treatment plan.

If the system determines that the actual tooth movement progress does not differ from the treatment plan, the tooth movement may be continued according to the treatment plan 140 without alteration and an additional number of positioners may be fabricated for use by the patient until the subsequent visit. Provided that the next visit and subsequent visit tracks according to the original treatment plan, the additional set of positioners may be fabricated until the treatment has been completed and the malocclusions corrected.

However, if during any one of the evaluations the practitioner determines that the actual tooth movement does differ from the treatment plan, the practitioner may be alerted of the deviation 142 by the system. The treatment plan may then be automatically adjusted by the system for the next set of dental appliances or positioners 144 to correct for the deviations so that the newly fabricated positioners provide for a better fit to the patient's dentition and is responsive to correcting for the deviations. At subsequent visits, the tooth movement with the altered treatment plan may be evaluated 136 to determine whether the tooth movement differs from the altered treatment plan 138 and if no deviation is detected, treatment may be continued but if a deviation is detected, the practitioner may be alerted of the deviation and the altered treatment plan again be adjusted accordingly. This process may be continued until the detected tooth movements appear to follow the treatment plans.

Because the system is programmed to alert the practitioner of any deviations for particular teeth, the practitioner is able to determine if the patient is non-compliant with wearing the positioner and/or whether any there are any problematic tooth movements which the practitioner can then flag for continuing treatment or whether other devices or methods, e.g., conventional braces, may be employed for particularly problematic teeth. The treatment plan (as any subsequent treatment plans) may be shared with others through any number of methods and/or devices.

In importing or calculating the relationship between the lower arch and upper arch 112, the digital models of the lower arch and/or upper arch may be loaded 150, e.g., into a computer, as shown in the flow diagram of FIG. 3. Additionally, as part of creating a dental anatomy model 114, the bite registration between the lower arch and upper arch may be set and mounted on a virtual articulator 152 and the user may then drag and drop the tooth ID to an area of interest 154 for correcting the malocclusion. In digitally modeling the margin between the crown and gum, the process may assign regions that are designated as "hard" and "soft" 156 with conditions set where a region with a "hard" designation cannot change its shape and a region with a "soft" designation is able to be deformed with an attached "hard" region.

Additionally, any number of moving widgets may be defined at various regions or locations 158 for facilitating the movement and control of the regions. For instance, the process may allow for defining moving widgets: mesial/distal, lingual/facial, vertical, etc. Moreover, the user may be enabled to control the widgets and calculate a morphed new model 160 in developing a treatment plan. Once the treatment plan has been completed, the plan may be exported, e.g., to a 3D printer acceptable model file 162, for use in manufacturing one or more of the positioners or for manufacturing molds for subsequent thermal forming.

Figure 3A:
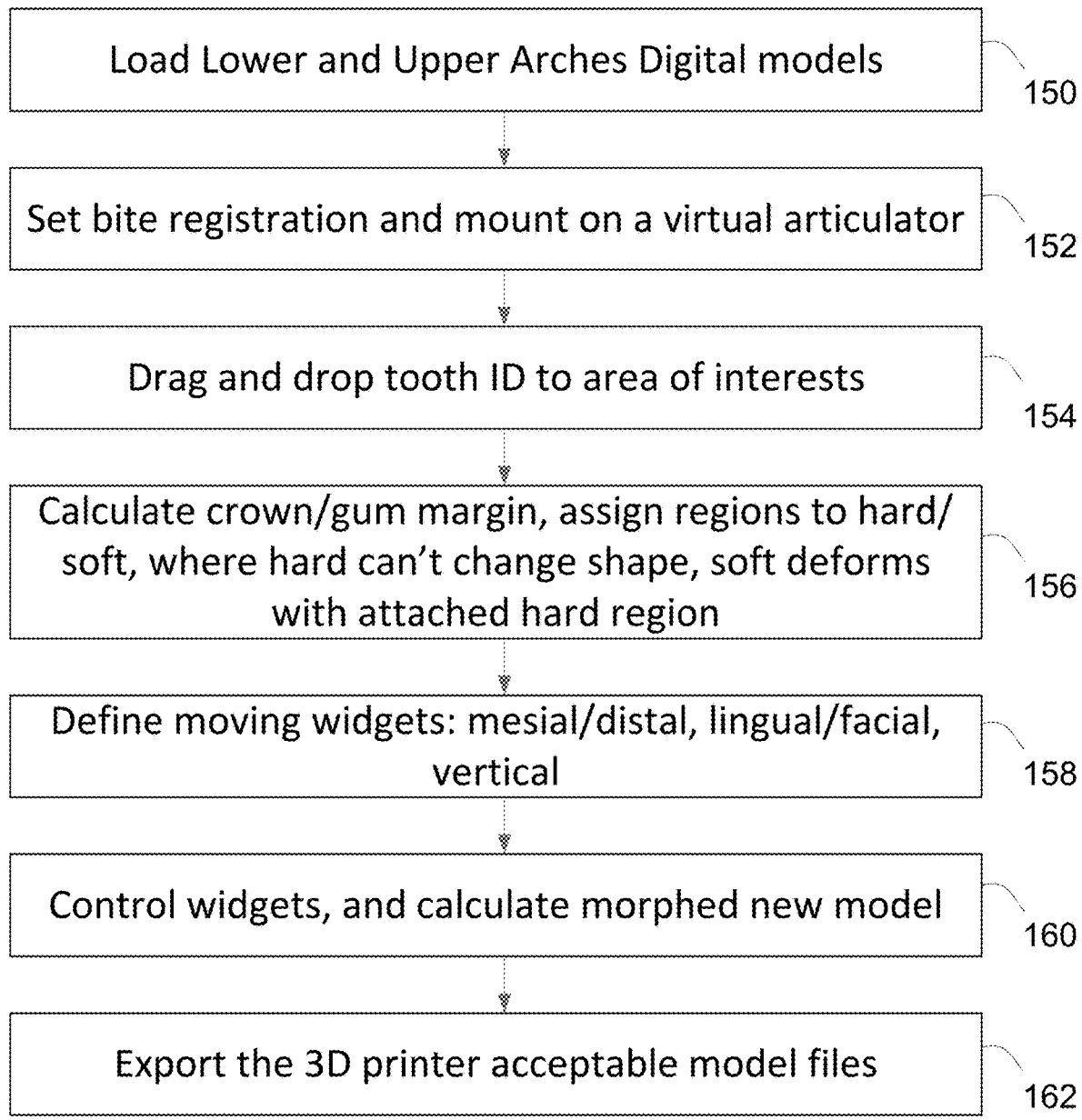
FIG. 3A shows one exemplary process for planning a treatment process in creating a model file.
Figure 3B:
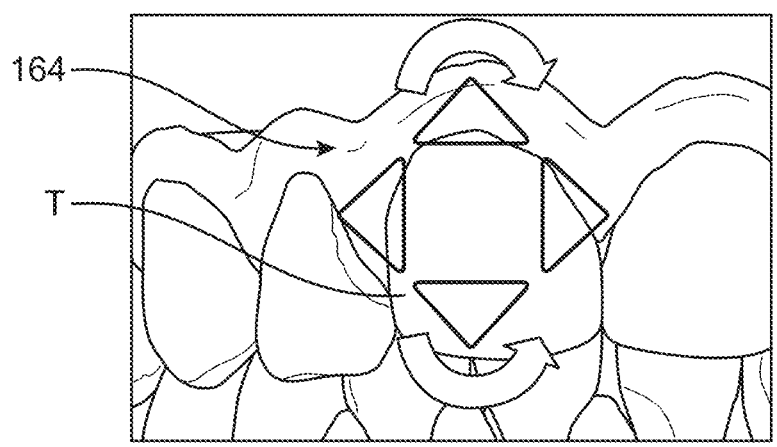
FIGS. 3B to 3D show various views of a tooth to be digitally manipulated via moving widgets displayed upon the tooth of interest.
Figure 3C:
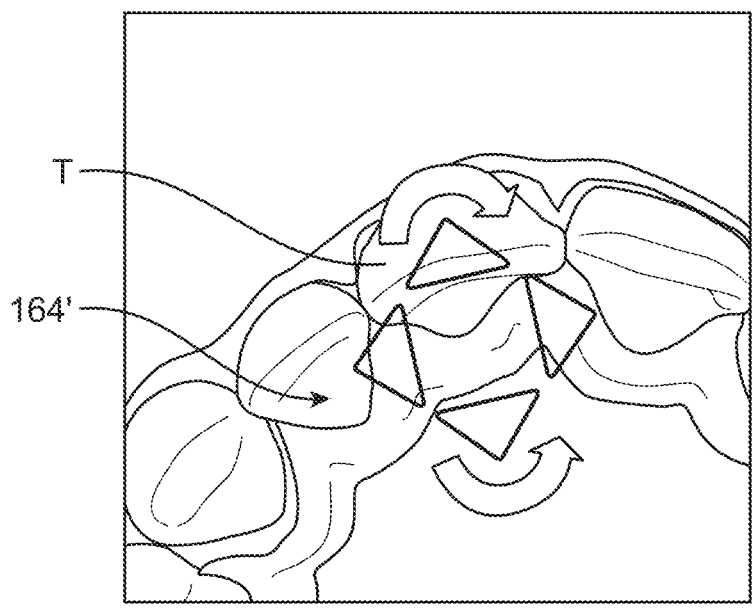
Figure 3D:
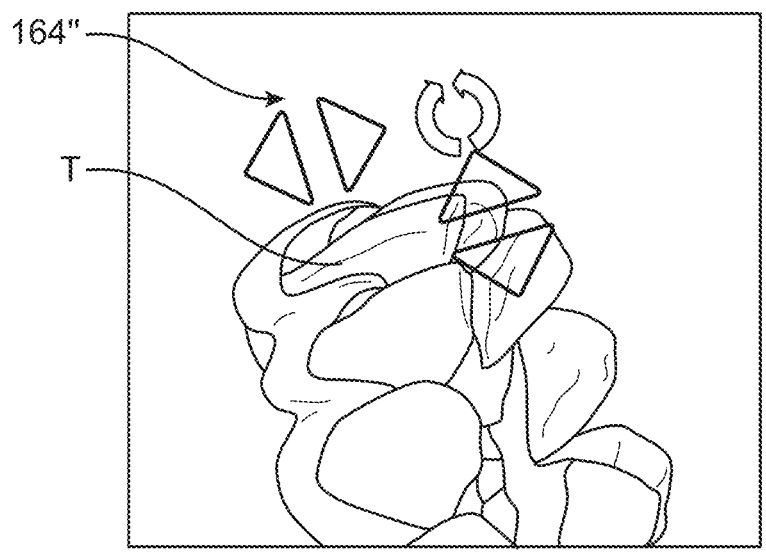

These moving widgets may be view-based widgets which facilitate manipulation of the model in developing the treatment plan. When the model is displayed in a particular view, the manipulation widgets displayed may be programmed to allow for model manipulation only in the particular view which is displayed. For example, FIG. 3B shows a lingual/facial view with the moving widget 164 displayed upon the tooth T of interest to be moved for treatment planning. With the tooth T of interest displayed, e.g., upon a screen or monitor, the movement widget 164 may be displayed upon or over the particular tooth T. The movement provided by the widget 164 may move the digital model of the tooth T in various translational and/or rotational movements. FIG. 3C shows how the tooth T shown in a vertical/apical view may have the moving widget 164' displayed upon the tooth T for digitally manipulating the tooth T and FIG. 3D shows a mesial/distal view of the tooth T with moving widget 164" similarly displayed for treatment planning.

Additionally and/or optionally, each tooth may be displayed either in its native color or alternatively colored, e.g., yellow or red, to indicate to the practitioner that a proposed corresponding movement is difficult or unlikely to be achieved thereby providing the practitioner guidance to find alternatives treatments.

Figure 4:
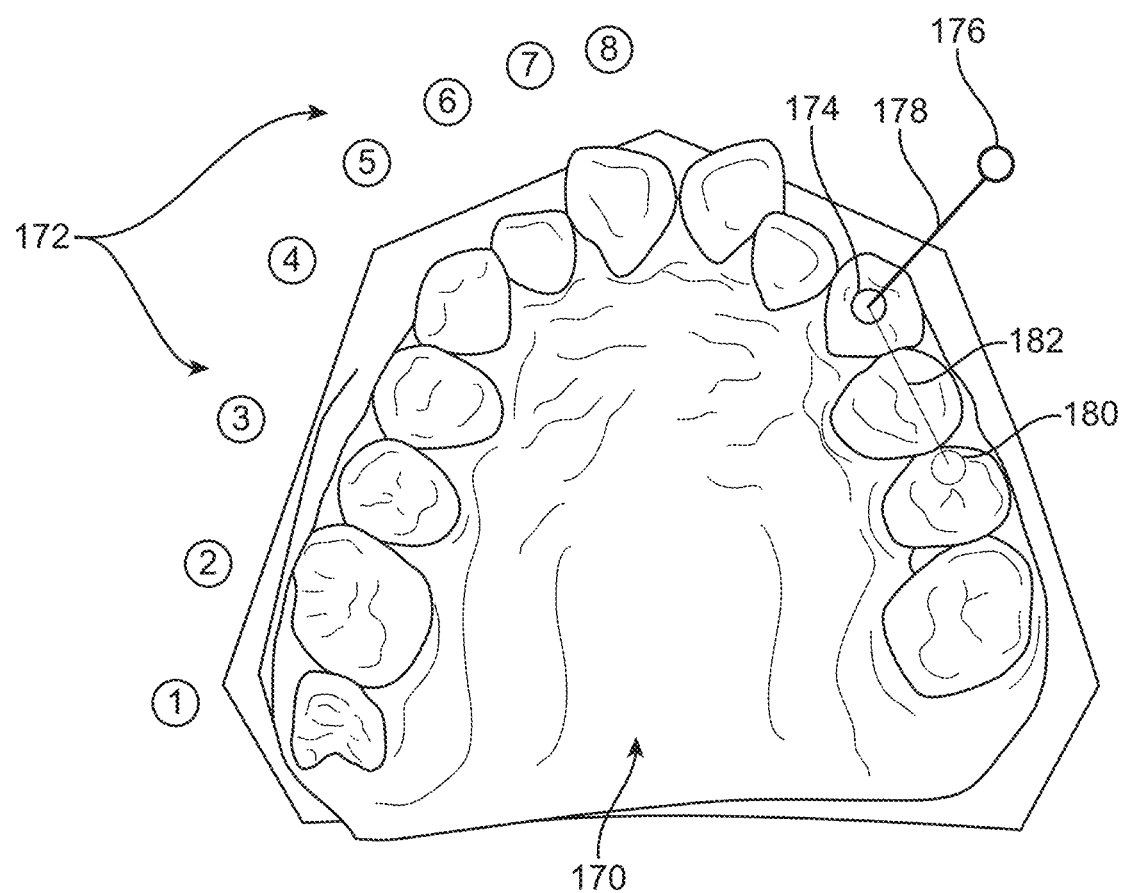
FIG. 4 shows one exemplary labeling system in planning the treatment process.

In preparing the scanned image of the patient's dentition for treatment planning, the digital model may be initially labeled. For example, FIG. 4 shows an example of a labeling system where the scanned dentition model 170 may be seen. A number of labels 172, in this example a total of 16 labels (e.g., 1 to 16 or 17-32 depending on the arch), may be initially laid out alongside the model 170 allowing for the user to assign a label to a targeted tooth by, e.g., dragging and dropping a label to a particular tooth. In this example, while the label is dragged it may remain visible but after being assigned by being dropped upon a particular tooth, the tooth may change to indicate that it has been labeled. For instance, the tooth may be changed in color to indicate that it is now labeled, e.g., from the color red to indicate an unassigned tooth to the color white to indicate the tooth being labeled.

In facilitating the treatment planning, moving widgets may be defined on the digital model 158 and controlled 160 accordingly, as discussed above. As shown in FIG. 4, one example is illustrated of a moving widget where a center vertex 174 indicated as a circle may be defined along the model 170. The selected vertex related mesh should be form a single connected region to provide a way to read the list. The center vertex 174 is indicated as a center while a second vertex 176 may be defined relative to the center vertex 174 such that the first arm 178 defined between may point directly outside the tooth surface in the lingual to buccal direction. A third vertex 180 may be defined relative to the center vertex 174 such that the second arm 182 defined between points along the center of the teeth in the mesial to distal direction. The first arm 178 and second arm 182 need not be perpendicular to one another. The moving widget may be applied only to teeth which are labeled (and hence teeth which may be moved in the model) and may provide a way to read and orient the direction of the arms 178, 182 and their origin. The moving widget may be hidden from view from the user when not in use.

Figure 5:
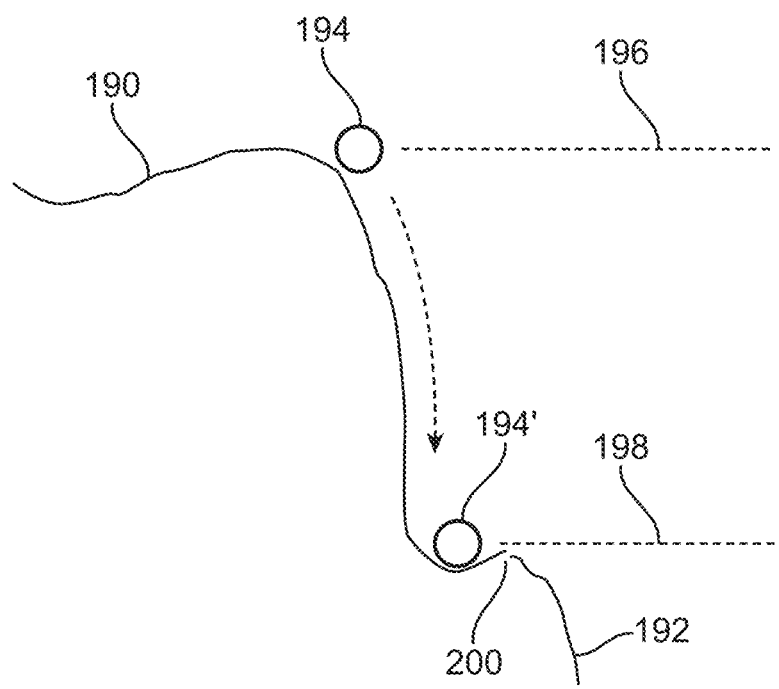
FIG. 5 shows a rolling or dropping ball method for detecting the tooth boundary during treatment planning.

Once the tooth labeled and a small set of mesh are identified, a drop ball algorithm may be used to detect the gum margin and teeth margin. FIG. 5 shows an exemplary process for digitally detecting and identifying a tooth boundary or geometry from the scanned dentition of the patient by simulating a rolling or dropping ball 194 to detect the boundary of the tooth 190 and gum 192. The ball 194 may be simulated to roll from a high energy state 196, e.g., at the tooth crown, to a low resting state 198, e.g., at bottom of the tooth. As the ball 194' rolls down longitude, there is a bump 200 which tip up at the margin area between the tooth and gum where the inflection changes. By looking at these areas and at the correct curvature changes, the margin line can be detected. This method can also detect occlusal teeth margins and gum margins as well.

Figure 6A:
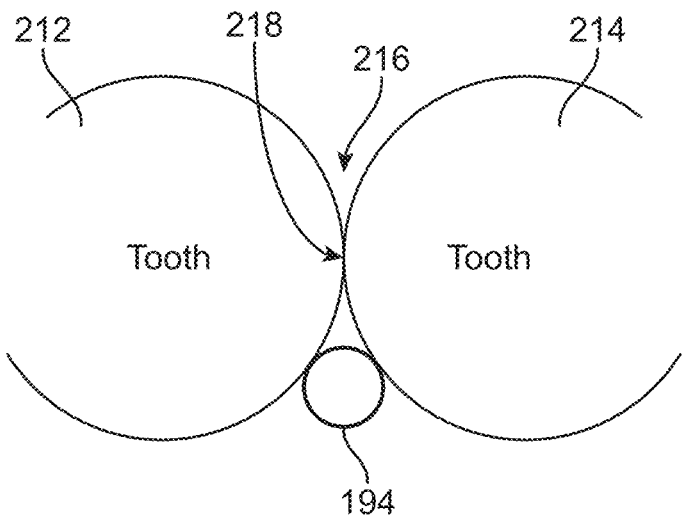
FIG. 6A shows how the rolling or dropping ball follows the clevis of teeth.
Figure 6B:
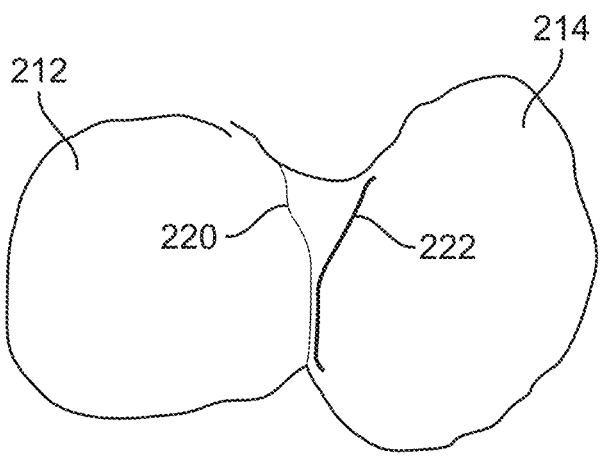
FIG. 6B shows how the ball trajectory path can be used to find the margin lines between adjacent teeth.

However, to detect the side margin between two adjacent teeth, the rolling ball algorithm may be used, as described, to follow the known margin lines of the teeth but in-between the adjacent teeth, the boundary of the teeth may be extrapolated. For instance, FIG. 6A shows an example where the rolling ball 194 may be rolled to follow the outline of adjacent teeth 212, 214. The region 218 in-between the teeth may be generally inaccessible to the ball 194 but the ball will naturally follow the clevis 216 of the teeth. Hence, the extrapolated trajectory path 220, 222 that the rolling ball 194 would follow between the teeth 212, 214 can be used to find the margin lines between adjacent teeth 212, 214 even though the ball 194 may not access the region 218 in-between, as illustrated in FIG. 6B.

Figure 6C:
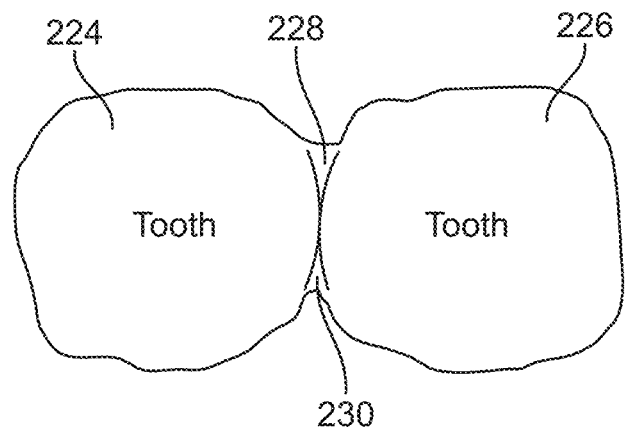
FIG. 6C show how once the margins are defined, the entire dental model may be separated into two portions to detect a tooth boundary or geometry.

As shown in FIG. 6C, once the margins are defined over the model, the entire dental model may be separated into two parts: a hard crown surface and a soft gum surface. In one embodiment, the "hard" surface 224, 226 may be considered a rigid surface which moves in an integral part and maintains its shape whiling moving. The "soft" surface 228, 230 may be attached to the "hard" surface 224, 226 and may deform based on the movements of the hard surface 224, 226. Such a movement does not change the overall topological structure of the dental model, hence the finished model by default is watertight, which fits a 3D printer requirement.

This deviates from the traditional separate model to individual tooth model, which requires models to be trimmed and then capped (hole filling) to make it watertight. Due to the complexity of scanned tooth geometry, such trim and hole filling is a very complex process.

Figure 7:
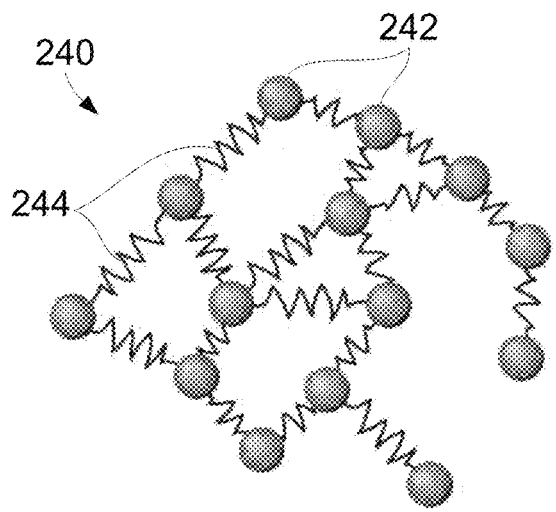
FIG. 7 shows an exemplary mass-spring model which may be used to model the teeth and gums as an interconnected system.

FIG. 7 shows an exemplary mass-spring model 240 which may be applied to the dental model in determining tooth movement. It is generally desirable in some settings to synchronize the movement and operation of the individual tooth models to have a few tooth models operate in a choreographed manner as dictated by a treating professional. Having this choreographed movement is not typically possible through manual control where the tooth models move randomly and independently. The present control method and/or system are ideal for use in moving a number of tooth models and to provide synchronized tooth movement. Such a method may be non-swarming to avoid any collisions between the teeth and to also avoid the appearance of merely random movements, at least in some applications. Rather, it is desirable for the tooth models to each react safely to environmental conditions such as changes in bone structure and soft tissue during group tooth movement of choreographed tooth models.

The mass-spring model 240 may be constrained to be directly attached to a hard surface and the model 240 can be stretched or compressed. Any number of algorithms can be used to calculate its shape, e.g. mass-spring model, in one implementation of mass-spring model 240, two nodes may be modeled as mass points connected by a parallel circuit of a spring and a damper. In this approach, the body is modeled as a set of point masses (nodes) connected by ideal weightless elastic springs obeying some variant of Hooke's law. These nodes may either derive from the edges of a two-dimensional polygonal mesh representation of the surface of the object, or from a three-dimensional network of nodes and edges modeling the internal structure of the object (or even a one-dimensional system of links, if for example a rope or hair strand is being simulated). Additional springs between nodes can be added, or the force law of the springs modified, to achieve desired effects. Having the dental model constrained as a mass-spring model 240 helps to synchronize the movement and operation of the individual tooth models to have a few tooth models operate in a choreographed manner.

Applying Newton's second law to the point masses including the forces applied by the springs and any external forces (due to contact, gravity, etc.) gives a system of differential equations for the motion of the nodes, which is solved by standard numerical schemes for solving ordinary differential equations. Rendering of a three-dimensional mass-spring lattice is often done using free-form deformation, in which the rendered mesh is embedded in the lattice and distorted to conform to the shape of the lattice as it evolves. Assuming all point masses equal to zero, one can obtain the stretched grid method aimed at several engineering problems solution relative to the elastic grid behavior.

Another way to calculate the model 240 is using finite element analysis (FEA) models where the "soft" parts of the model are separated into smaller FEA elements, e.g., tetrahedron or cube elements, and some of the element surfaces may be attached to "hard" portions as so called boundary condition in FEA analysis while "soft" portions (gum portions) may be assigned various material properties such as Young's Modulus consistent with gum portions. While the hard parts are moving, the boundary condition may change and hence all the elements based on its connections to its neighboring elements may form large matrices. By solving such matrices, each individual element shape and locations may be calculated to give a calculated gum deformation during treatment.

In one embodiment, the body may be modeled as a three-dimensional elastic continuum by breaking it into a large number of solid elements which fit together, and for which a model of the material may be solved for determining the stresses and strains in each element. The elements are typically tetrahedral, the nodes being the vertices of the tetrahedra (tetrahedralize a three dimensional region bounded by a polygon mesh into tetrahedra, similarly to how a two-dimensional polygon may be triangulated into triangles). The strain (which measures the local deformation of the points of the material from their rest state) may be quantified by the strain tensor. The stress (which measures the local forces per-unit area in all directions acting on the material) may be quantified by the Cauchy stress tensor. Given the current local strain, the local stress can be computed via the generalized form of Hooke's law. The equation of motion of the element nodes may be obtained by integrating the stress field over each element and relating this, via Newton's second law, to the node accelerations.

An energy minimization method can be used, which is motivated by variational principles and the physics of surfaces, which dictate that a constrained surface will assume the shape which minimizes the total energy of deformation (analogous to a soap bubble). Expressing the energy of a surface in terms of its local deformation (the energy is due to a combination of stretching and bending), the local force on the surface is given by differentiating the energy with respect to position, yielding an equation of motion which can be solved in the standard ways.

Shape matching can be used where penalty forces or constraints are applied to the model to drive it towards its original shape (e.g., the material behaves as if it has shape memory). To conserve momentum the rotation of the body must be estimated properly, for example via polar decomposition. To approximate finite element simulation, shape matching can be applied to three dimensional lattices and multiple shape matching constraints blended.

Deformation can also be handled by a traditional rigid-body physics engine, modeling the soft-body motion using a network of multiple rigid bodies connected by constraints, and using, for example, matrix-palette skinning to generate a surface mesh for rendering. This is the approach used for deformable objects in Havok Destruction.

Figure 8:
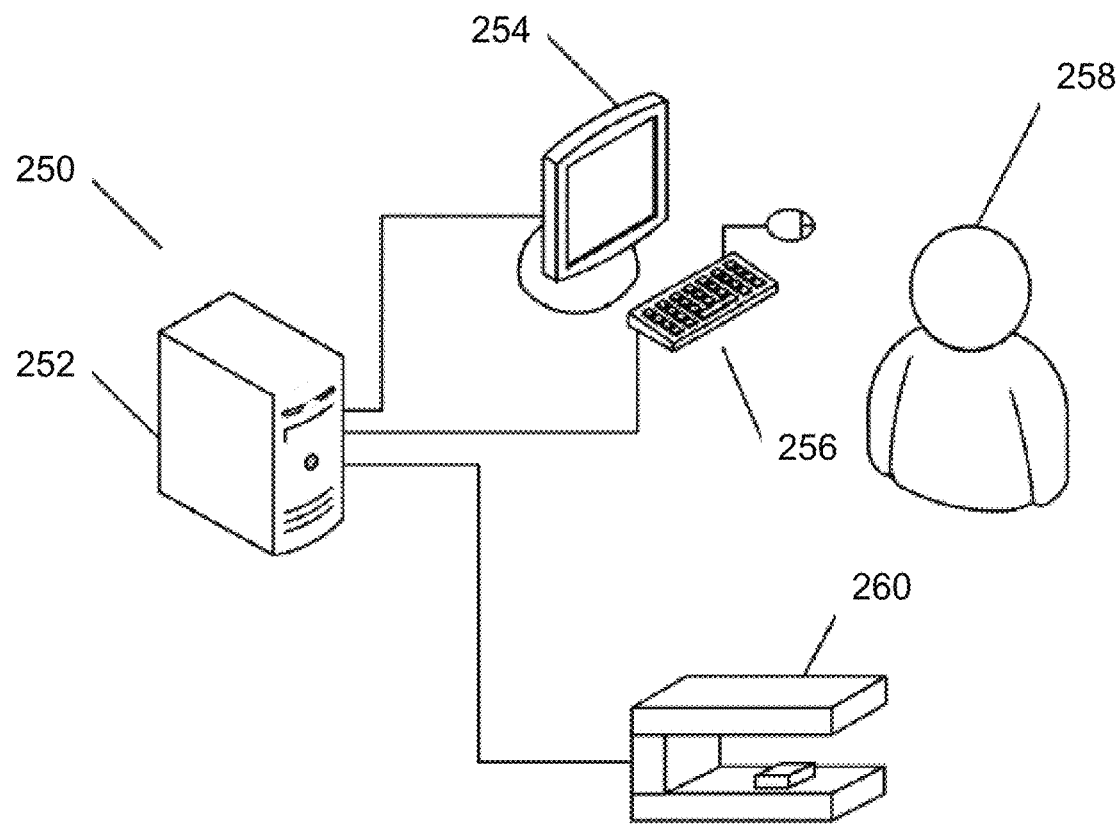
FIG. 8 shows an example of how the treatment planning may be implemented with respect to the patient.

The processes, computer readable medium and systems described herein may be performed on various types of hardware, such as computer systems 250, as shown in FIG. 8. Such computer systems 250 may include a bus or other communication mechanism for communicating information and a processor coupled with the bus for processing information. A computer system 250 may have a main memory, such as a random access memory or other dynamic storage device, coupled to the bus. The main memory may be used to store instructions and temporary variables. The computer system 250 may also include a read-only memory or other static storage device coupled to the bus for storing static information and instructions.

The computer system 250 may also be coupled to a display, such as a CRT or LCD monitor 254. Input devices 256 may also be coupled to the computer system 250. These input devices 256 may include a mouse, a trackball, cursor direction keys, etc. for use by the user 258. Computer systems 250 described herein may include, but are not limited to, the computer 252, display 254, scanner/3D printer 260, and/or input devices 256. Each computer system 250 may be implemented using one or more physical computers or computer systems or portions thereof. The instructions executed by the computer system 250 may also be read in from a computer-readable medium. The computer-readable medium may be a CD, DVD, optical or magnetic disk, laserdisc, carrier wave, or any other medium that is readable by the computer system 250. In some embodiments, hardwired circuitry may be used in place of or in combination with software instructions executed by the processor.

As will be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described herein may be embodied in, and fully automated via, software code modules executed by one or more general purpose computers or processors, such as those computer systems described herein. The code modules may be stored in any type of computer-readable medium or other computer storage device. Some or all of the methods may alternatively be embodied in specialized computer hardware.

It should be emphasized that many variations and modifications may be made to the herein-described embodiments, the elements of which are to be understood as being among other acceptable examples. All such modifications and variations are intended to be included herein within the scope of this disclosure and protected by the following claims.

Aside from processes for modeling the individual teeth and tissues, there are additional control methods and systems (or multiple tooth model systems incorporating such control methods/systems) for use in controlling a flock of tooth models numbering from 1 to 32. That is, the method treats groups of teeth as a flock (e.g., such as a flock of birds which travel collectively) in planning the movements of the teeth for treatments to correct for malocclusions.

Briefly, the control method uses hierarchical-based supervisory control with multicasting techniques along with adaptive logic including onboard or local control modules provided on each tooth model to adjust tooth movement paths to safely avoid collisions based on communication with nearby tooth models. The result of the described control of the multiple tooth models in an oral cavity is a flocking behavior in which the tooth models appear to move in a synchronized manner with movements that are neither completely independent nor completely centrally controlled.

The control method in planning a treatment may be implemented in a system 310 generally having several components including a tooth movement manager module 312, collision manager module 314, and tooth manager module 316 for controlling the movement of tooth models. These components or aspects of the control method/system 310 communicate with a computer system 318 and are described below and as shown in FIG. 9.

Figure 9:
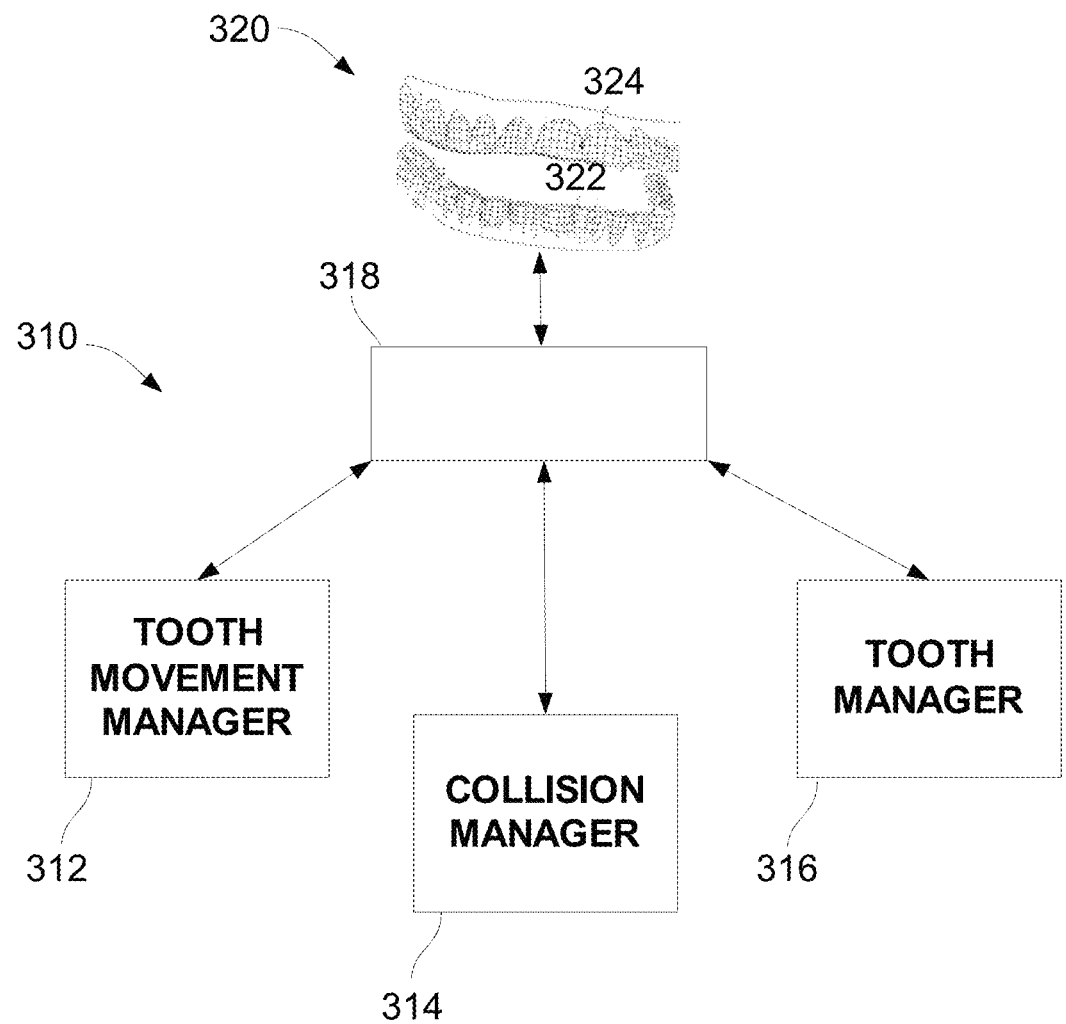
FIG. 9 is functional block diagram of a multiple tooth model system useful for implementing the tooth movement control techniques described herein.

FIG. 9 illustrates a tooth controller/computer or teeth movement control system (TMCS) 310 that may be used to control tooth movement in a safe and repeatable manner. The system 310 includes tooth movement manager module 312 which communicates with the computer system 318 (which includes one or more processors) upon which the digital tooth models of a patient's teeth 320 reside. As shown, the digital tooth models on the computer system 318 are configured for an inter-tooth model or tooth communications and, as explained herein, this intercommunication allows the teeth 320 to safely change its path for correcting malocclusions by determining whether particular teeth 322, 324 are in conflicting movement pathways to avoid collisions while generally remaining on a predefined tooth movement path.

During runtimes, the tooth movement manager 312 is programmed to send commands to the computer system 318 to monitor and maintain performance and quality and also to monitor safety of the teeth to be moved. The tooth movement manager 312 is further programmed to upload tooth movement requirements to the computer system 318 during downtimes, e.g., non-runtimes.

A second module, collision manager module 314, may be programmed to interact with the computer system 318 to handle collisions between teeth to be moved. The collision manager 314 may be programmed to perform the following logic: (a) calculate a "sphere of influence" on each tooth model, e.g., determine a proximity distance between each tooth model to trigger a collision event and if a tooth model enters this sphere of influence around a specific tooth model, a collision event is triggered; (b) determine through a nearest neighbor algorithm whether a possible conflicting pathway will occur; and (c) present to the operator on a user interface provided on the computer system 318 (e.g., via a monitor device) that a potential pathway conflict will occur between any two teeth. The collision module 314 may store the tooth movement paths in memory, e.g., within computer system 318.

Another module includes a tooth manager module 316 which is programmed to monitor the expected state and the actual state of each of the teeth 320. For example, the module 316 may compare a present position or traveling speed of, e.g., tooth 324, with its expected state which may be defined by a tooth movement path or a choreographed and/or time-synchronized movement of tooth models such as with a treatment animation. Based on this monitoring, the tooth manager module 316 may make adjustments such as using the following priorities: localization (e.g., position of the a tooth model with respect to another tooth model or teeth); environment (e.g., adjusting for bone conditions or the like); safety (e.g., returning the tooth model to a safe location or operating mode if the tooth model or other tooth models are not operating as expected); show performance (e.g., adjusting position, speed, or other operating parameters to meet show needs); tooth status; and operator convince/performance needs.

As discussed above, the tooth manager module 316, collision module 314, and tooth movement manager 312 are configured to work together to provide flocking-type control. In use, the inter-tooth model communications allows operational data to flow or spread hierarchically among each of the tooth models rather than relying upon centralized/ tooth movement control alone. In other words, the tooth manager module 316 provides a level of centralized control or central logic that acts to control the movement of the tooth models/teeth such as by providing tooth movement paths provided by the tooth movement manager module 312 and/or making real-time adjustments based on a comparison of expected state and actual state (or for safety reasons) as provided by the collision manager module 314. With regard to inter-tooth model communications, it may be useful to note the following: (a) some units may be designated as master nodes talking with the tooth manager 316; and (b) the master nodes may operate to send out in-tooth movement calculated information or commands to remaining tooth models.

The movement of the individual tooth models and control of the models are not swarm-based in part because swarming-based tooth models can collide with one another or have an inherent lack of safety. The system 310 is designed to avoid random movements as the digital tooth models are subject to moving as a flock having synchronized movements among the individual tooth models. However, the inter-tooth model communications as processed and generated by the local control modules allow for each tooth model to react safely to environment conditions such as direction-changing and the presence/movement of neighboring teeth as crossing tooth movement paths is allowed in the system 310. In other words, the onboard logic acts to control the tooth movements so as to avoid collisions while attempting to stay generally on the tooth movement path.

Figure 10:
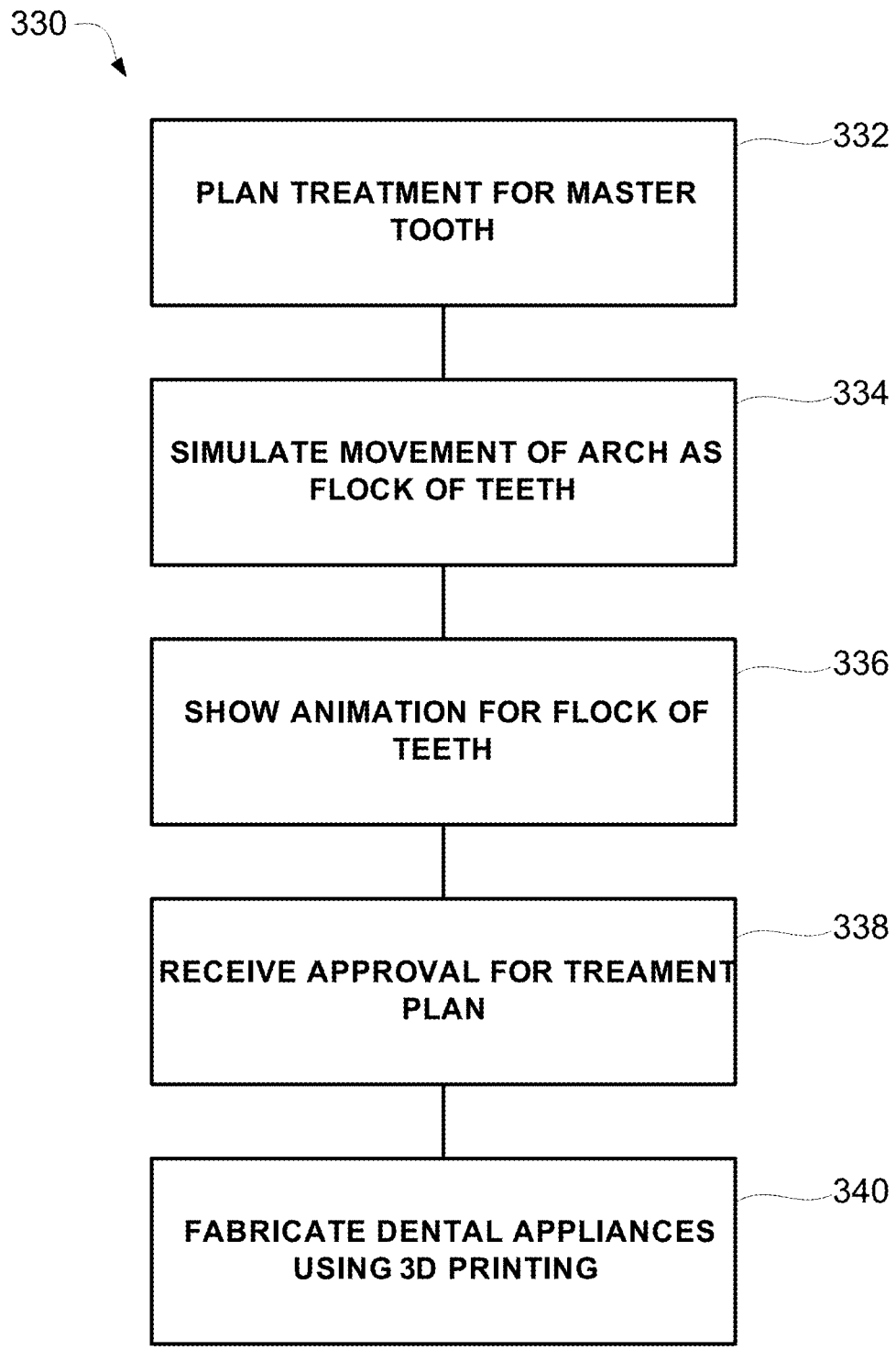
FIG. 10 is a functional schematic or block diagram of a system for use in providing tooth movement management or tooth movement control over two or more moving objects such as tooth models.

FIG. 10 illustrates a general system (or a tooth movement management control system) 330 generally for use in managing or controlling tooth models to provide for synchronized tooth movement by simulating flocking movement of the teeth to correct for malocclusions. As shown, a treatment plan for moving the one or more teeth 332 to correct for malocclusions may be initially developed. The system may include components used to perform off-line activity and used to perform on-line activity. The off-line activity may include designing or selecting a treatment concept or choreographed movement for a plurality of tooth models to achieve a particular effect or perform a task(s). The tooth movement concept (e.g., digital data stored in memory or the like) may be processed with a computer system 318 or other device.

Each tooth to be used may be modeled as a particle to simulate movement of the one or more teeth as a flock of teeth 334 (such as a flock of birds), as described herein. Accordingly, each digitized tooth model may be configured by the computer system 318 to define a three-dimensional space, such as a three-dimensional sphere with a predefined diameter, around each tooth model. This three-dimensional sphere may be used to define a safety envelope for the tooth model or flying object to reduce the risk of a collision between to individual tooth models. For instance, each of the tooth models may be created and create and choreographed by the system 318 to avoid collisions with one another and where two or more tooth models are prohibited from having their safety envelopes intersect or overlap as the tooth models move along their tooth movement paths.

The created tooth movement plan for the multiple tooth models is then exported to memory of computer system 318 or other devices for processing with this "treatment illustration" typically including a file per each tooth model. Each of these files is processed to generate real world coordinates for each tooth model to be achieved over time during an animation or performance of a choreographed task(s) to illustrate the movement of teeth 336, e.g., on a display, to the practitioner and/or patient. This processing creates individual tooth movement plans for each tooth model, and such processing or generating of the tooth movement plans may include processing the modeled animation based on specific logistical requirements. For example, these requirements may be modified, as needed, e.g., is the dental space the same size and shape as in the simulation and, if not, modification may be useful to change or set real world coordinates for one or more of the tooth models.

Once the treatment plan has been approved 338, the treatment plan may be used to fabricate one or more dental appliances or positioners using, e.g., three-dimensional printing 340, locally at the location of the treatment planning.

In planning the simulation of the movement of the individual tooth models as a flock of teeth 334 for working up a treatment plan, the tooth models may be manipulated using the TMCS 310 described herein. The logistical requirements may also include setting a tooth movement truth for the venue and adding safe or "home" points where each tooth can be safely positioned such as at the beginning and end of a treatment process or when a safety over-ride is imparted (e.g., "stop"). A treatment planning management component may be considered a component that translates central treatment plan controller commands where tooth actions are sent to the tooth management component either through scripts (e.g., data files), real time computer messages, and/or hardware triggers.

The tooth movement plans are provided to the TMCS 310, as described above, and the system further includes a number of tooth models shown in the form of teeth in this example. The teeth may be organized into groups or sets with a set shown to include, e.g., two molars, a set including one molars, and a set including cuspid teeth, among others. These sets may act or function together, at least for a portion of an animation or tooth movement path, to perform a particular display or task.

In other cases, all of the teeth may be considered part of large set that moves as a flock or otherwise has its movements time-synchronized and/or choreographed by tooth movement plans. A tooth in the group can communicate with its nearby or neighboring teeth so as to determine their presence, to determine their proximity, and when needed, to process the tooth movement plan, determine neighbor position, and other environmental data to modify their tooth movement plan to avoid collision and/or communicate with the neighboring tooth to instruct it to move or otherwise change its tooth movement plan/movement to avoid collision.

During pre-tooth movement, an operator uses the TMCS to load a tooth movement plan onto each tooth model. During a tooth movement sequence, the TMCS and its tooth manager module 316 acts to run the tooth movement plan previously loaded on the tooth model. During the tooth treatment, the TMCS actively monitors safety and a practitioner can initiate a TMCS user action. More typically, though, the TMCS monitors the operation of all the tooth models in the flock by processing telemetry data provided by each of the tooth models provided by each tooth model. In some embodiments, the tooth manager module 316 has software/logic that compares the actual state of each tooth model against the expected state at that particular time for the tooth model according to the presently enacted tooth movement plan.

After the "go" or start signal is issued by the tooth manager module/TMCS upon an operator input, the TMCS along with the local control software/hardware on each tooth model work to safely perform the preloaded tooth movement plan/show. As discussed above, the control method and system combines centralized, control (e.g., to allow manual override for safety or other reasons during a show/tooth movement-based task) with smart tooth models to more effectively provide flock-type movement of the tooth models. In other words, the tooth models may each be given a particular tooth movement plan that they work towards over time (e.g., during an animation period) while attempting to respond to the unexpected presence of another tooth model within or near to their safety window (or safe operating envelope surrounding each tooth model such as a sphere of, e.g., 1 to 3 mm or the like, in which no other tooth model typically will travel to avoid collisions).

During operations, the TMCS is used to trigger each of the tooth models to begin their stored tooth movement plan starting from an initial start point, e.g., each tooth model may be placed at differing starting points. In some cases after the "go" is received by a tooth model, each tooth model uses its local control module (or other software/programming) to attempt to follow the tooth movement plan but with no time constraints. In other words, the tooth movement plan may define a series of points or way points for the tooth model. In these embodiments, the tooth model is controlled in a relatively fluid manner and not tied to accomplishing specified movements in a certain amount of time, e.g., the tooth movement plan does not require the tooth model to be at a particular location at a particular time after the go signal is received hence allowing for planning flexibility.

In some implementations, the tooth movement plan may be built up assuming that each tooth model travels at a preset and constant tooth movement speed. This tooth movement speed may be set independently for each tooth model or may be the same (or within a relatively small range) for each of the tooth models. In other cases, though, the local control module may be adapted to adjust the tooth movement speed to suit the conditions in the mouth of the patient. The bone hardness may be determined at the tooth model with the local control module and/or via optical sensors for detecting actual tooth movement (rather than planned movement) may be provided by the TMCS to each of the tooth model. In some cases, flock control is preferred such that each tooth model has its speeds adjusted commonly, e.g., each tooth model runs at similar tooth movement speeds while moving in a similar direction so as to appear to have synchronized and non-random movement.

In some embodiment, each tooth model may act independently to try to continue to follow its own tooth movement plan. Each tooth movement plan may differ in that each tooth model begins at a different start point or home and moves toward its first way point. To this end, each tooth model is equipped, as needed, to determine its present three dimensional position along with its present height above the gum line. The local control module uses this present position data to determine or modify, if necessary, its present direction or heading to continue to move toward the next way point in its tooth movement plan. This may involve changing it course and also its angle to reach the desired height at the way point.

An operator may take steps to manually override a particular one of the many tooth models to provide better control of that tooth model. For example, the tooth control module of the TMCS 310 may operate to compare an expected position of the tooth model with its actual position (provided via back end channel in its telemetry or other data). A warning may be provided in a graphical user interface (GUI) that the tooth model is trending off course or is outside an accepted tolerance for reaching its next way point.

For example, the GUI may show properly operating and positioned tooth models in a first color (e.g., green) and tooth models that are off course or out of position by a safe amount in a second color (e.g., yellow) and tooth models outside of a safe envelope in a third color (e.g., red). The red/unsafe tooth models may be handled automatically or manually to cause them to enter a safe mode of operation (e.g., return to home). The yellow tooth models that are operating outside of desired conditions may be manually operated to try to assist them in returning to their tooth movement path such as by manually changing speed, direction, angle of attack, or the like to more quickly bring the tooth model to a desired way point. After manual operations are complete, the control may be returned from the TMCS to the local control module for local control of the tooth model based on the tooth movement plan stored in its memory. The TMCS may be configured to evaluate collision issues and execute collision avoidance commands to preserve show quality (e.g., tooth movement performance) in degrading mouth conditions.

In other embodiments, a local control module of a tooth model may operate to adjust the tooth movement plan during tooth movement to better react to environmental conditions (such as toothache or temporarily gum discomfort, at least temporarily, off course). For example, a tooth movement plan may provide a time relative to a start time (when "go" was signaled by file TMCS to the tooth models) to reach each of its way points on the tooth movement plan. One embodiment may call for a tooth model to determine a distance to a next tooth model and its present estimated time of arrival. If the time of arrival is not within a window about a preset/goal arrival time, the local control module may act to increase the tooth movement speed of the tooth model such as by increasing the rate of rotation of a tooth. Likewise, if the tooth model is moving too quickly, the tooth model's local, control module may act to slow the tooth movement speed. In this manner, the movement of the tooth models may remain better synchronized to provide a flock control.

In other cases, though, the local control module of the tooth or other tooth models act to determine whether a way point was reached within a predefined time window with the tooth movement plan defining times for being at each way point relative to a start/go time. If not (e.g., the tooth model did not reach a way point at time "X" plus an allowable delay), the local control module may act to modify the tooth movement plan by directing the tooth model to skip the next way point and move directly to the way point within the mouth.

For example, a tooth movement plan may include way points A to Z. If a local control module determines that a predefined time window for way point C was not achieve, the local control module may skip or remove way point D from the tooth movement plan and cause the tooth model to take a direction/course (e.g., a straight line or other predefined path) to way point E. In this way, the tooth movement speed is maintained (e.g., all tooth models are moved at the same speed) while allowing the tooth model to "catch up" if they fall behind in their tooth movement plan (e.g., defining a set of way points to pass through or nearby within a predefined time period that may correspond with a time to perform a show/display or perform a task with the teeth).

With regard to safety and monitoring of operations, each tooth model may store a definition of a geofence that defines an outer perimeter (and an inner area in some cases) or boundary of a geographical area. The tooth models local control module compares the present position determined for the tooth model during a tooth movement and compares this position to the geofence. If this boundary is crossed (or is being approached such as within a preset distance from the geofence), the local control module may act to promptly return the tooth model back within the geofence boundaries. In other cases, the tooth model may be switched into a safe operating mode and this may cause the tooth model to return to a home position.

Further, regarding safe tooth model operations, some embodiments of tooth movement control may involve configuring the tooth models to have tooth model-to-model (or tooth-to-tooth) communications to avoid collisions without reliance upon the TMCS to intervene. Each tooth model may use its local control module to operate on an ongoing basis to detect when another tooth model comes within a predefined distance from the tooth model such as within a sphere of 1 to 3 mm or the like. The first tooth model to detect such a condition (or both tooth models if a tie) generates a collision warning message and transmits this message to the offending/nearby tooth model to alter its course or present position to move out of the first tooth models dental space. For example, the tooth model receiving such a collision warning message may store an evasive action in its memory and initiate this action (a fixed movement such as angling to the right or left a preset angle). The evasion may be taken for a preset time period and then the tooth model may return to following its tooth movement plan (e.g., recalculate a course to the next way point from its new present location or the like).

In another example, the tooth models local control module monitors the present orientation of the tooth model and if the orientation is outside an acceptable range (e.g., tip or rotate exceeds 320 degrees or the like for a tooth) or if the bodily movement is too much, the local control module may also act to enter the tooth model into a safe operating mode (before or after attempting to correct the operating problem).

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

As will be apparent, the features and attributes of the specific embodiments disclosed herein may be combined in different ways to form additional embodiments, all of which fall within the scope of the present disclosure.

Fabricating One or More Aligners

The system described herein is related to the fabrication of dental appliances such as retainers and aligners using three-dimensional (3D) printing processes. The appliance may be formed to have hollow shapes with complex geometries using tiny cells known as lattice structures. Topology optimization can be used to assist in the efficient blending of solid-lattice structures with smooth transitional material volume. Lattice performance can be studied under tension, compression, shear, flexion, torsion, and fatigue life.

Free-form lattice structures are provided herein, which fit at least part of the surface, e.g. external contour, of a body part. Specifically, the embodiments described may utilize free-form lattice structures for forming or fabricating appliances which are designed for placement or positioning upon the external surfaces of a patient's dentition for correcting one or more malocclusions. The free-form structure is at least partially fabricated by additive manufacturing techniques and utilizes a basic structure comprised of a lattice structure. The lattice structure may ensure and/or contribute to a free-form structure having a defined rigidity and the lattice structure may also ensure optimal coverage on the dentition by a coating material which may be provided on the lattice structure. The lattice structure is at least partly covered by, impregnated in, and/or enclosed by the coating material. Furthermore, embodiments of the lattice structure can contribute to the transparency of the structure.

The term "free-form lattice structure", as used herein, refers to a structure having an irregular and/or asymmetrical flowing shape or contour, more particularly fitting at least part of the contour of one or more body parts. Thus, in particular embodiments, the free-form structure may be a free-form surface. A free-form surface refers to an (essentially) two-dimensional shape contained in a three-dimensional geometric space. Indeed, as detailed herein, such a surface can be considered as essentially two-dimensional in that it has limited thickness, but may nevertheless to some degree have a varying thickness. As it comprises a lattice structure rigidly set to mimic a certain shape it forms a three-dimensional structure.

Typically, the free-form structure or surface is characterized by a lack of corresponding radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surfaces. Triangulated surfaces are used in Standard Triangulation Language (STL) files which are known to a person skilled in CAD design. The free-form structures fit the surface of a body part, as a result of the presence of a rigid basic structures therein, which provide the structures their free-form characteristics.

The term "rigid" when referring to the lattice structure and/or free-form structures comprising them herein refers to a structure showing a limited degree of flexibility, more particularly, the rigidity ensures that the structure forms and retains a predefined shape in a three-dimensional space prior to, during and after use and that this overall shape is mechanically and/or physically resistant to pressure applied thereto. In particular embodiments the structure is not foldable upon itself without substantially losing its mechanical integrity, either manually or mechanically. Despite the overall rigidity of the shape of the envisaged structures, the specific stiffness of the structures may be determined by the structure and/or material of the lattice structure. Indeed, it is envisaged that the lattice structures and/or free-form structures, while maintaining their overall shape in a three-dimensional space, may have some (local) flexibility for handling. As will be detailed herein, (local) variations can be ensued by the nature of the pattern of the lattice structure, the thickness of the lattice structure and the nature of the material. Moreover, as will be detailed below, where the free-form structures envisaged herein comprise separate parts (e.g. non-continuous lattice structures) which are interconnected (e.g., by hinges or by areas of coating material), the rigidity of the shape may be limited to each of the areas comprising a lattice structure.

Figure 11A:
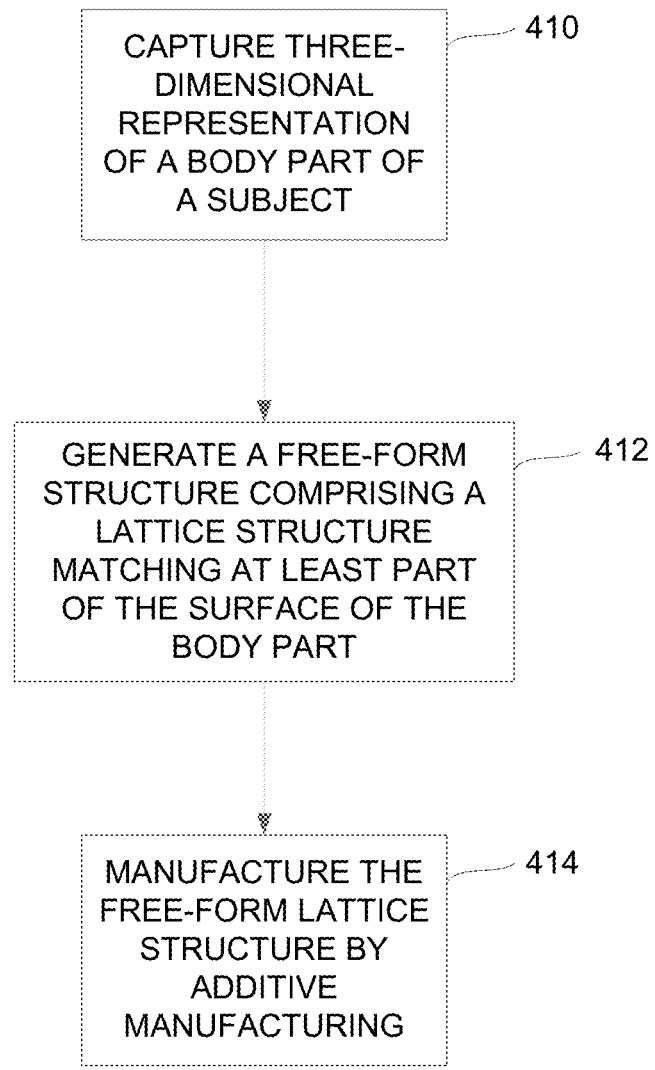
FIG. 11A shows an exemplary process for fabricating a dental appliance using a lattice structure.

Generally, the methods envisaged herein are for dental appliance fabrication processes where the fabrication process includes designing an appliance worn on teeth to be covered by a free-form structure, manufacturing the mold, and providing the (one or more) lattice structures therein and providing the coating material in the mold so as to form the free-form structure. The free-form structures are patient-specific, i.e. they are made to fit specifically on the anatomy or dentition of a certain patient, e.g., animal or human. FIG. 11A generally shows an overall exemplary method for fabricating a dental appliance by capturing a 3D representation of a body part of a subject 410. In this example, this may involve capturing the 3D representation of the surfaces, e.g. external contours, of a patient's dentition for correcting one or more malocclusions. For this purpose, the subject may be scanned using a 3D scanner, e.g. a hand-held laser scanner, and the collected data can then be used to construct a digital, three dimensional model of the body part of the subject. Alternatively, the patient-specific images can be provided by a technician or medical practitioner by scanning the subject or part thereof. Such images can then be used as or converted into a three-dimensional representation of the subject, or part thereof. Additional steps wherein the scanned image is manipulated and for instance cleaned up may be envisaged.

With the captured 3D representation, a free-form structure comprised generally of a lattice structure matching at least part of the surface of the body part, e.g., dentition, may be generated 412. Designing a free-form structure based on said three dimensional representation of said body part, such that the structure is essentially complementary to at least part of said body part and comprises or consists of a lattice structure. In the lattice structure, one or more types and/or sizes of unit cell may be selected, depending on the subject shape, the required stiffness of the free-form structure, etc. Different lattice structures may be designed within the free-form structure for fitting on different locations on the body part. The different lattice structures may be provided with, e.g., a hinge or other movable mechanism, so that they can be connected and/or, can be digitally blended together or connected by beams in the basic structure to form a single part.

This step may also include steps required for designing the lattice structure, including for instances of defining surfaces on the positive print of the mask that may need different properties, different cell sizes and/or openings, generating the cells with the required geometry and patterning them as needed on the defined surfaces to cover said surfaces, and combining the separate cell patterns into a single solid part. It should be noted that the requirements of the lattice structure would be clear to a skilled person while designing the lattice structure. The skilled person will therefore use data obtained from his own experience as well as data from numerical modeling systems, such as FE and/or CFD models.

The free-form lattice structure may then be actually manufactured, e.g., by additive manufacturing methods 414. In certain embodiments, this may include providing a coating material on the basic structure in which coating material is preferably a polymer. These different steps need not be performed in the same location or by the same actors. Indeed typically, the design of the free-form structure, the manufacturing and the coating may be accomplished in different locations by different actors. Moreover, it is envisaged that additional steps may be performed between the steps recited above. In coating or impregnating the free-form basic structure, the lattice structure may be impregnated with a certain material, such as a polymer, thereby generating the free-form structure. This may include steps such as adding the polymeric material or other material into the dental appliance, curing the material impregnating the lattice structure and disassembling the dental appliance.

After manufacturing the free-form structure, the structure may go through a number of post-process steps including for instance cleaning up and finishing the free-form structure. Moreover, other applications of forming a rigid free-form structure as described herein may also include applications for, but not limited to, therapeutic, cosmetic and protective applications.

In one particular application, the use of the free-form structures described herein may be used in the care and treatment of damaged skin surfaces, such as burn wounds. In further embodiments, the use of the free-from structures described herein may be used in the care, protection, and treatment of undamaged skin surfaces. According to additional particular embodiments, the use of a free-form structure as described herein may be used for cosmetic purposes. In further embodiments, the use of a free-form structure as described herein may be used for the delivery of treatment agents to the skin. In other particular embodiments, the structure further comprises one or more therapeutic compositions which may be embedded in the coating material. In yet further embodiments, the use of the structures described herein may be used as prosthetic devices, e.g., for replacing a body part, where the free-forms structure may be made to be identical to the missing body part.

Figure 11B:
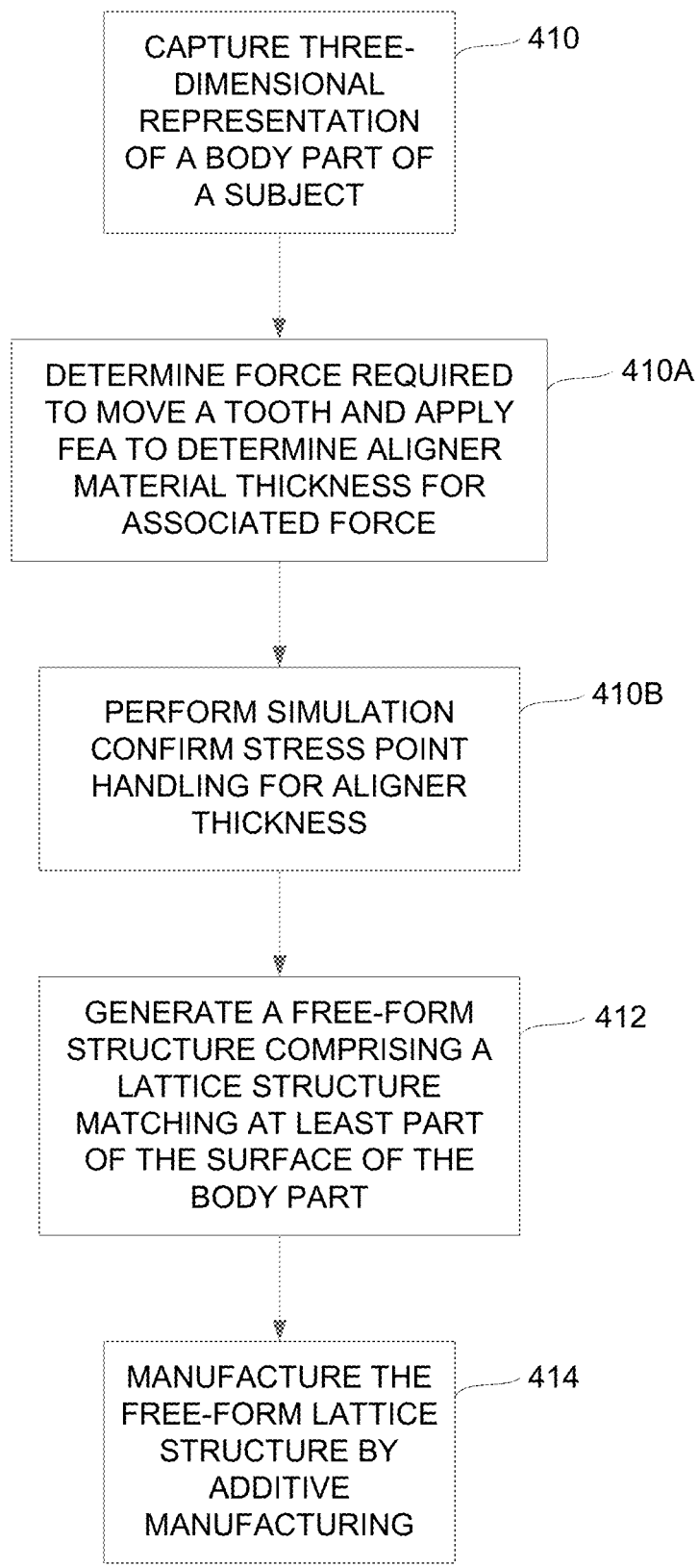
FIG. 11B shows an exemplary process for fabricating a dental appliance with varying material thickness using a lattice structure.

FIG. 11B shows another overall exemplary process for fabricating a dental appliance having a lattice structure similarly to that shown above in FIG. 11A. In this example, once the 3D representation has been captured 410, the amount of force required to move a tooth or teeth may be determined and finite element analysis may be utilized to determine an appropriate thickness of aligner material needed for the associated force 410A to move a particular tooth or teeth. In this manner, one or more oral appliances may be fabricated with varying material thicknesses in which regions which may not require much force are fabricated to have a relatively thinner region while regions of the appliance which may require a greater amount of force to move the tooth or teeth may be fabricated to have relatively thicker regions of material to create an oral appliance having directional strength (Differential Force) depending on the particular forces needed to correct particular malocclusions. Simulations may be performed on the modeled dentition (or aligners) to confirm stress point handling for the various aligner thicknesses 410B.

Then as previously described, a free-form structure comprised generally of a lattice structure matching at least part of the surface of the body part, e.g., dentition, may be generated 412 and the free-form lattice structure may then be actually manufactured, e.g., by additive manufacturing methods 414. However, the one or more oral appliances may be fabricated to have regions of relatively thickened and/or thinned material to accommodate the directional strength (Differential Force) of the oral appliances, as described in further detail below.

FIG. 12 shows a perspective view of an exemplary oral appliance 420 having two parts 422 (for the upper dentition and lower dentition). As shown, the oral appliance 420 generally includes a lattice structure 424 which can be used in a process for manufacturing the final oral appliance. In the process, the lattice structure 424 may first be 3D printed in a shape which approximates the oral appliance to be fabricated for correcting the malocclusion and the lattice structure may be positioned within a dental appliance 426, 426'. Then, the dental appliance 426, 426' containing the formed lattice structure 424 may be filled with the impregnating material 428, e.g., polymer or other materials described herein. After setting of the impregnating material 428, the dental appliance halves 426, 426' are removed to yield the coated oral appliance 420.

While the entire lattice structure 424 may be coated or impregnated by the impregnating material 428, only portions of the lattice structure 424 may be coated or particular surfaces of the lattice structure 424 may be coated while leaving other portions exposed. Variations of these embodiments are described in further detail below with respect to the oral appliance 420 shown in FIG. 12.

As can be appreciated, an approach to 3D printed progressive aligners of varying and/or increasing thickness has certain advantages. For example, the rate of incremental increase in thickness may not be dependent on standard thicknesses of sheet plastic available as an industrial commodity. An optimal thickness could be established for the 3D printing process. For example, rather than being limited to the, e.g., 0.040, 0.060 and 0.080 in. thickness sequence, a practitioner such as an orthodontist could choose a sequence such as, e.g., 0.040, 0.053 and 0.066 in. thickness, for an adult patient whose teeth are known to reposition more slowly compared to a rapidly growing adolescent patient.

Given the concept that an aligner formed from thinner material generates generally lower corrective forces than an identically configured aligner formed from thicker material, it follows that an aligner could be 3D printed so as to be thicker in areas where higher forces are needed and thinner in areas where lighter forces are needed. Having the latitude to produce aligners with first a default thickness and then areas of variable thickness could be favorably exploited to help practitioners address many difficult day-to-day challenges. For example, any malocclusion will consist of teeth that are further from their desired finished positions than other teeth. Further, some teeth are smaller than others and the size of the tooth corresponds to the absolute force threshold needed to initiate tooth movement. Other teeth may seem to be more stubborn due to many factors including the proximity of the tooth's root to the boundaries between cortical and alveolar bony support. Still other teeth are simply harder to correctively rotate, angulate, or up-right than others. Still other teeth and groups of teeth may need to be bodily moved as rapidly as possible over comparatively large spans to close open spaces. For at least such reasons, the option of tailoring aligner thickness and thus force levels around regions containing larger teeth or teeth that are further from their desired destinations, or those stubborn teeth allows those selected teeth to receive higher forces than small, nearly ideally positioned teeth.

The free-form lattice structure for the dental appliances can be at least partially fabricated by additive manufacturing (AM). More particularly, at least the basic structure may be fabricated by additive manufacturing using the lattice structure. Generally, AM can may include a group of techniques used to fabricate a tangible model of an object typically using 3D computer aided design (CAD) data of the object. A multitude of AM techniques are available for use, e.g., stereolithography, selective laser sintering, fused deposition modeling, foil-based techniques, etc. Selective laser sintering uses a high power laser or another focused heat source to sinter or weld small particles of plastic, metal, or ceramic powders into a mass representing the 3D object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680, which is incorporated herein by reference in its entirety and for any purpose. Foil-based techniques fix coats to one another by use of, e.g., gluing or photo polymerization or other techniques, and then cuts the object from these coats or polymerize the object. Such a technique is described in U.S. Pat. No. 5,192,539, which is incorporated herein by reference in its entirety and for any purpose.

Typically AM techniques start from a digital representation of the 3D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3D object may be generated using a computer system and computer aided design and manufacturing (CAD/CAM) software.

The basic structure comprising the lattice structure may thus be made of any material which is compatible with additive manufacturing and which is able to provide a sufficient stiffness to the rigid shape of the regions comprising the lattice structure in the free-form structure or the free-form structure as a whole. Suitable materials include, but are not limited to, e.g., polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, etc.

The lattice structure itself may be comprised of a rigid structure which has an open framework of, e.g., 3D printed lattices. Lattice structures may contain a plurality of lattices cells, e.g., dozens, thousands, hundreds of thousands, etc. lattice cells. Once the 3D model of the dentition is provided, the process may generate STL files to print the lattice version of the 3D model and create support structures where necessary. The system identifies where material is needed in an appliance and where it is not required, prior to placing and optimizing the lattice.

The system may optimize dental lattices in two phases. First, it applies a topology optimization allowing more porous materials with intermediate densities to exist. Second, the porous zones are transformed into explicit lattice structures with varying material volume. In the second phase, the dimensions of the lattice cells are optimized. The result is a structure with solid parts plus lattice zones with varying volumes of material. The system balances the relationship between material density and part performance, for example, with respect to the stiffness to volume ratio, that can impact design choices made early in the product development process. Porosity may be especially important as a functional requirement for biomedical implants. Lattice zones could be important to the successful development of products where more than mere stiffness is required. The system can consider buckling behavior, thermal performance, dynamic characteristics, and other aspects, all of which can be optimized. The user may manipulate material density based upon the result of an optimization process, comparing stronger versus weaker, or solid versus void versus lattice, designs. The designer first defines the objective, then performs optimization analysis to inform the design.

While 3D printing may be used, the lattices can also be made of strips, bars, girders, beams or the like, which are contacting, crossing or overlapping in a regular pattern. The strips, bars, girders, beams or the like may have a straight shape, but may also have a curved shape. The lattice is not necessarily made of longitudinal beams or the like, and may for example consist of interconnected spheres, pyramids, etc. among others.

Figure 12A:
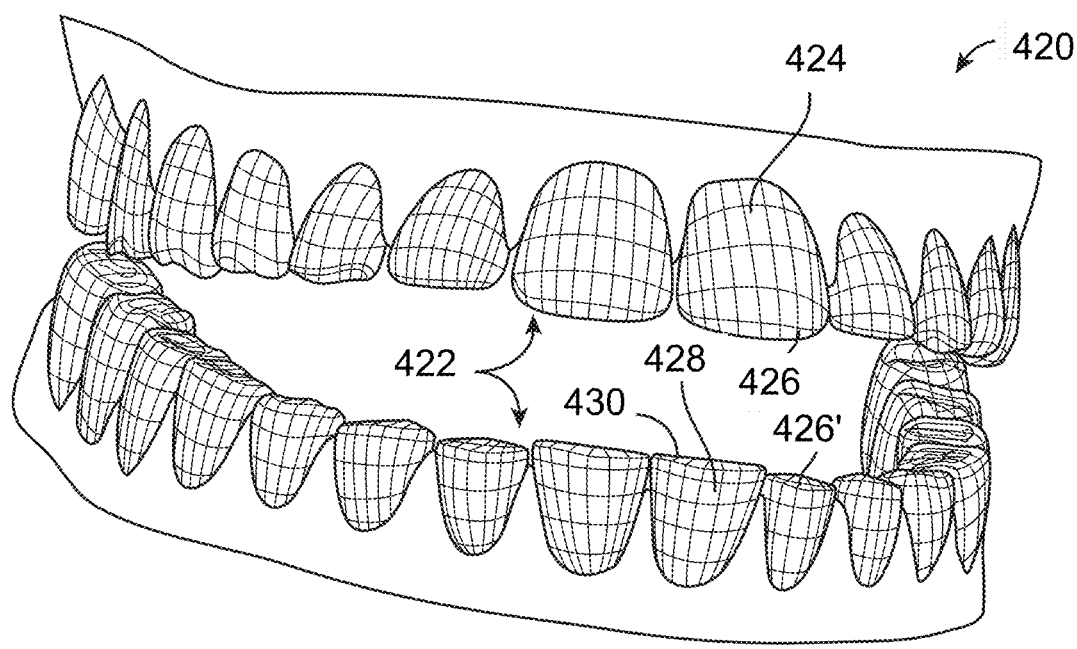
FIG. 12A shows a perspective view of an example of a basic structure formed into a bottom half and a top half for a dental appliance utilizing a lattice structure which may be used in a 3D printing process.
Figure 12B:
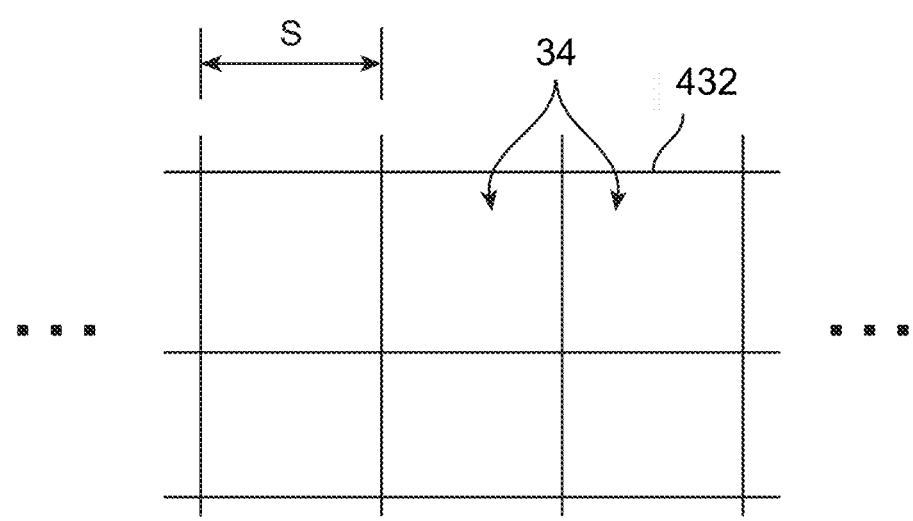
FIG. 12B shows a detail exemplary view of the openings in a lattice structure.

The lattice structure is typically a framework which contains a regular, repeating pattern as shown in FIG. 12A, wherein the pattern can be defined by a certain unit cell. A unit cell is the simplest repeat unit of the pattern. Thus, the lattice structure 424 is defined by a plurality of unit cells. The unit cell shape may depend on the required stiffness and can for example be triclinic, monoclinic, orthorhombic, tetragonal, rhombohedral, hexagonal or cubic. Typically, the unit cells of the lattice structures have a volume ranging from, e.g., 1 to 8000 mm$^3$, or preferably from 8 to 3375 mm$^3$, or more preferably from 64 to 3375 mm$^3$, or most preferably from 64 to 1728 mm$^3$. The unit cell size may determine, along with other factors such as material choice and unit cell geometry, the rigidity (stiffness) and transparency of the free-form structure. Larger unit cells generally decrease rigidity and increase transparency, while smaller unit cells typically increase rigidity and decrease transparency. Local variations in the unit cell geometry and/or unit cell size may occur, in order to provide regions with a certain stiffness. Therefore, the lattice 424 may comprise one or more repeated unit cells and one or more unique unit cells. In order to ensure the stability of the lattice structure 424, the strips, bars, girders, beams or the like may have a thickness or diameter of, e.g., 0.1 mm or more. In particular embodiments, the strips, bars, girders, beams or the like may preferably have a thickness or diameter of, e.g., 0.2 mm, 0.4 mm, 0.6 mm, 0.8 mm, 1 mm, 1.5 mm, 2 mm, 3 mm, 5 mm or more. The main function of the lattice structure 424 is to ensure a certain stiffness of the free-form structure. The lattice structure 424 may further enhance or ensure transparency, as it is an open framework. The lattice structure 424 can preferably be considered as a reticulated structure having the form and/or appearance of, e.g., a net or grid, although other embodiments may be used.

The stiffness of the lattice structure depends on factors such as the structure density, which depends on the unit cell geometry, the unit cell dimensions and the dimensions of the strips, bars, girders, beams, etc. of the framework 432. Another factor is the distance, S, between the strips and the like, or in other words, the dimensions of the openings in the lattice structure, as shown in the detail exemplary view of FIG. 12B. Indeed, the lattice structure is an open framework and therefore comprises openings 434. In particular embodiments, the opening size S of the lattice structure is between, e.g., 1 and 20 mm, between 2 and 15 mm, or between 4 and 15 mm. In preferred embodiments, the opening size is between, e.g., 4 and 12 mm. The size of the openings may be the equal to or smaller than the size of the unit cell 434 while in other embodiments, the openings may be uniform in size or arbitrary in size. In yet another alternative, differing regions of the lattice may have openings which are uniform in size but which are different from other regions.

Figure 12C:
FIG. 12C shows an exemplary end view of a lattice structure having several reticulated layers.

In particular embodiments, the free-form structures may comprise a lattice structure having one or more interconnected reticulated layers, as shown in the exemplary end view of FIG. 12C. For instance, the lattice structure may comprise one, two, three or more reticulated layers 438, where the structure comprises different at least partially superimposed and/or interconnected layers 436, 436', 436" within the lattice structure. The degree of stiffness provided by the lattice structure may increase with the number of reticulated layers provided therein. In further particular embodiments, the free-form structures may comprise more than one lattice structure. The examples shown are merely illustrative of the different embodiments.

For certain applications the lattice structure may further comprise one or more holes with a larger size than the openings or unit cells as described hereinabove. Additionally or alternatively, the lattice structure may not extend over the entire shape of the free-form structure such that openings in the structure or regions for handling, e.g., tabs or ridges, and/or regions of unsupported coating material are formed. An example of such an application is a facial mask, where holes are provided at the location of the eyes, mouth and/or nose holes. Typically, these latter holes are also not filled by the coating material.

Similarly, in particular embodiments, the size of the openings which are impregnated in and/or enclosed by the adjoining material may range between, e.g., 1 and 20 mm. The holes in the lattice structure (corresponding to holes in the free-form structure) as described herein will also typically have a size which is larger than the unit cell. Accordingly, in particular embodiments, the unit cell size ranges between, e.g., 1 and 20 mm.

Figure 12D:
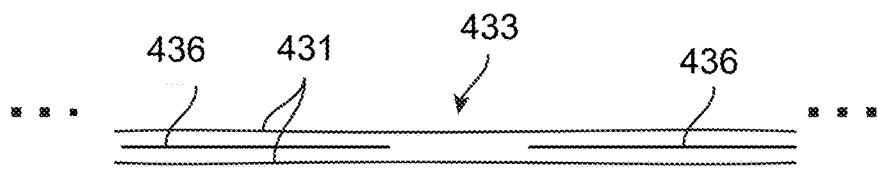
FIG. 12D shows an exemplary end view of a lattice structure having regions comprised only of the coating material.

According to particular embodiments, as shown in the end view of FIG. 12D, the envisaged free-form structure may contain regions 433 comprised only of the coating material 431. This may be of interest in areas where extreme flexibility of the free-form structure is desired.

Figure 12E:
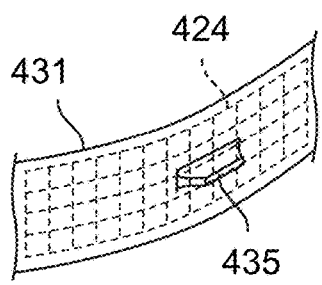
FIG. 12E shows a detail perspective view of a lattice structure and coating having a feature such as an extension formed from the surface.
Figure 12F:
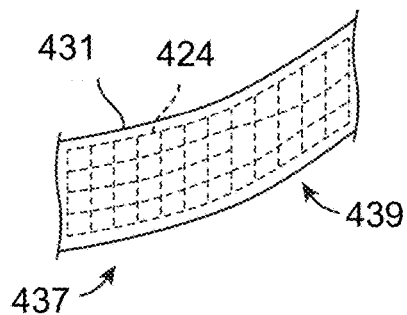
FIG. 12F shows a detail perspective view of a lattice structure and coating having different regions with varying unit cell geometries.

In particular embodiments, the envisaged free-form structure may comprise a basic structure which contains, in addition to a lattice structure, one or more limited regions which do not contain a lattice structure, but are uniform surfaces, as shown in the detail perspective view of FIG. 12E. Typically these form extensions 435 from the lattice structure with a symmetrical shape (e.g. rectangular, semi-circle, etc.). Such regions, however, typically encompass less than, e.g., 50%, or more particularly less than, e.g., 30%, or most particularly less than, e.g., 20% of the complete basic structure. Typically they are used as areas for handling (manual tabs) of the structure and/or for placement of attachment structures (clips, elastic string, etc.). In particular embodiments, the basic structure may be comprised essentially of only a lattice structure.

Figure 12G:
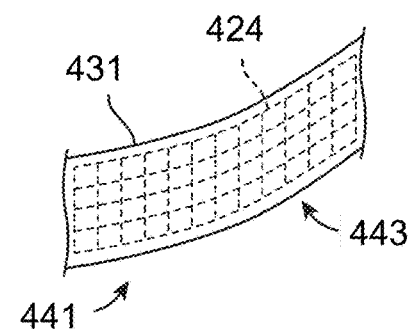
FIG. 12G shows a detail perspective view of a lattice structure and coating having different regions formed with different thicknesses.
Figure 12H:
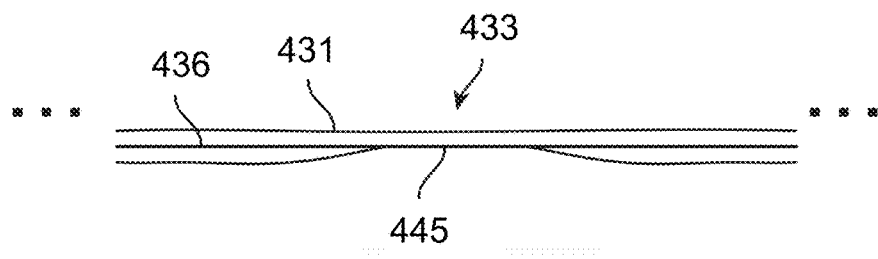
FIG. 12H shows an exemplary end view of a lattice structure having regions with a coating on a single side.

It can be advantageous for the dental appliance structure to have certain regions with a different stiffness (such as in the molar teeth to provide added force). This can be achieved by providing a lattice structure with locally varying unit cell geometries, varying unit cell dimensions and/or varying densities and/or varying thicknesses of the lattice structure (by increasing the number of reticulated layers), as shown in the exemplary detail perspective view of FIG. 12F. Accordingly, in particular embodiments, the lattice structure is provided with varying unit cell geometries, varying unit cell dimensions, varying lattice structure thicknesses and/or varying densities 437, 439. Additionally or alternatively, as described herein, the thickness of the coating material may also be varied, as shown in FIG. 12G. Thus, in particular embodiments, the free-form structure has a varying thickness with a region of first thickness 441 and a region of second thickness 443. In further particular embodiments, the free-form structures may have regions with a different stiffness, while they retain the same volume and external dimensions.

In particular embodiments of the free-form structures, the basic structure or the lattice structure can be covered in part with a coating material which is different from the material used for manufacturing the lattice structure. In particular embodiments the lattice structure is at least partly embedded within or enclosed by (and optionally impregnated with) the coating material, as shown in the exemplary detail end view of FIG. 12H. In further embodiments, the coating material is provided onto one or both surfaces of the lattice structure 436. In particular embodiments only certain surface regions of the basic structure and/or the lattice structure in the free-form structure are provided with a coating material while portions may be exposed 445. In particular embodiments, at least one surface of the basic structure and/or lattice structure may be coated 431 for at least 50%, more particularly at least 80%. In further embodiments, all regions of the basic structure having a lattice structure are fully coated, on at least one side, with the coating material. In further particular embodiments, the basic structure is completely embedded with the coating material, with the exceptions of the tabs provided for handling.

In further embodiments, the free-form structure comprises, in addition to a coated lattice structure, regions of coating material not supported by a basic structure and/or a lattice structure.

Accordingly, in particular embodiments, the free-form structure may comprise at least two materials with different texture or composition. In other embodiments, the free-form structure may comprise a composite structure, e.g., a structure which is made up of at least two distinct compositions and/or materials.

The coating material(s) may be a polymeric material, a ceramic material and/or a metal. In particular embodiments, the coating material(s) is a polymeric material. Suitable polymers include, but are not limited to, silicones, a natural or synthetic rubber or latex, polyvinylchloride, polyethylene, polypropylene, polyurethanes, polystyrene, polyamides, polyesters, polyepoxides, aramides, polyethyleneterephthalate, polymethylmethacrylate, ethylene vinyl acetate or blends thereof. In particular embodiments, the polymeric material comprises silicone, polyurethane, polyepoxide, polyamides, or blends thereof.

In particular embodiments the free-form structures comprise more than one coating material or combinations of different coating materials.

In specific embodiments, the coating material is a silicone. Silicones are typically inert, which facilitates cleaning of the free-form structure.

In particular embodiments, the coating material is an optically transparent polymeric material. The term "optically transparent" as used herein means that a layer of this material with a thickness of 5 mm can be seen through based upon unaided, visual inspection. Preferably, such a layer has the property of transmitting at least 70% of the incident visible light (electromagnetic radiation with a wavelength between 400 and 760 nm) without diffusing it. The transmission of visible light, and therefore the transparency, can be measured using a UV-Vis Spectrophotometer as known to the person skilled in the art. Transparent materials are especially useful when the free-form structure is used for wound treatment (see further). The polymers may be derived from one type of monomer, oligomer or prepolymer and optionally other additives, or may be derived from a mixture of monomers, oligomers, prepolymers and optionally other additives. The optional additives may comprise a blowing agent and/or one or more compounds capable of generating a blowing agent. Blowing agents are typically used for the production of a foam.

Accordingly, in particular embodiments, the coating material(s) are present in the free-form structure in the form of a foam, preferably a foamed solid. Thus, in particular embodiments, the lattice structure is coated with a foamed solid. Foamed materials have certain advantages over solid materials: foamed materials have a lower density, require less material, and have better insulating properties than solid materials. Foamed solids are also excellent impact energy absorbing materials and are therefore especially useful for the manufacture of free-form structures which are protective elements (see further). The foamed solid may comprise a polymeric material, a ceramic material or a metal. Preferably, the foamed solid comprises one or more polymeric materials.

The foams may be open cell structured foams (also known as reticulated foams) or closed cell foams. Open cell structured foams contain pores that are connected to each other and form an interconnected network which is relatively soft. Closed cell foams do not have interconnected pores and are generally denser and stronger than open cell structured foams. In particular embodiments, the foam is an "integral skin foam", also known as "self-skin foam", e.g., a type of foam with a high-density skin and a low-density core.

Thus in particular embodiments, free-form structures may comprise a basic structure which includes a lattice structure which is at least partially coated by a polymeric or other material as described herein. For some applications, the thickness of the coating layer and the uniformity of the layer thickness of the coating are not essential. However, for certain applications, it can be useful to provide a layer of coating material with an adjusted layer thickness in one or more locations of the free-form structure, for example, to increase the flexibility of the fit of the free-form structure on the body part.

Figure 12I:
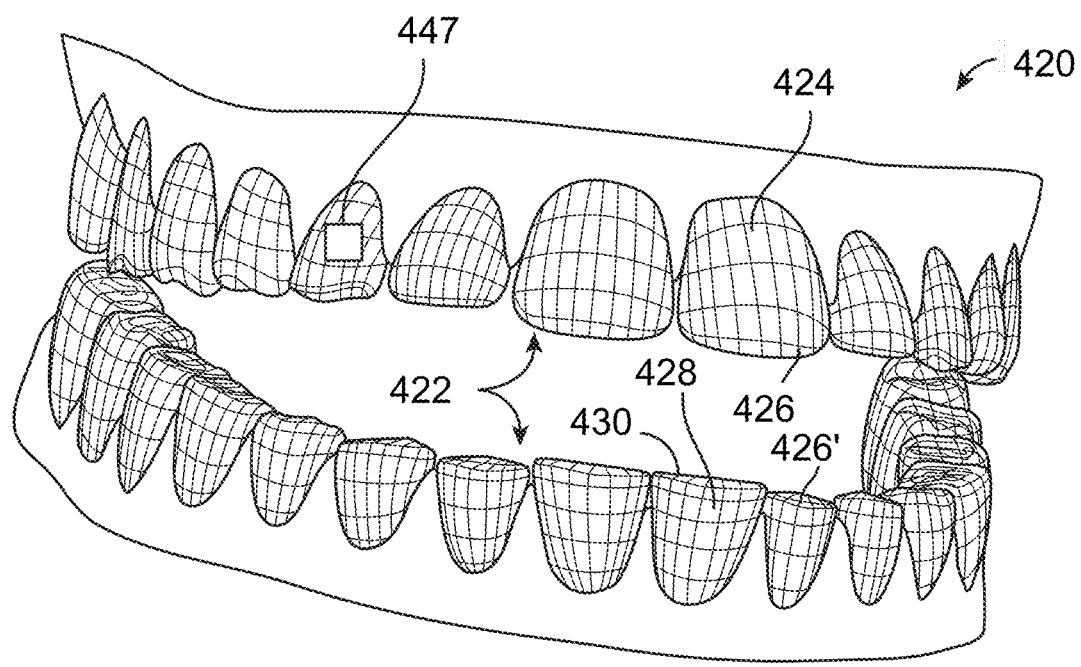
FIG. 12I shows a perspective view of an aligner having at least one additional component integrated.
Figure 12J:
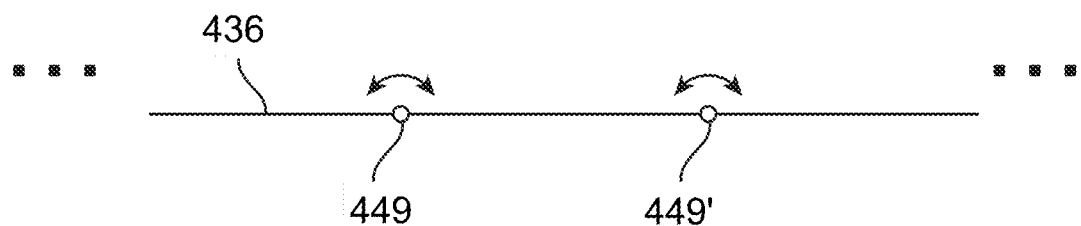
FIG. 12J shows an exemplary end view of a lattice structure a hinge or other movable mechanism integrated along the lattice.

The basic structure of the freeform structures envisaged herein can be made as a single rigid free-form part which does not need a separate liner or other elements. Independent thereof it is envisaged that the free-form structures can be further provided with additional components 447 such as sensors, straps, or other features for maintaining the structure in position on the body, or any other feature that may be of interest in the context of the use of the structures and integrated within or along the structure, as shown in FIG. 12I. Various examples of sensors which may be integrated are described in further detail herein.

In certain embodiments, the free-form structure comprises a single rigid lattice structure (optionally comprising different interconnected layers of reticulated material). However, such structures often only allow a limited flexibility, which may cause discomfort to a person or animal wearing the free-form structure. An increase in flexibility can be obtained if the free-form structure comprises two or more separate rigid lattice structures which can move relative to each other. These two or more lattice structures are then enclosed by a material as described above, such that the resulting free-form structure still is made or provided as a single part. The rigidity of the shape of the free-form structure is ensured locally by each of the lattice structures, while additional flexibility during placement is ensured by the fact that there is a (limited) movement of the lattice structures relative to each other. Indeed, in these embodiments, the coating material and/or a more limited lattice structure) will typically ensure that the lattice structures remain attached to each other.

In particular embodiments, the lattice structures are partially or completely overlapping. However, in particular embodiments, the different lattice structures are non-overlapping. In further particular embodiments, the lattice structures are movably connected to each other, for example via a hinge or other movable mechanism 449, 449', as shown in the detail end view of FIG. 12J. In particular embodiments the connection is ensured by lattice material. In further particular embodiments the lattice structures may be interconnected by one or more beams which form extensions of the lattice structures. In further embodiments the lattice structures are held together in the free-form structure by the coating material. An example of such a free-form structure is a facial mask with a jaw structure that is movable with respect to the rest of the mask. Accordingly, in particular embodiments, the lattice structure comprises at least two separate lattice structures movably connected to each other, whereby the lattice structures are integrated into the free-form structure, as shown.

The free-form structure may be used for wound treatment as described herein. For optimal healing, the free-form structure provides a uniform contact and/or pressure on the wound site or specific locations of the wound site. The lattice structure makes it simple to incorporate pressure sensors into the free-form structure according to the present invention. The sensors can be external sensors, but may also be internal sensors. Indeed, the lattice structure can be designed such that it allows mounting various sensors at precise locations, as described above, before impregnating and/or enclosing the lattice structure by a polymer or other material.

Additionally or alternatively, the free-form structure may comprise one or more other sensors, as described above in FIG. 12I, such as a temperature sensor, a moisture sensor, an optical sensor, a strain gauge, an accelerometer, a gyroscope, a GPS sensor, a step counter, etc. Accelerometers, gyroscopes, GPS sensors and/or step counter may for example be used as an activity monitor. Temperature sensor(s), moisture sensor(s), strain gauge(s) and/or optical sensor(s) may be used to monitor the healing process during wound treatment. Specifically, the optical sensor(s) may be used to determine collagen fiber structure as explained in US Pat. App. 2011/0015591, which is hereby incorporated by reference in its entirety and for any purpose.

Accordingly, in particular embodiments the free-form structure further comprises one or more external and/or internal sensors. In specific embodiments, the free-form structure comprises one or more internal sensors. In certain embodiments, the free-form structure comprises one or more pressure and/or temperature sensors.

The skilled person will understand that in addition to the sensor(s), also associated power sources and/or means for transmitting signals from the sensor(s) to a receiving device may be incorporated into the free-form structure, such as wiring, radio transmitters, infrared transmitters, and the like.

In particular embodiments, at least one sensor may comprise micro-electronic mechanical systems (MEMS) technology, e.g., technology which integrates mechanical systems and micro-electronics. Sensors based on MEMS technology are also referred to as MEMS-sensors and such sensors are small and light, and consume relatively little power. Non-limiting examples of suitable MEMS-sensors are the STTS751 temperature sensor and the LIS302DL accelerometer STMicroelectronics.

Figure 12K:
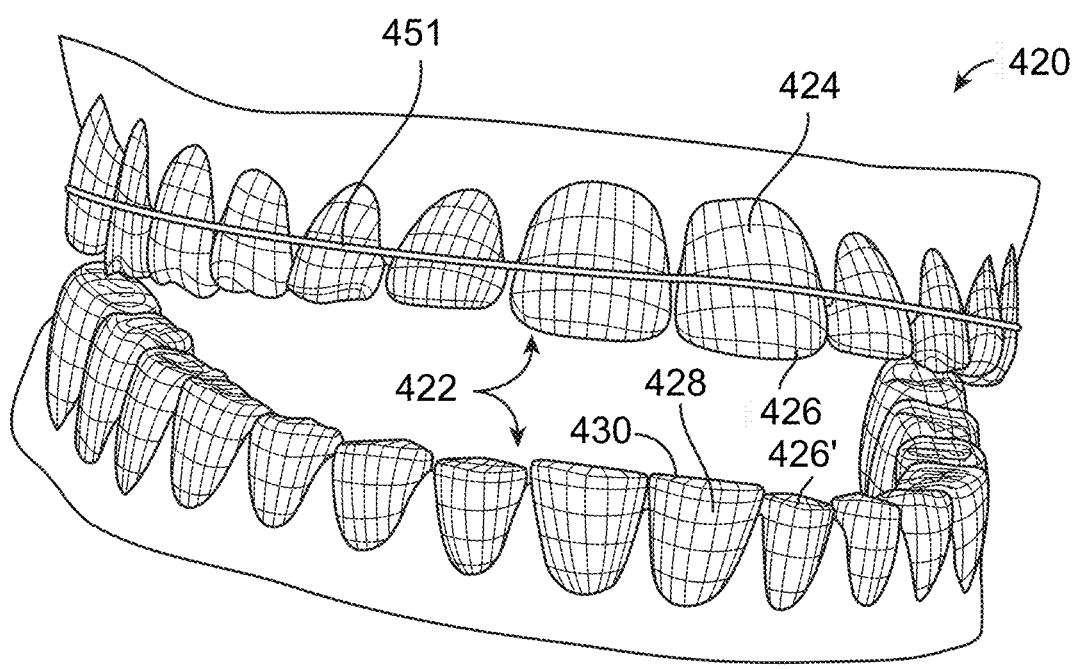
FIG. 12K shows a perspective view of an aligner having one or more (internal) channels integrated.

As shown in FIG. 12K, the lattice structure also allows providing the free-form structure with one or more (internal) channels 451. These channels may be used for the delivery of treatment agents to the underlying skin, tissue, or teeth. The channels may also be used for the circulation of fluids, such as heating or cooling fluids.

One philosophy of orthodontic treatment is known as "Differential Force" called out for the corrective forces directed to teeth to be closely tailored according to the ideal force level requirements of each tooth. The Differential Force approach was supported by hardware based on calibrated springs intended to provide only those ideal force levels required. Carrying the concepts of the Differential Force approach forward to the precepts of aligner fabrication, one can appreciate that CNC-machined aligners exhibiting carefully controlled variable thickness can accomplish the Differential Force objectives on a tooth-by-tooth basis. The compartments surrounding teeth can have wall thicknesses established at the CAD/CAM level by a technician based on the needs of each tooth. A 3D printed aligner can have a limitless series of regions, each with a unique offset thickness between its inner and outer surfaces.

Figure 13:
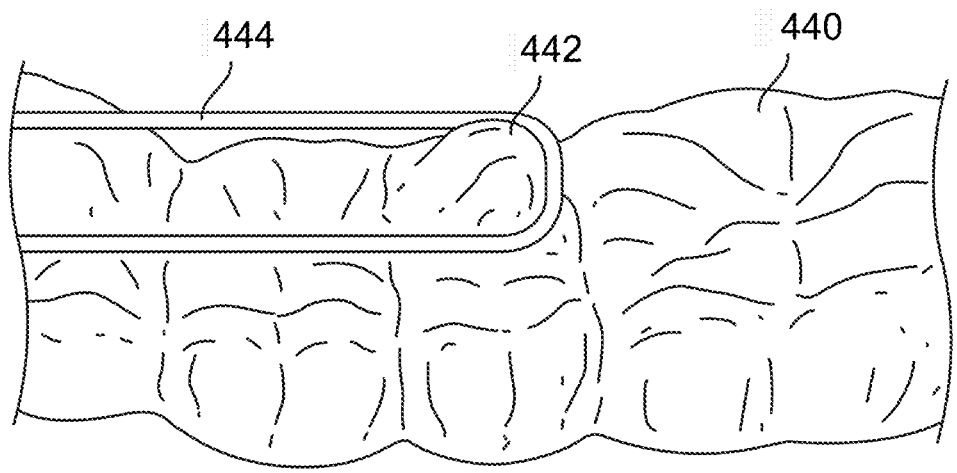
FIG. 13 shows a perspective detail view of a portion of an aligner having an area that is machined to have a relatively thicker material portion to accept an elastic.

Prior to installing such devices, a practitioner may assess the progress of a case at mid-treatment for example and in particular, make note of problem areas where the desired tooth response is lagging or instances where particular teeth are stubbornly not moving in response to treatment forces. The 3D printed structure can include a group of small devices that are intended to be strategically positioned and 3D printed with an aligner's structure. Such devices are termed "aligner auxiliaries." FIG. 13 is a detail view of a portion of an aligner 440 showing a 3D printed area 442 that is machined allowing thicker material to accept an elastic 444. Other 3D printed geometries of interest would be divots or pressure points, creating openings/windows on the aligner for a combination treatment, e.g., forming hooks on the aligner for elastic bands, among others. Aligner auxiliaries may be installed in those locations to amplify and focus corrective forces of the aligner to enhance correction. For example, an auxiliary known as a tack can be installed after a hole of a predetermined diameter is pierced through a wall of a tooth-containing compartment of an aligner. The diameter of the hole may be slightly less than the diameter of a shank portion of the tack which may be printed directly on the aligner. Such progressively-sized tacks and other auxiliary devices are commercially available to orthodontists who use them to augment and extend the tooth position correcting forces of aligners.

Figures 14A, 14B:
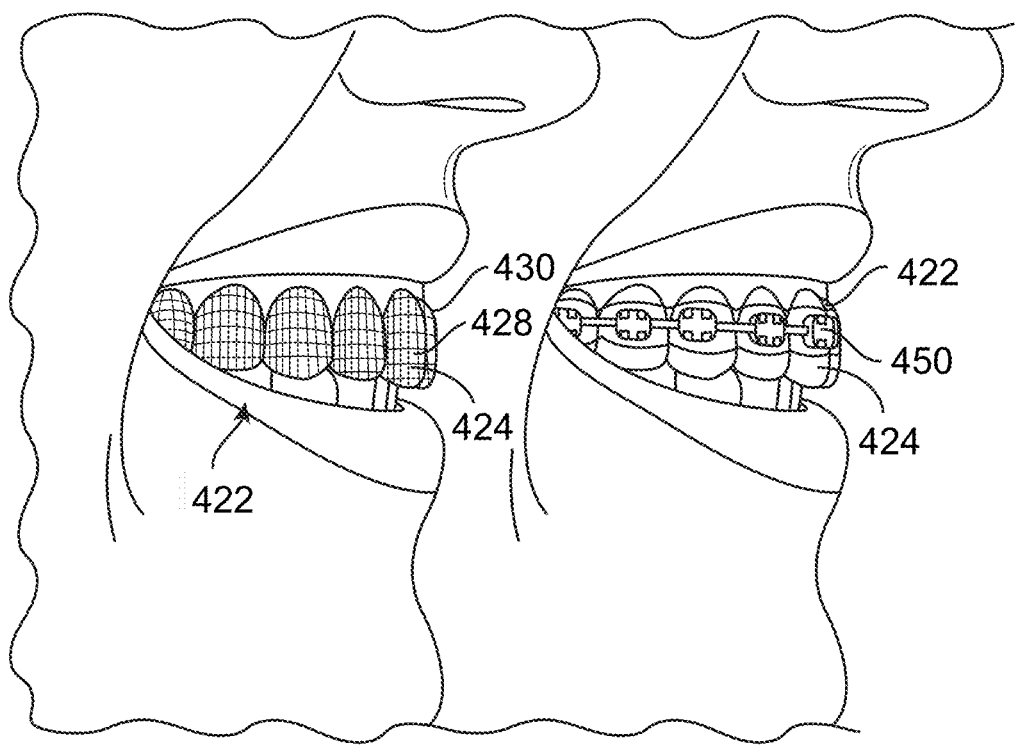
FIGS. 14A and 14B illustrate a variation of a free-form dental appliance structure having a relatively rigid lattice structure and one or more features for use as a dental appliance or retainer.

Bumps can also be used and serve to focus energy stored locally in the region of the aligner's structure adjacent to a bump. The inward-projecting bump causes an outward flexing of the aligner material in a region away from the tooth surface. Configured in this way, bumps gather stored energy from a wider area and impinge that energy onto the tooth at the most mechanically advantageous point, thus focusing corrective forces most efficiently. An elastic hook feature 450 can be 3D printed directly in an otherwise featureless area of an aligner's structure, as shown in the side views of FIGS. 14A and 14B. Elastic hooks may also be used as anchor points for orthodontic elastics that provide tractive forces between sectioned portions of an aligner (or an aligner and other structures fixedly attached to the teeth) as needed during treatment.

Figure 14C:
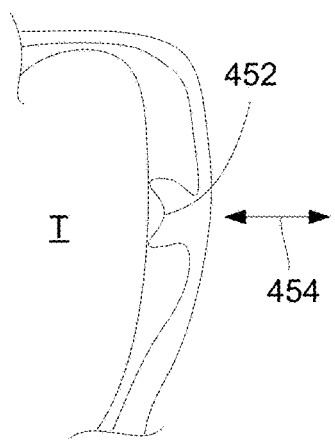
FIG. 14C shows a partial cross-sectional view of a suction feature fabricated to adhere to one or more particular teeth.

Aside from hook features 450, other features such as suction features 452 may be fabricated for adherence to one or more particular teeth T, as shown in the partial cross-sectional view of FIG. 14C. In this manner, the aligner may exert a directed force 454 concentrated on the one or more particular teeth.

Figure 14D:
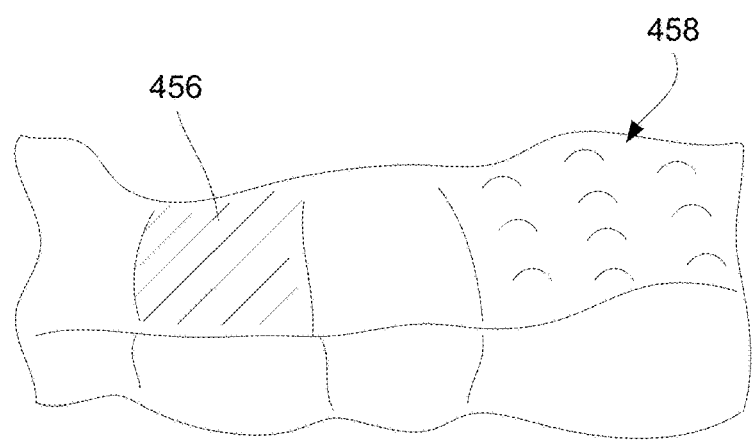
FIG. 14D shows a perspective view of a portion of the aligner having regions configured to facilitate eating or talking by the patient.

In yet another embodiment, as shown in the perspective view of FIG. 14D, the occlusal surfaces of the aligner may be fabricated to have areas defined to facilitate eating or talking by the patient. Such features may include occlusal regions which are thinned, made into flattened surfaces 456, or made with any number of projections 458 to facilitate eating.

Figure 14E:
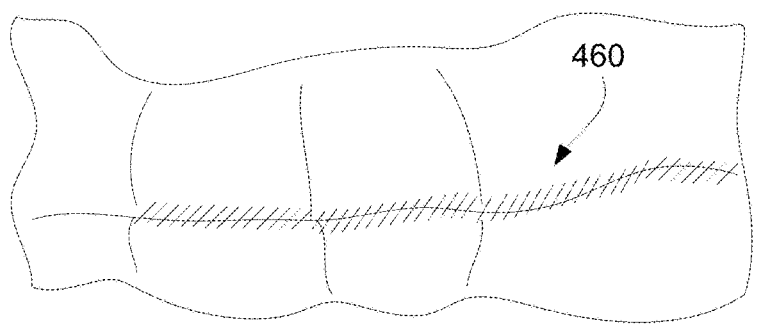
FIG. 14E shows a perspective view of a portion of the aligner having different portions fabricated to have different areas of varying friction.

Additionally, different portions of the aligners may be fabricated to have different areas 460 of varying friction, as shown in the perspective view of FIG. 14E. Such varying areas may be formed, e.g., along the edges to prevent tearing of the aligner material.

Figure 14F:
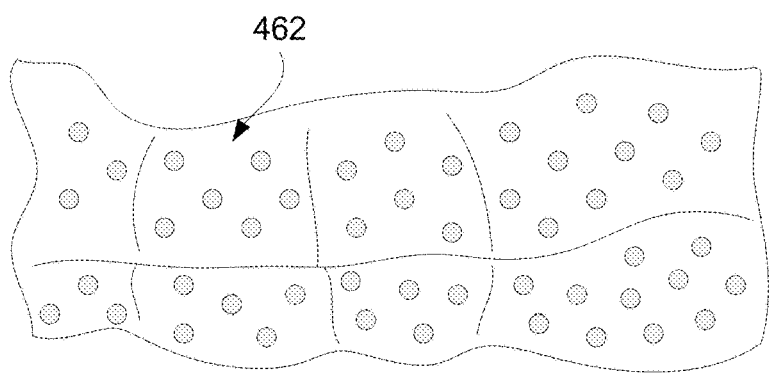
FIG. 14F shows a perspective view of a portion of the aligner having a particulate coating.

Additional attachments can be formed on the 3D printed dental appliances such as particulate coatings. The particulate coating 462 may be formed on the tooth engaging surface of the lattice 3D printed appliance in any convenient manner, e.g., fusion, sintering, etc., as shown in the perspective view of FIG. 14F. The particles making up the coating may be any convenient shape, including a spherical shape or an irregular shape, and may be constructed of metal (including alloys), ceramic, polymer, or a mixture of materials. The particulate coating adhered to the tooth engaging surface may take the form of discrete particles which are spaced apart from each other on the surface, or the form of a layer or multiple layers of particles bonded together to produce a network of interconnected pores. The particulate coating provides a porous interface into which a fluid bonding resin may readily flow and penetrate. Upon curing of the resin to solid form, mechanical interlock is achieved between the cured resin and the particulate coating. Under some circumstances chemical bonding in addition to this mechanical bonding may be achieved, e.g., by the use of polycarboxylate or glass ionomer cements with stainless steel and other metallic substrates and with ceramic substrates.

For a coating of integrally-joined particles which make up a porous structure having a plurality of interconnected pores extending therethrough, the particles are usually about −100 mesh and preferably a mixture of particles of varying particle sizes restricted to one of three size ranges, e.g., −100+325 mesh (about 50 to about 200 microns), −325+500 mesh (about 20 to about 50 microns), and −500 mesh (less than about 20 microns). The size of the particles in the porous structure determines the pore size of the pores between the particles. Smaller-sized pores are preferred for fluid resin bonding agents whereas larger-sized pores are preferred for more viscous cementitious bonding materials. The selection of particle size is also used to control the porosity of the coating to within the range of about 10 to about 50% by volume.

An adequate structural strength is required for the composite of substrate and coating, so that any fracture of the joint of the bracket to the tooth occurs in the resin and not in the coating. To achieve this condition, the structural strength of the coating, the interface between the coating and the substrate and the substrate itself is at least 8 MPa.

FIGS. 15A to 15D show exploded views of alternative lattice structures which may be utilized in any of the embodiments described herein. The lattice structures have open faces and are layered and can also be regarded as two or more interconnected reticulated layers or as structures comprising only one layer or more than two layers.

Figure 15A:
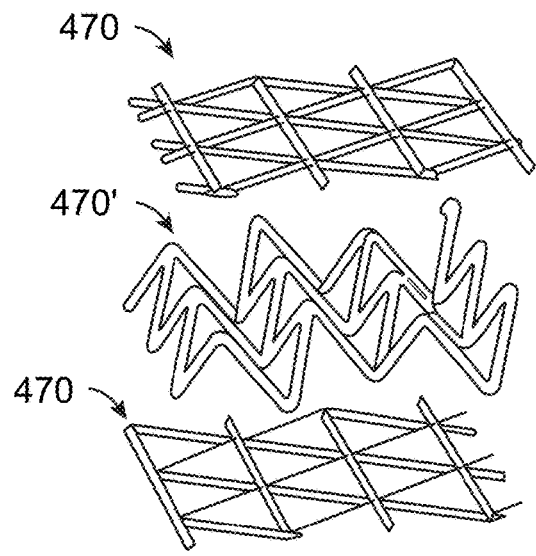
FIGS. 15A to 15D show various views of examples of lattice structures suitable for forming dental appliances.
Figure 15B:
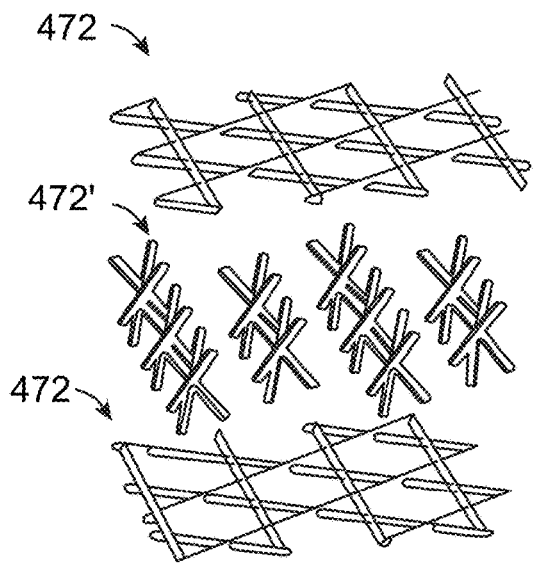
Figure 15C:
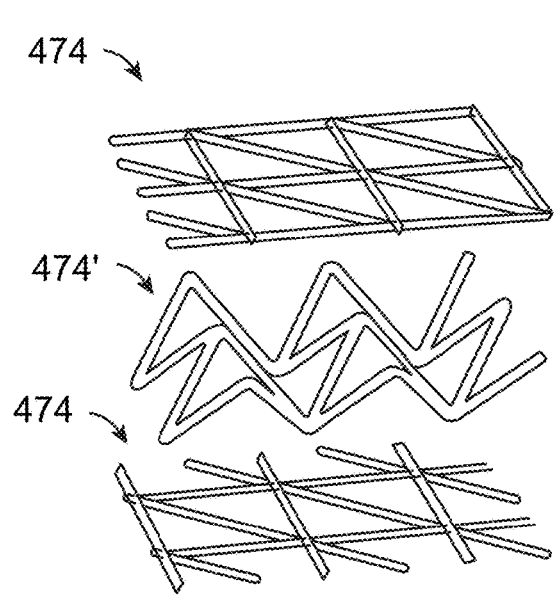
Figure 15D:
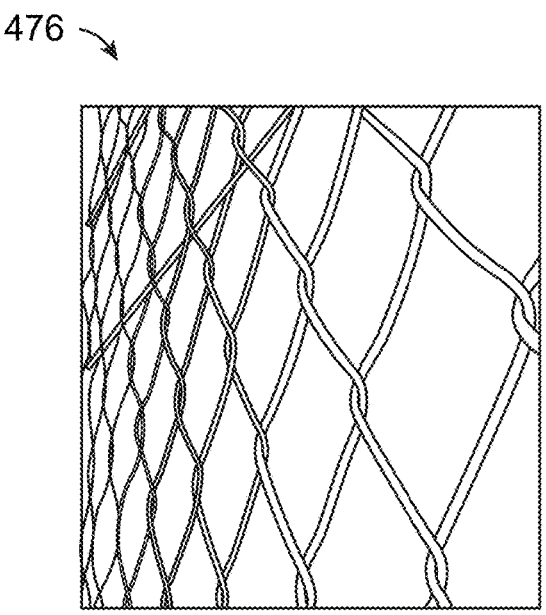

FIG. 15A shows a first and second perspective view of the lattice structure 470 having a triangular cell pattern and an example of the structure 470 reconfigured into an alternative or compressed configuration 470'. FIG. 15B shows a first and second perspective view of the lattice structure 472 having a polygonal cell pattern and an example of the structure 472 reconfigured into an alternative or compressed configuration 472'. FIG. 15C shows a first and second perspective view of the lattice structure 474 having a diamond cell pattern and an example of the structure 474 reconfigured into an alternative or compressed configuration 474'. FIG. 15D shows a perspective view of the lattice structure 476 having a linked diamond cell pattern.

During the 3D printing process, the formed oral appliance may need to be supported by an intermediate structure given the complex shapes being constructed. Such intermediate structures may be used temporarily and then removed, separated, or otherwise disengaged from the oral appliance being formed.

Figure 16:
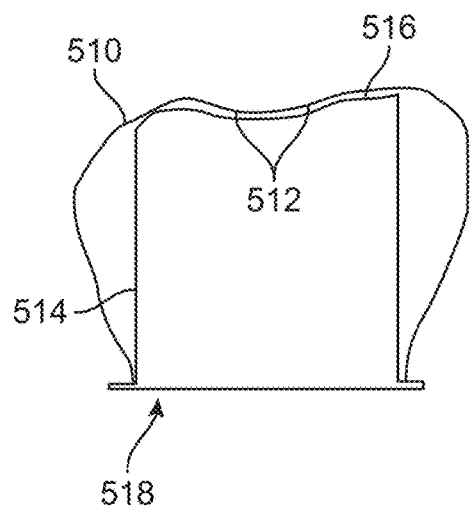
FIG. 16 shows an exemplary 3D printed dental structure with a support positioned within the structure.

FIG. 16 shows a cross-sectional side view of an exemplary 3D printed dental appliance 510 with a temporary support structure 514 positioned within the appliance 510. Typically, the dental appliance 510 is designed to stay in a patient's mouth more than 518 hours a day for about one month. Aside from durability, the shell of the dental appliance 510 is desirably thin typically having a thickness of about 0.5 mm. To be able to 3D print such a shell or dental portion for covering the teeth or tooth, the structure of FIG. 16 may utilize the inner support structure 514 to structurally support or buttress the appliance 510 formed upon the support structure 514. Because the occlusal surface 512 of the oral appliance 510 may have a complex anatomy (or terrain), the interfacing surface 516 of the support structure 514 may be formed to mirror the occlusal surface 512 so that the occlusal surface 512 formed upon the interfacing surface 516 during the manufacturing process sufficiently supports the oral appliance 510.

Once formation of the appliance 510 has been completed, the support structure 514 may be readily removed from the opening 518 defined by the appliance 510. Hence, in one embodiment, the width of the support structure 514 may be similar to the opening 518 of the appliance 510 to allow for removal of the support 514 from the appliance 510. The appliance 510 may be fabricated from a number of different types of polymers, e.g., silicone, polyurethane, polyepoxide, polyamides, or blends thereof, etc., and the support structure 514 may be fabricated from the same, similar, or different material than the appliance 510. Fabricating the support structure 514 from a material different than the material of the appliance 510 may facilitate the separation and removal of the support structure 514 from the appliance 510 when finished.

Figure 17A:
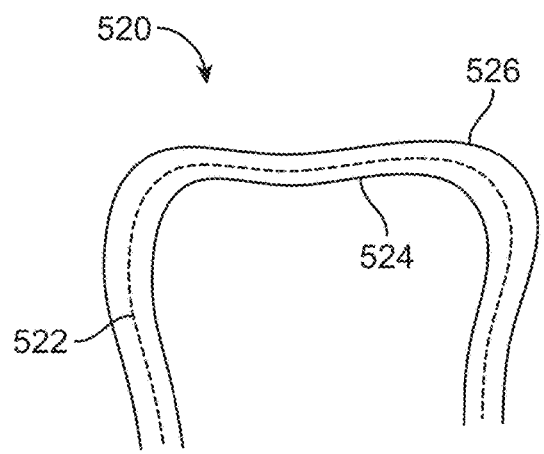
FIGS. 17A and 17B show cross-sectional side views of various embodiments of a 3D printed dental structure having an inner and outer layer.

Aside from having the support structure 514 positioned directly below the appliance 510 during fabrication, other embodiments may include a support structure formed as one or more layers, as shown in the partial cross-sectional side views of FIGS. 17A and 17B. FIG. 17A shows one embodiment of an oral appliance 520 during fabrication where an inner core layer 522 may be formed (e.g., via 3D printing) of a first material configured and shaped to follow the contours of the dentition. With the inner core layer 522 fabricated, an inner appliance layer 524 may be printed upon an interior surface of the inner core layer 522 and an outer appliance layer 526 may be printed upon an exterior surface of the inner core layer 522. The inner core layer 522 may thus be formed to be slightly oversized relative to the dentition to allow for the fabrication of the inner appliance layer 524 to size. The inner appliance layer 524 and outer appliance layer 526 may be printed upon the inner core layer 522 either sequentially or simultaneously to form the desired oral appliance 520. Subsequently, the inner core layer 522 may be melted, washed, or otherwise dissolved, e.g., via chemicals, leaving the completed oral appliance 520 with inner appliance layer 524 and outer appliance layer 526 intact.

Figure 17B:
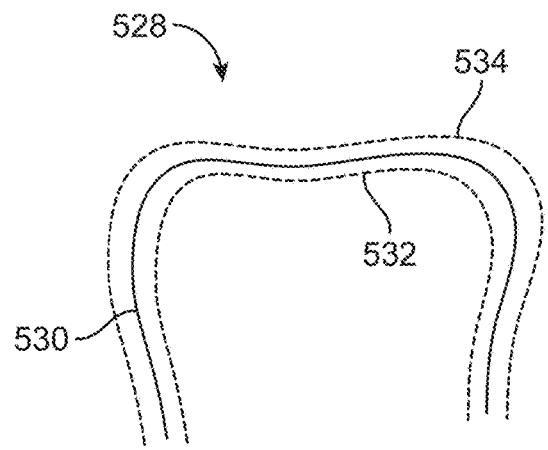

In another embodiment, FIG. 17B shows a cross-sectional side view of an arrangement where the oral appliance 528 may be fabricated by an appliance layer 530 formed between an inner core layer 532 and outer core layer 534. The inner core layer 532 may be formed to be slightly undersized relative to the dentition to allow for the fabrication of the appliance layer 530 to size. Once the appliance layer 530 has been fabricated while supported by the inner core layer 532 and outer core layer 534, both the inner core layer 532 and outer core layer 534 may be removed or otherwise dissolved leaving the appliance layer 530.

Figure 18:
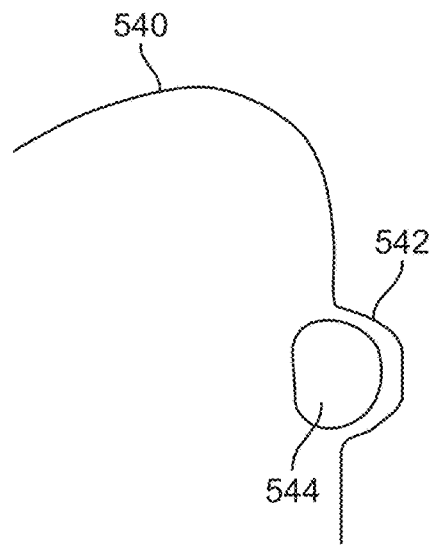
FIG. 18 shows another embodiment of a 3D printed dental structure with a pocket defined within.

In yet another embodiment, the oral appliance may be fabricated with various features such as projections, protrusions, or other shapes for providing additional flexibility in treating the patient. FIG. 18 shows a cross-sectional side view of one example of a printed oral appliance 540 having a pocket or cavity 542 formed along a side portion of the device, e.g., for receiving an attachment such as an elastic that can be placed upon the pocket or cavity 542. In this example, the support structure can include a feature or projection 544 which causes the corresponding pocket or cavity 542 to protrude from the oral appliance 540, as shown. Certain features can be 3D printed for future assembly to provide additional treatment options and improve the effectiveness of the oral appliance. In other embodiments, the support structure may be formed without any additional features but the feature or projection 544 may be adhered or otherwise secured to selected regions of the support structure for selectively forming the corresponding pocket or cavity 542 upon the oral appliance 540. The feature or projection may be optionally designed, e.g., to enable non-isotropic friction in one direction which helps device to grab teeth better and move to its designed position.

Figure 19:
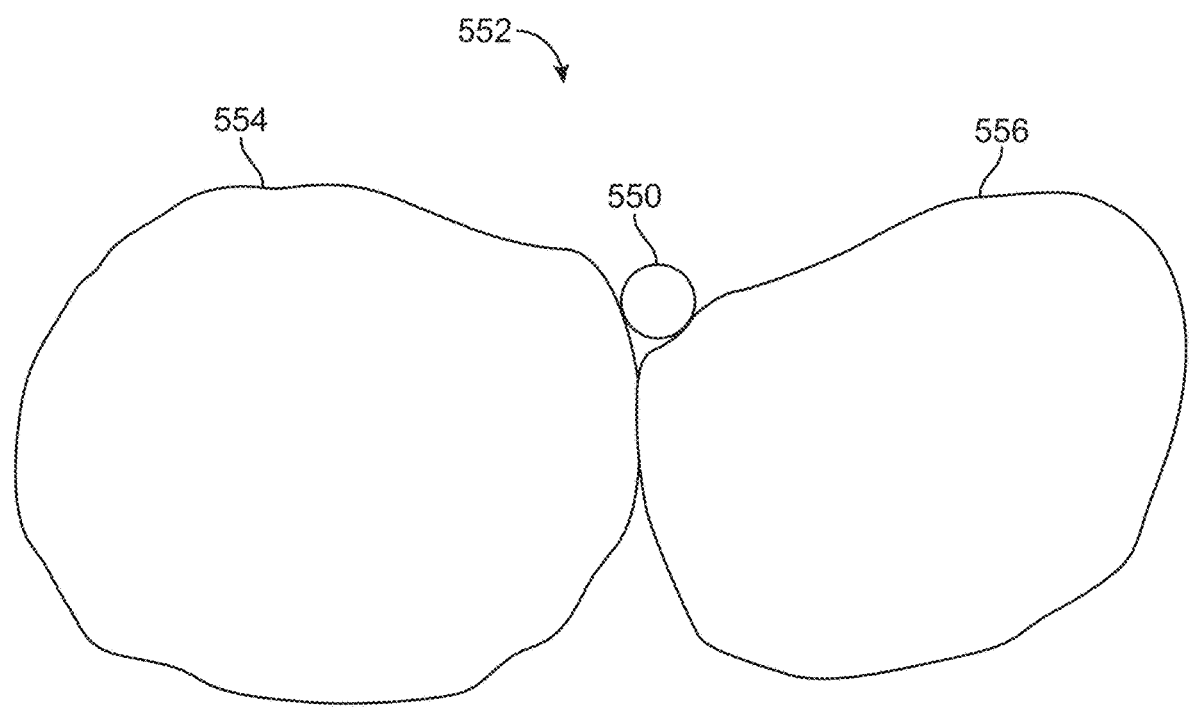
FIG. 19 shows yet another embodiment with a ball like material positioned between two tooth portions.

In yet another embodiment, features or projections may instead be incorporated into the oral appliance to impart additional forces or to facilitate tooth movements. One example is shown in the top view of FIG. 19 which illustrates a projection 550 (e.g., a polymeric or metallic ball) positioned by an oral appliance (not shown for clarity purposes) between two adjacent teeth 554, 556. The projection 550 may be fabricated as part of the oral appliance which extends from the appliance and into contact against specified regions of a tooth or teeth, e.g., to facilitate a separation movement between the adjacent teeth 554, 556. While a single projection 550 is shown, such a projection or multiple projections may be used within the oral appliance.

Figure 20:
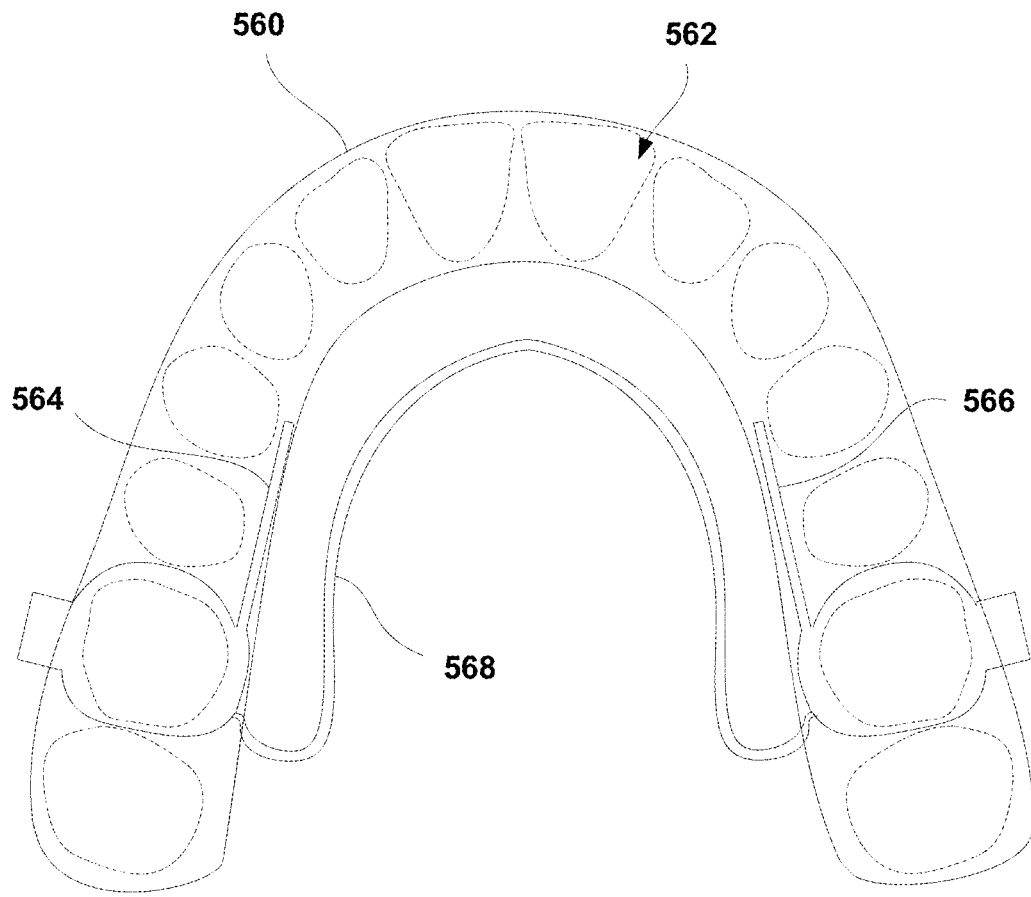
FIG. 20 shows an exemplary model having a slot for supporting metal wires therein.

Aside from projections, the oral appliance 560 may also define a number of channels, grooves, or features which support the use of additional devices. An exemplary oral appliance 560 is shown in the top view of FIG. 20 positioned upon the teeth 562 of a subject and further having slots 564, 566 defined within the oral appliance 560 for supporting wires 568 within. The oral appliance 560 may be configured and printed with the slots 564, 566 to receive, e.g., wires, hooks, rubber bands, etc., for supplementing the corrective forces imparted by the oral appliance 560 for correcting malocclusions as well as to enhance the material strength and prevent material relaxation, e.g., in cases of arch expansion. The wire 568 is show anchored within the slots 564, 566 of oral appliance 560 for illustrative purposes but alternative variations for slot positioning or incorporating other features or elements may also be used.

In another embodiment, due to accurate gingival modeling, the shell of the oral appliance can be extended or thickened to cover the gum areas without hurting patients. Such extended areas can strengthen the shell, e.g., plastic, especially at times when a shortened plastic shell may not be able to provide the strength needed.

Figure 21:
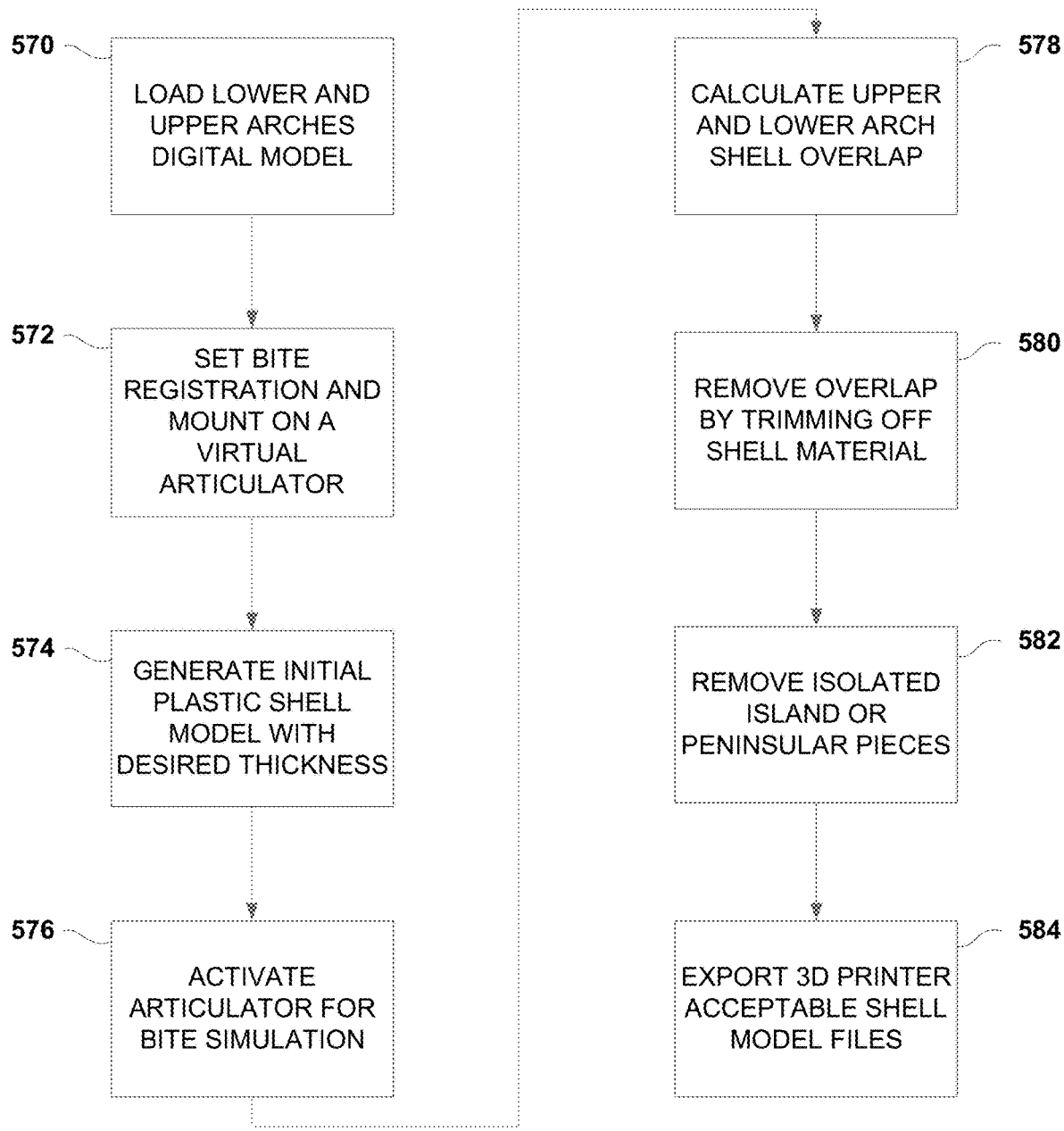
FIG. 21 shows an exemplary process for adjusting the thickness of the 3D printed oral appliance.

FIG. 21 shows an exemplary process for adjusting the thickness of the 3D printed oral appliance. With the subject's dentition scanned and electronically converted, the upper and lower arch models 570 may be loaded into the memory of a computer system having a programmable processor. The bite registration may be set and the resulting digital model may be mounted on a virtual articulator 572. The system may be programmed to generate an initial shell model having a predetermined thickness 574 where the thicker the portions of the oral appliance provides a relatively stronger region. The practitioner can incorporate features such as the projections 550 shown above in FIG. 19 and/or further incorporate additional features such as slots 564, 566 or any other features into the model of the oral appliance. The system may be programmed to then activate an articulator to perform a simulated bite 576 between the upper and lower arch models to calculate any overlap between the upper and lower arch shell 578. Any resulting stresses on the shell model of the oral appliance may also be determined.

The system may then remove any overlap by trimming off the shell material 580 in the model and any isolated islands or peninsular pieces may then be removed as well 582. The resulting 3D model may then be exported to a 3D printer 584 for fabricating the dental appliance or shell.

Figure 22:
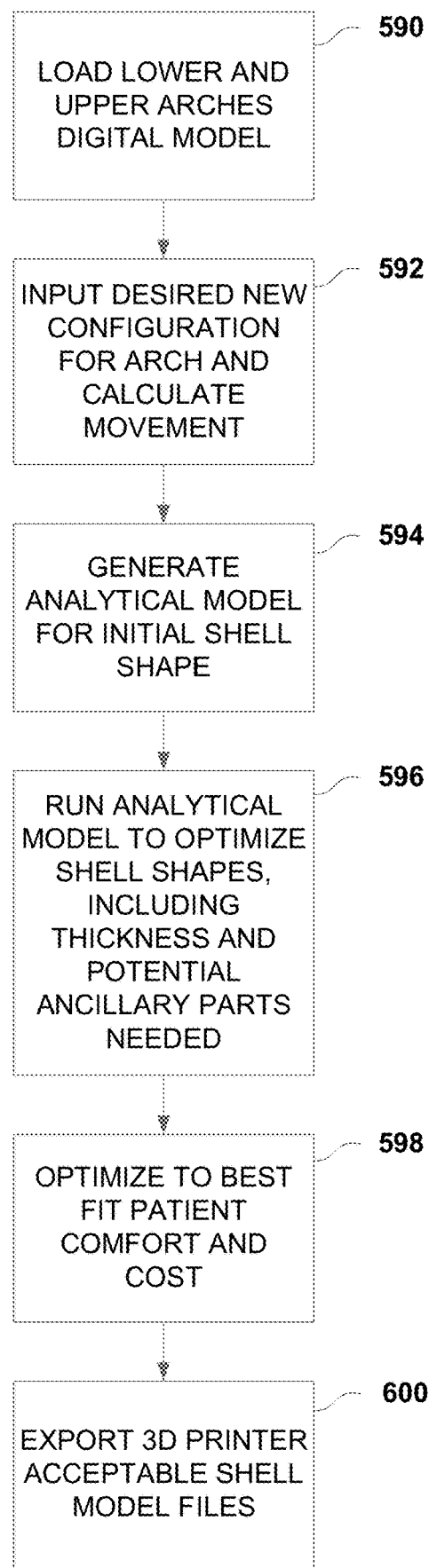
FIG. 22 shows an exemplary process for determining the thickness of an oral appliance based on physical simulation.

FIG. 22 shows another exemplary process for determining the thickness of an oral appliance based on physical simulations. In this process, the digital model of the lower arch and upper arch may be loaded 590 into the memory of a computer system, as above. The new desired configuration for the arch and/or dentition may be input into the system which may calculate the necessary movements to occur for the tooth or teeth 592. The system may then generate an analytical model for an initial shell shape 594. The system may further run an analytical model to optimize shell shapes, including thicknesses and potential ancillary components or parts which may be needed or desired 596. The analytical 3D model may be further optimized for best patient comfort and resin cost minimization 598 and the result may then be provided to a 3D printer 600 for fabricating the oral appliance or shell.

Generally, the pressure formed plastic shell forming conventional oral appliances have intrinsic short-comings. Ideally the plastic shell has a relatively thinner layer (e.g., thinner than other regions of the appliance) on regions of the appliance which contact the occlusal areas of the patient's dentition so the patient's bite is unaffected when in use during treatment. On the other hand, the embrasure or side surface areas are ideally relatively thicker to provide enough force to push the tooth or teeth to its designated location for correcting malocclusions. Oftentimes, these embrasure regions are stretched thinner during the forming process for the oral appliance. In forming the oral appliance, the system described herein may determine the areas of the oral appliance which affects the patient's bite and may configure the appliance to be thinner in particular areas or may even remove some material from the appliance entirely to form a hole.

Free-form lattice structures which fit at least part of the surface, e.g. external contour, of a body part may be used to form the oral appliance. Specifically, the embodiments described may utilize free-form lattice structures for forming or fabricating appliances which are designed for placement or positioning upon the external surfaces of a patient's dentition for correcting one or more malocclusions. The free-form structure is at least partially fabricated by additive manufacturing techniques and utilizes a basic structure comprised of a lattice structure. The lattice structure may ensure and/or contribute to a free-form structure having a defined rigidity and the lattice structure may also ensure optimal coverage on the dentition by a coating material which may be provided on the lattice structure. The lattice structure is at least partly covered by, impregnated in, and/or enclosed by the coating material. Furthermore, embodiments of the lattice structure can contribute to the transparency of the structure.

The term "free-form lattice structure", as used herein, refers to a structure having an irregular and/or asymmetrical flowing shape or contour, more particularly fitting at least part of the contour of one or more body parts. Thus, in particular embodiments, the free-form structure may be a free-form surface. A free-form surface refers to an (essentially) two-dimensional shape contained in a three-dimensional geometric space. Indeed, as detailed herein, such a surface can be considered as essentially two-dimensional in that it has limited thickness, but may nevertheless to some degree have a varying thickness. As it comprises a lattice structure rigidly set to mimic a certain shape it forms a three-dimensional structure.

Typically, the free-form structure or surface is characterized by a lack of corresponding radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surfaces. Triangulated surfaces are used in Standard Triangulation Language (STL) files which are known to a person skilled in CAD design. The free-form structures fit the surface of a body part, as a result of the presence of a rigid basic structures therein, which provide the structures their free-form characteristics.

The term "rigid" when referring to the lattice structure and/or free-form structures comprising them herein refers to a structure showing a limited degree of flexibility, more particularly, the rigidity ensures that the structure forms and retains a predefined shape in a three-dimensional space prior to, during and after use and that this overall shape is mechanically and/or physically resistant to pressure applied thereto. In particular embodiments the structure is not foldable upon itself without substantially losing its mechanical integrity, either manually or mechanically. Despite the overall rigidity of the shape of the envisaged structures, the specific stiffness of the structures may be determined by the structure and/or material of the lattice structure. Indeed, it is envisaged that the lattice structures and/or free-form structures, while maintaining their overall shape in a three-dimensional space, may have some (local) flexibility for handling. As will be detailed herein, (local) variations can be ensued by the nature of the pattern of the lattice structure, the thickness of the lattice structure and the nature of the material. Moreover, where the free-form structures envisaged herein comprise separate parts (e.g. non-continuous lattice structures) which are interconnected (e.g., by hinges or by areas of coating material), the rigidity of the shape may be limited to each of the areas comprising a lattice structure.

Descriptions of dental appliance fabrication processes may be found in further detail in U.S. Prov. App. 62/238,514 filed Oct. 7, 2015, which is incorporated herein by reference in its entirety and for any purpose.

Generally, the fabrication process includes designing an appliance worn on teeth to be covered by a free-form structure, manufacturing the mold, and providing the (one or more) lattice structures therein and providing the coating material in the mold so as to form the free-form structure. The free-form structures are patient-specific, i.e. they are made to fit specifically on the anatomy or dentition of a certain patient, e.g., animal or human. In fabricating the oral appliance, the 3D representation of the surfaces, e.g. external contours, of a patient's dentition for correcting one or more malocclusions may be captured via a 3D scanner, e.g. a hand-held laser scanner, and the collected data can then be used to construct a digital, three dimensional model of the body part of the subject. Alternatively, the patient-specific images can be provided by a technician or medical practitioner by scanning the subject or part thereof. Such images can then be used as or converted into a three-dimensional representation of the subject, or part thereof. Additional steps wherein the scanned image is manipulated and for instance cleaned up may be envisaged.

In fabricating oral or dental appliances which are used to treat malocclusions in a patient's dentition, the oral appliance may be initially formed via, e.g., thermal forming or three-dimensional (3D) printing techniques. Once formed, the oral appliance may require further processing to trim excess material for ensuring a good fit on the patient. However, trimming this excess is typically a time-consuming process which requires a separate step after forming the appliance.

In one embodiment, the forming and cutting of the oral appliance may be accomplished in an automated process and with a single machine. Generally, a patient's scanned dentition may be used to create one or more molds of the dentition where each subsequent mold is configured to subsequently follow a corrective path for one or more teeth for correcting malocclusions in the dentition. Each of the one or more molds may be used as a mold for thermal forming or 3D printing a corresponding oral appliance upon the molds. The resulting oral appliances may be used in sequence to move the dentition for correcting the malocclusions.

Figure 23:
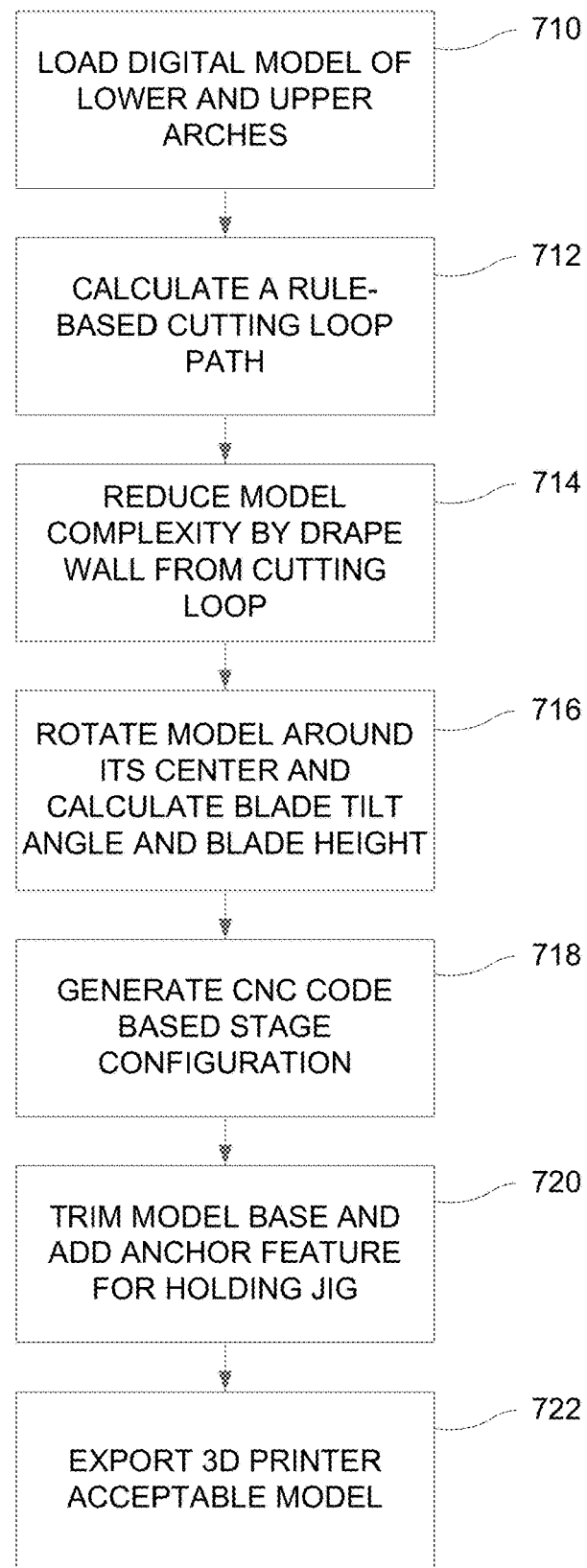
FIG. 23 shows an exemplary process for fabricating an oral appliance.

FIG. 23 shows an exemplary process for utilizing computerized or computer numerical control (CNC) for fabricating the oral appliances. Typical CNC systems and end-to-end component design is highly automated using computer-aided design (CAD) and computer-aided manufacturing (CAM) dental software. The process begins by loading digital models of the lower and upper arches 710 of the subject's dentition into a computer system having a processor. This may involve capturing the 3D representation of the surfaces, e.g. external contours, of a patient's dentition for correcting one or more malocclusions. For this purpose, the subject may be scanned using a 3D scanner, e.g. a hand-held laser scanner, and the collected data can then be used to construct a digital, three dimensional model of the body part of the subject. Alternatively, the patient-specific images can be provided by a technician or medical practitioner by scanning the subject or part thereof. Such images can then be used as or converted into a three-dimensional representation of the subject, or part thereof.

With the digital model of the subject's dentition loaded into the computer system, the process then calculates a rule-based cutting loop path 712 on the digital model for determining a path along which the CNC machine may follow for trimming the mold upon which the oral appliance is fabricated. Once the cutting loop path has been determined, the process may then reduce the model complexity by applying a drape wall 714 (as described in further detail below) which digitally extends from the cutting loop path towards a bottom of the mold model (e.g., away from the portion of the appliance which contacts the teeth and towards the portion of the appliance which extends towards the gums). The drape wall functions by defining a region of the oral appliance which can be ignored since this portion is to be removed or trimmed.

The digital model may then be rotated around its center in relation to a reference plane in order to calculate a cutting blade tilt angle and blade height 716 (relative to the reference plane) which may be applied during the actual trimming procedure. With this information, the code to be sent to the CNC machine may be generated based on the stage configuration to be utilized 718. A physical mold base to be used in the processing procedure may be trimmed and one or more anchoring features may be incorporated into the mold base for securing a holding jig which may be used to secure the oral appliance 720 to the mold base. The completed digital model may then be exported as, e.g., a 3D printer acceptable model 722, for printing the oral appliance or mold upon which an oral appliance may be formed.

Figure 24:
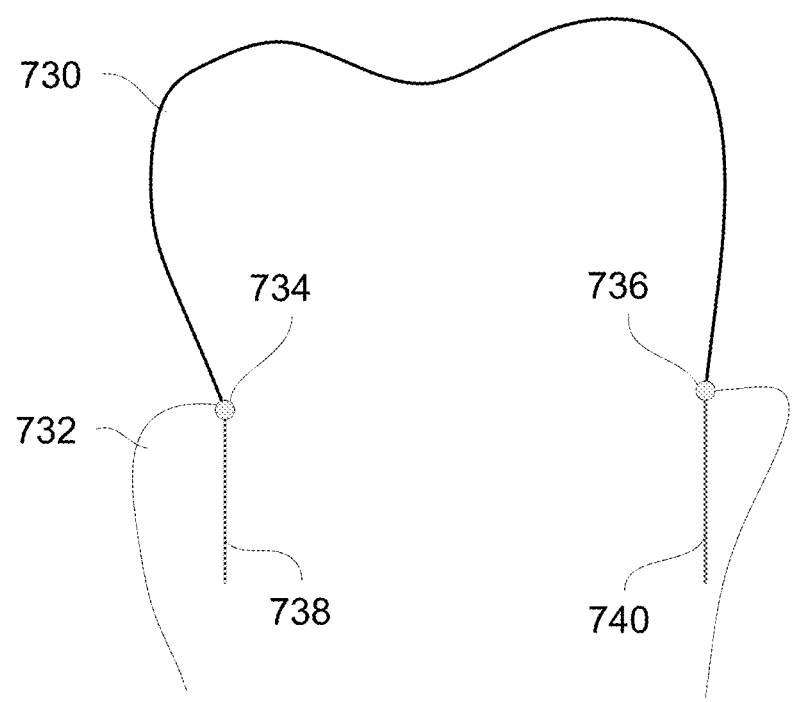
FIGS. 24 and 25 show side views of an exemplary process of defining a trim line between opposed dots on a digital model of the oral appliance.
Figure 25:
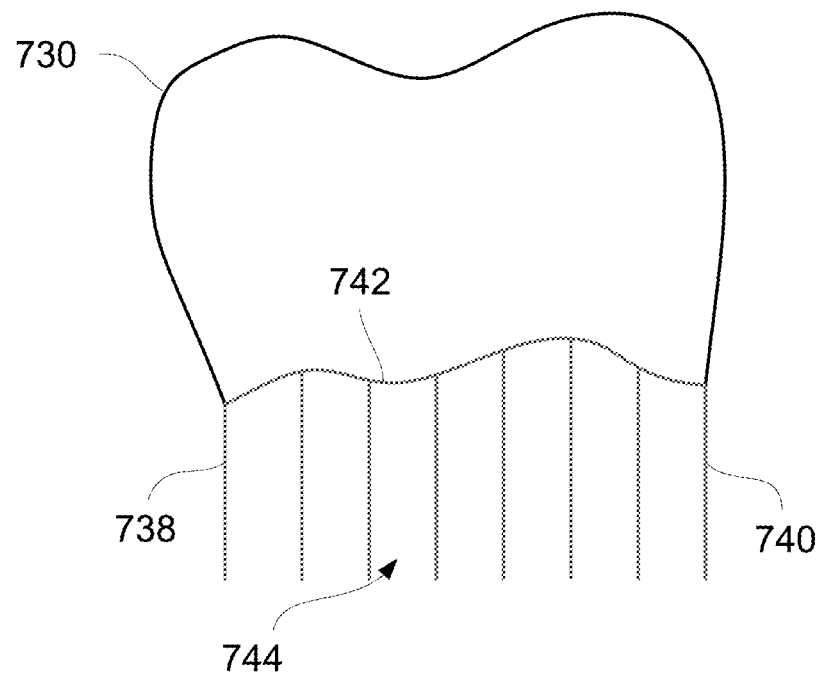

FIGS. 24 and 25 show side views of a portion of a digital model of a patient's dentition showing a tooth 730 and gums 732, as an example. In calculating a rule-based cutting loop path 712, as shown in FIG. 23 above, the scanned image of the patient's dentition may be processed to identify the interface areas between the teeth and gums 732. One or more markers 734, 736 may be digitally placed on the model at these interface regions such that the markers 734, 736 are opposed to one another on the model. A boundary or trim line 742 may then be defined to extend between the markers 734, 736 such that the trim line 742 follows the border between the teeth and gums. With the trim line 742 identified on the model, a series of drop lines 738, 740 which are parallel to one another and spaced apart, e.g., uniformly, relative to one another may be formed to begin from the trim line 742 and extend away from the trim line 742 and away from the dentition in a straight path. This base region 744 formed by the drop lines 738, 740 below the trim line 742, i.e., away from or opposite to the dentition, may be identified and demarcated as a region to be removed from the mold.

To ensure that the height of the mold including the base region 744 does not excessively stretch the material forming the oral appliance, the system may be used to determine the lowest point (relative to the trim line 742 and appliance 730) for trimming the entire mold just above this identified lowest point. In one embodiment, the trimming may be done with a predetermined margin, e.g., 2 mm, above the lowest identified point. The base region wall can also be tapered slightly based on the height of the base region wall so that the width of the base region 744 tapers from a larger width adjacent to the trim line 742 down to a relatively smaller width away from the trim line 742. The resulting mold formed from the dentition (or corrected dentition) is shown in the side view of FIG. 25 where the base region 744 has a minimum height of the predetermined margin, e.g., 2 mm.

Figure 26:
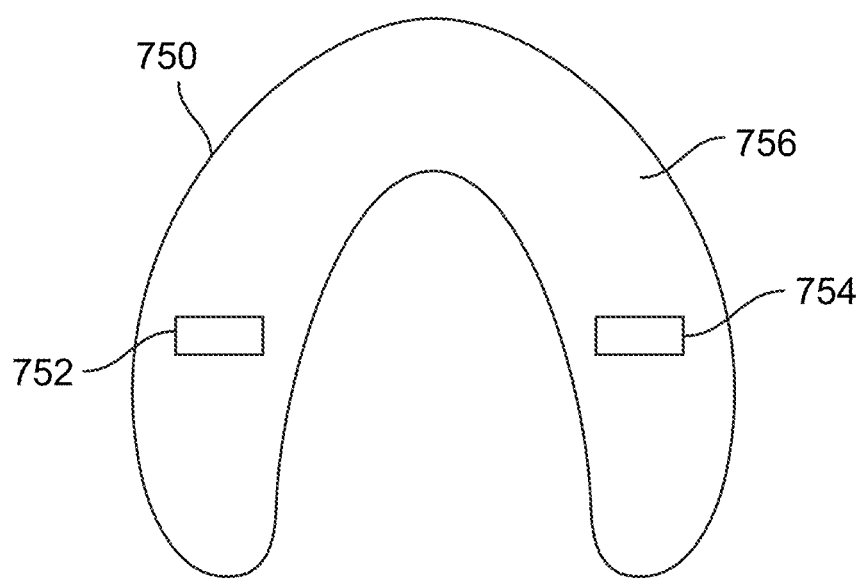
FIG. 26 shows a top view of an oral appliance formed with one or more slots to facilitate manufacturing.
Figure 27:
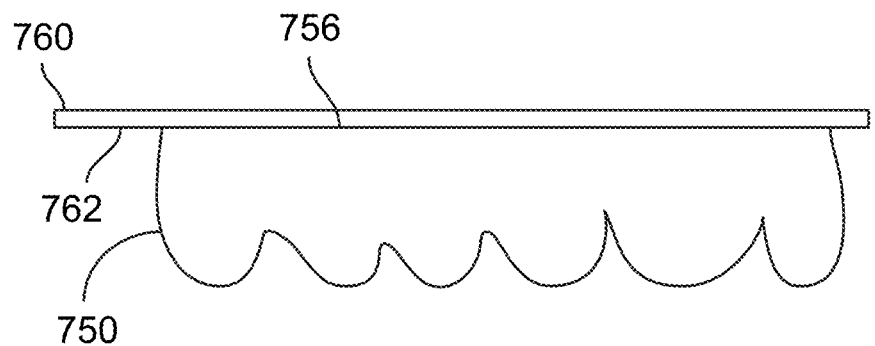
FIG. 27 shows a side view of an oral appliance mounted on a base for manufacturing.
Figure 28:
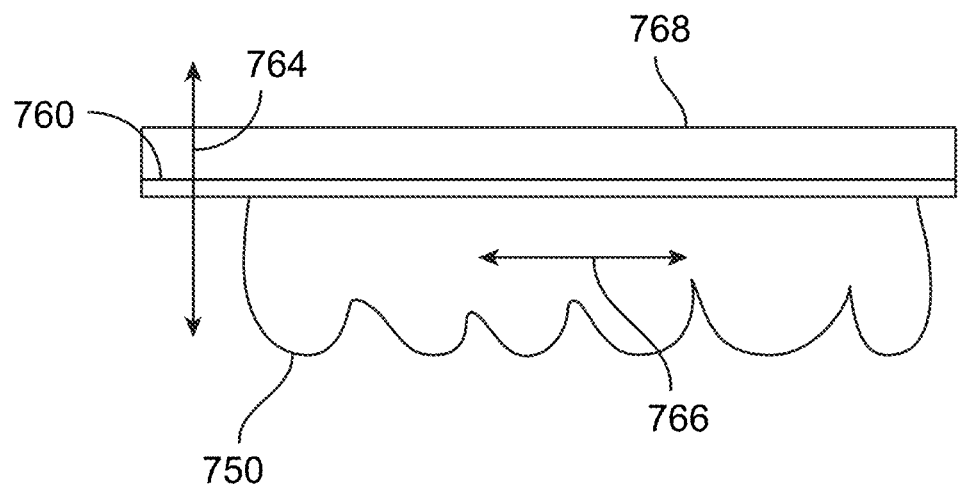
FIG. 28 shows a side view of the oral appliance and some of the directions that the appliance may be translated and/or rotated to facilitate trimming of the appliance.
Figure 29:
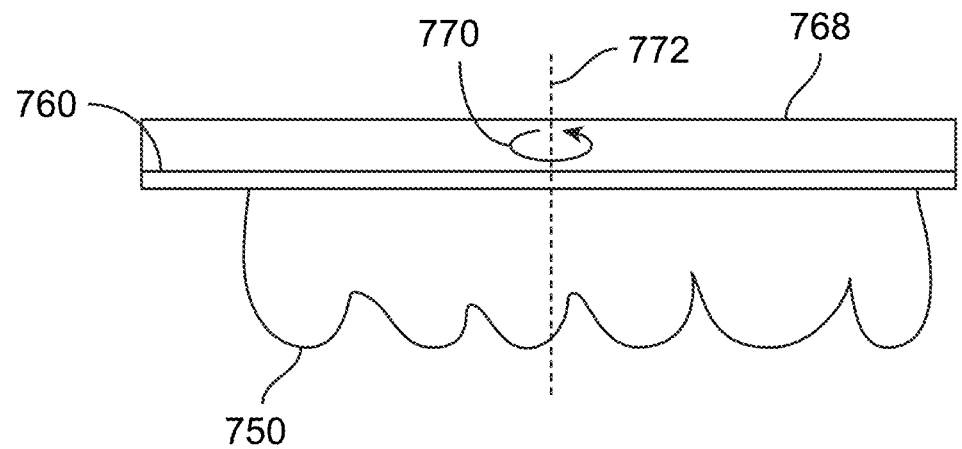
FIG. 29 shows a top view of a cutting device which may be used to trim the oral appliance and some of the directions that the cutting device may be articulated.

Once the mold has been formed with the base region 744, the mold may be further processed. A bottom view of a formed mold 750 is shown in FIG. 26 with slots 752, 754 formed into a surface 756 of the mold 750 into which tools or anchors can be inserted for securing the mold 750 in place during further processing procedures. FIG. 27, for example, shows a side view of the fabricated mold 750 secured along its interface surface 756 and anchored via slots 752, 754 to a surface 762 of a platform 760. FIG. 28 shows one configuration where the platform 760 holding the physical mold 750 for pressure-forming the oral aligner may be positioned upside down, i.e., such that the mold 750 is held in an inverted position as shown. The platform 760 may be fixed or secured upon a stage 768 which may be actuated to move the platform 760 and mold 750 in a vertical direction 764 (up/down) or linearly 766 within a plane defined by the stage 768 and platform 760, as shown in FIG. 28, to facilitate cutting or trimming processes for the mold 750. The stage 768 may also be actuated to rotate 770 the platform 760 and mold 750 within the plane defined by the stage 768 such that the stage 768 rotates about an axis which may be aligned to be collinear with a central axis 772 of the mold 750, as shown in FIG. 29.

Another configuration may position the stage 768 relative to a blade which may be translated and/or rotated relative to mold 750 and stage 768. The system may calculate each motion stage parameters and while the mold 750 is moved rotationally, the blade may be used to cut or trim the mold 750, as needed. This may involve rotating the model 750 around its center and calculating the blade tilt angle and blade height 716, as described above.

Yet another configuration may involve moving the stage 768 and mold 750 relative to a stationary blade such that the mold 750 is rotated, tilted, and/or translated by the stage 768 while the position of the blade remains unchanged. The system then adjusts different tools to trim the mold 750 at the pre-designated cutting path. In this or any other variation, the blade can include a mechanical blade or a laser cutting tool and software may be used to calculate the laser focus to easier move the source back and force or attenuate its power to focus and cut the mold 750 at designated locations.

Figure 30:
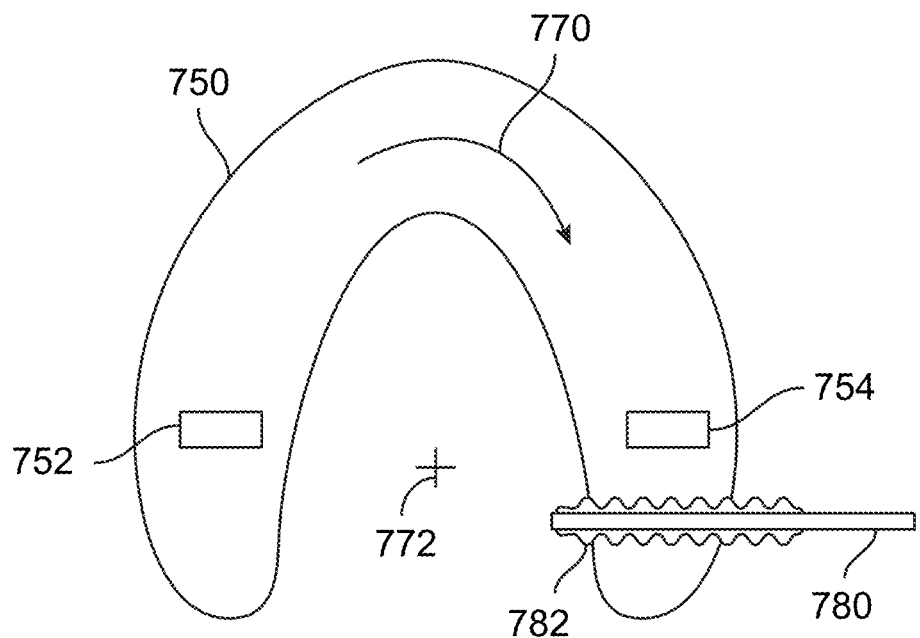
FIG. 30 shows a top view of an oral appliance and a cutting device for manufacturing.

In one implementation for processing the mold, FIG. 30 shows a top view of a mold 750 positioned upon a stage and rotated relative to a stationary cutting blade 780. The mold 750 may be secured to the underlying platform and stage and rotated within the plane of the platform in the direction 770 about its central axis 772 which may be coincident with the axis of rotation defined by the stage. The cutting blade 780 having a cutting edge 782 may be positioned relative to the mold at the predetermined height and angle relative to the mold 750, as described herein, to trim the mold 750 as it rotates.

In this variation, instead of generating a complex 3D cutting curve, the system simply uses a 2D flat curve by optionally setting a water mark cutting plane. The advantage is that no numerical controller is needed to cut the molds. Instead, the mold 750 can be simply placed by hand and rotated (e.g., manually or automatically), as shown, to push it through or past the cutting blade 780. The action may be similar to cutting a wood board with a circular motion rather than a straight or linear motion.

Another advantage of this configuration is the ability to utilize a separate fixture which can be used to sandwich the material forming the oral appliance after placement upon the mold, e.g., when thermal forming the oral appliance. The material from which the oral appliance is thermal formed, if used for fabrication, may be secured directly removing the need for yet another fixture on the mold itself. One implementation uses a two-dimensional (2D) laser cutting tool that can be used to cut along a flat curve formed by a horizontal silhouette line generated by a projection to the base surface.

Figure 31:
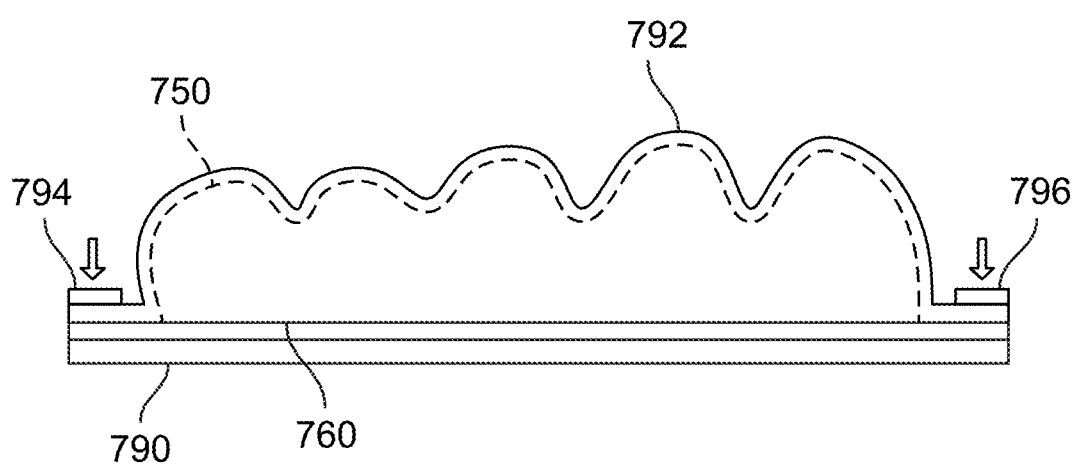
FIG. 31 shows a side view of an oral appliance secured to a base for processing.

FIG. 31 shows a side view of one embodiment where the mold 750 is positioned above a platform 760 with the plastic shell mold 792 after thermal forming upon the mold 750. The entire assembly of the mold 750, platform 760, and shell mold 792 rests on a flat bottom fixture base 790 having a clamping fixture with one or more clamping plates 794, 796 on either side to secure the mold 750 and shell mold 792. The fixture assembly may be used to secure the shell mold 792 for further processing such as trimming. Once the processing has been completed, the clamping plates 794, 796 may be released and the shell mold 792 and/or mold 750 may be removed from the fixture base 790.

Figure 32:
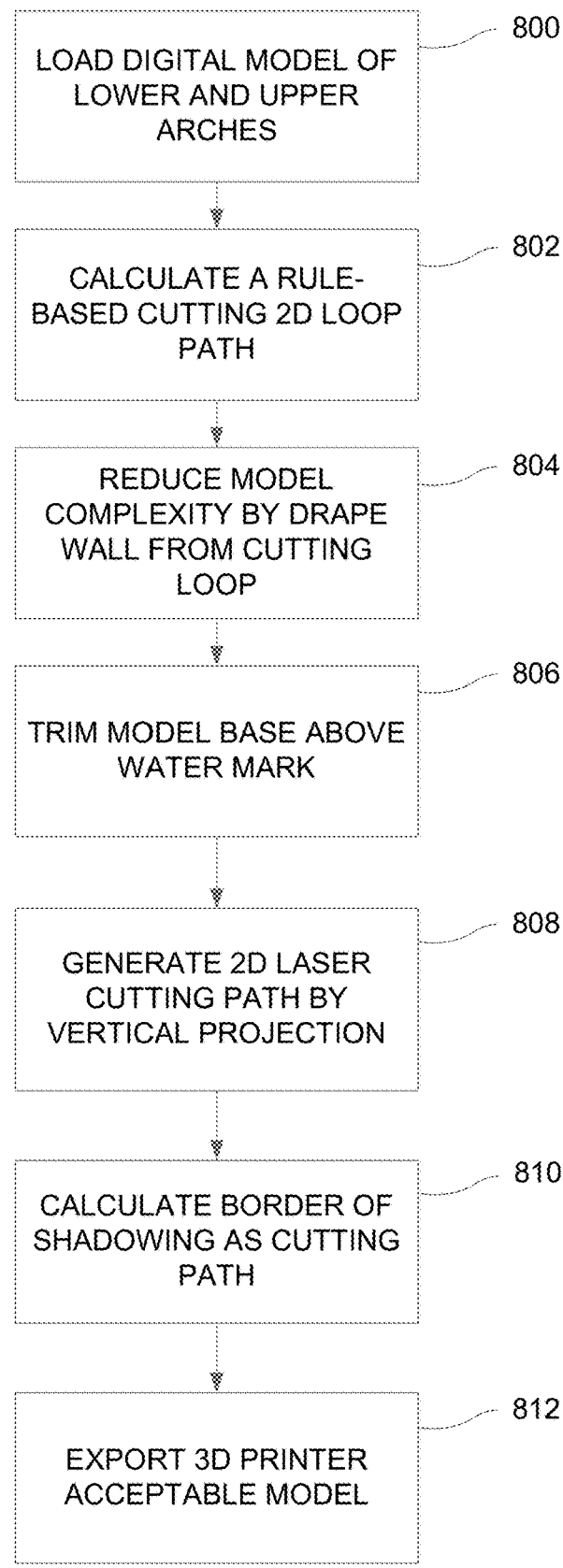
FIG. 32 shows an exemplary process for laser cutting a physical mold for the oral appliance.

In the event that the physical mold is processed by laser cutting, the steps shown in the flow diagram of FIG. 32 may be implemented in another embodiment. Initially, a digital model of the lower and upper arches may be loaded in the system 800, as described previously. The system may then calculate a rule based cutting loop path for the 2D cutting system 802, as discussed above. Model complexity may be reduced by applying the drape wall from the cutting loop 804, as also discussed above. The process trims the mold base above a water mark 806 which may be imprinted upon the mold to demarcate a boundary. For laser cutters, the system may generate a 2D laser cutting path using vertical projects 808 and determine the border of the shadow as the cutting path 810. The system may then export the 3D printer model 812 for fabrication. The process may be repeated for each subsequent mold used for fabricating one or more of the corresponding oral appliances.

Figure 33:
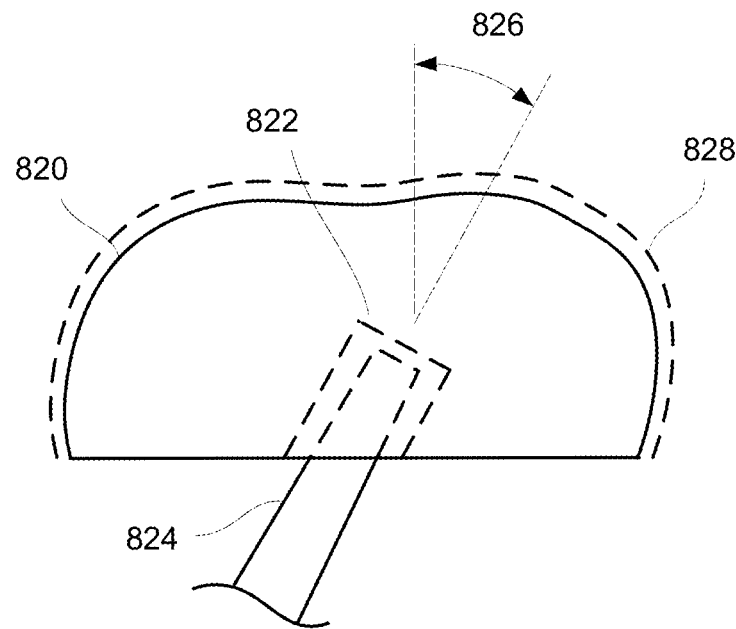
FIG. 33 shows a side view of an oral appliance formed with a tooling cavity to facilitate articulation of the oral appliance.

Regardless of how the mold is trimmed or how the oral appliance is processed upon the mold, the separation and release of the shell (aligner or oral appliance) from the mold can be generally difficult due to the lack of any features for grabbing the mold. To address this, one or more holes or cavities 822 may be drilled or otherwise defined at various locations within the mold 820 and optionally at an angle 826 relative to a normal direction of the mold, as shown in the end view of FIG. 33. The angling of the hole or cavity 822 enables the insertion of a tool 824 which may be positioned within to provide a counterforce for releasing and removing an oral appliance 828 formed upon the mold 820.

Figure 34:
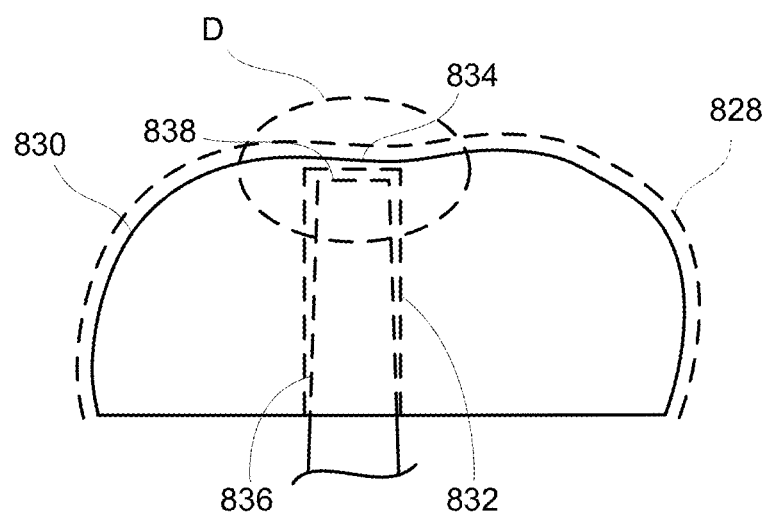
FIG. 34 shows a side view of another oral appliance having a region formed to facilitate removal of the appliance via a stream of air or gas.

Another embodiment shown in the end view of FIG. 34 which illustrates an end view of a mold 830 formed to have a hole or cavity 832 which extends through the bottom of the mold 830 and into proximity of the top of the mold, i.e., where the model of the patient's dentition is located. A thin layer 834 of the mold may extend over the hole 832 to provide a surface upon which the oral appliance 828 may be fabricated, as described herein. However, once fabrication of the oral appliance 828 has been completed and trimmed suitably, the tip 838 of a tool 836 appropriately sized may be inserted into the opening 832 and pushed through the thin layer 834 of the mold 830 and into contact against an inner surface of the oral appliance such that the oral appliance 828 may be urged to release from the mold 830. Alternatively, the tool 836 may comprise an air blower so that the tip 838 may be positioned within the opening 832 into proximity of the layer 834, as shown by the detail view D, where a jet of air introduced through tip 838 may be break through the layer 834 and urge the oral appliance 828 to release from the mold 830.

To ensure that the mold 830 retains its strength during fabrication of the mold, oral appliance, or release of the oral appliance from the mold, the mold 830 may be optionally fabricated to include a honeycomb, mesh, or other porous feature underlying the surface of the mold 830. With the added structural strength provided by a honeycomb or mesh, the layer 834 may be broken or punctured and still allow of the passage of the air but the mold 830 may have the structural resilience to withstand the pressures generated by the shell formation upon the mold 830 surface.

Figure 35:
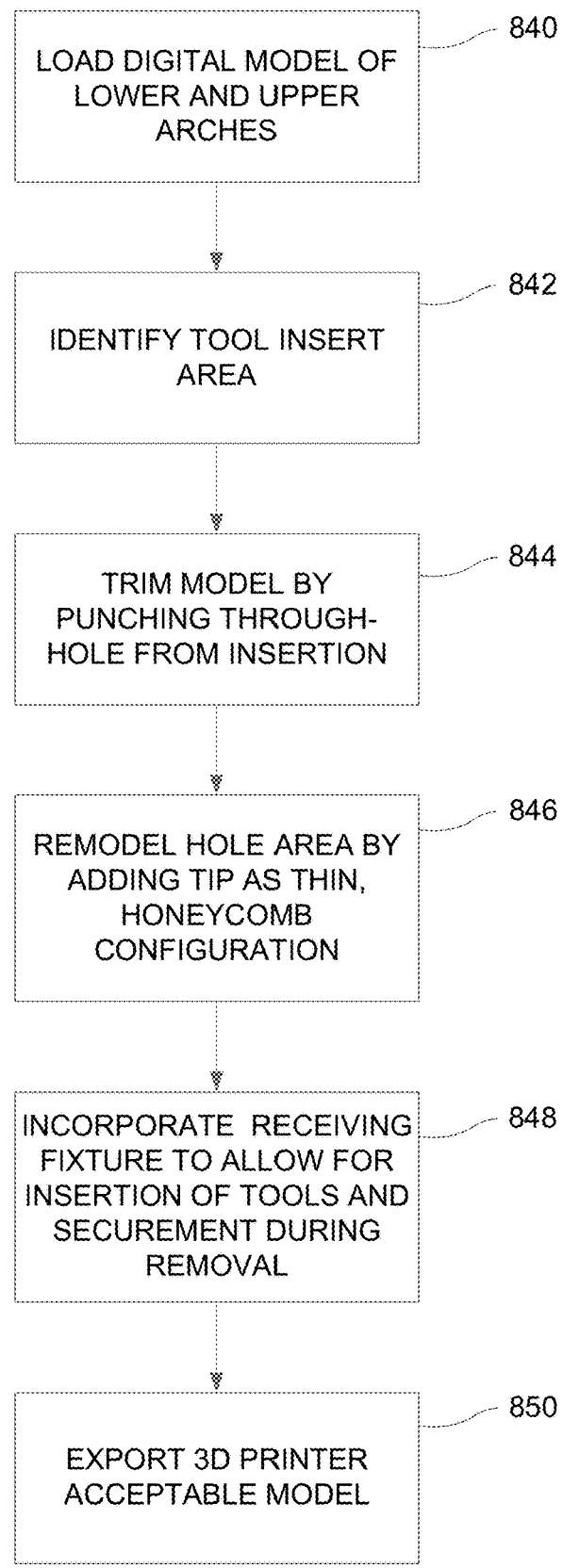
FIG. 35 shows an exemplary process for facilitating removal of the oral appliance.

FIG. 35 illustrates a flow diagram for removing the oral appliance fabricated upon a mold, as described above. As previously described, the digital model of the lower and upper arches may be loaded into the computer system 840. The system may then identify an appropriate area along the model for tool insertion 842. Such an area may be located away from the dentition model and so as not to interfere with the fabrication of the oral appliance upon the mold. The system may trim the model by defining a through-hole from insertion 844 and to strengthen the through-hole, the system may then remodel the hole area by forming the region of the hole adjacent to where the dentition is modeled as a mesh or honeycomb configuration 846 to provide strength to the model when fabricated but which still allows for air to pass through the openings defined by the mesh or honeycomb. The model may incorporate a receiving fixture to allow for the insertion of tools and/or allows for the securement of the mold during removal of the oral appliance from the mold 848. Once the model has been completed, a 3D printer acceptable model may be exported 850.

Figure 36:
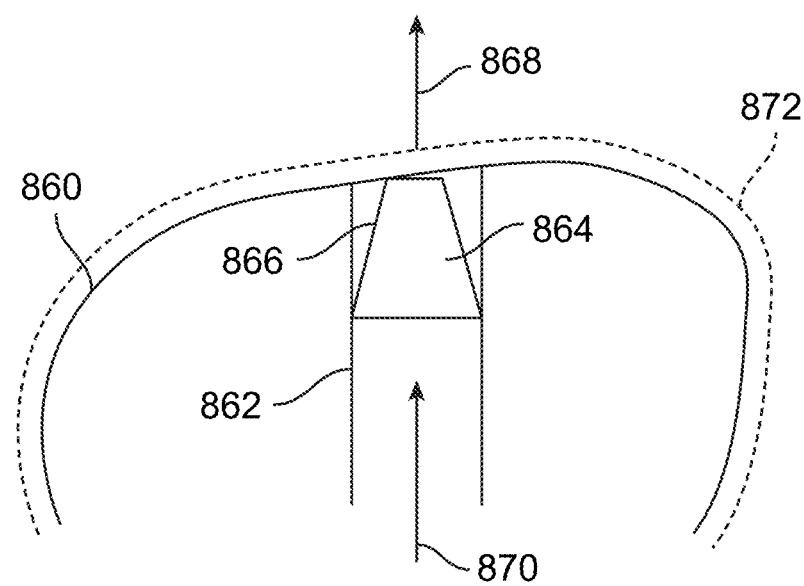
FIG. 36 shows a side view of another oral appliance having a cavity formed to facilitate its removal via a wedged removal member.

FIG. 36 shows yet another exemplary embodiment for facilitating removal of the fabricated oral appliance from the mold in the end view of mold 860. The mold 860 may be formed to define an opening or channel 862 which extends through the mold 860 from a bottom (e.g., opposite to the portion of the mold replicating the dentition) towards a top (e.g., portion of the mold replicating the dentition such as the occlusal surfaces). In this embodiment, a tapered structure 864 may be formed to be part of the oral appliance 872 which is formed upon the mold 860. The tapered structure 864 may remain attached to an internal surface of the oral appliance while being formed with a tapered surface 866 which tapers to a larger diameter structure within the opening or channel 862 away from the oral appliance 872.

The tapered structure 864, once formed, may present a cork-like structure which helps to secure the oral appliance upon the mold 860 during fabrication and processing. Once the oral appliance 872 is completed and ready for release and removal from the mold 860, a tool may be inserted into the opening or channel 862, in the direction 870 as indicated, and used to gently push against the bottom surface of the tapered structure 864 to urge the release of the oral appliance 872 from the mold 860 until the tapered structure 864 is removed entirely from the opening or channel 862, in the direction 868 as indicated. Once the oral appliance 872 has been removed entirely, the tapered structure 864 may be removed from the oral appliance 872 as well.

Figure 37:
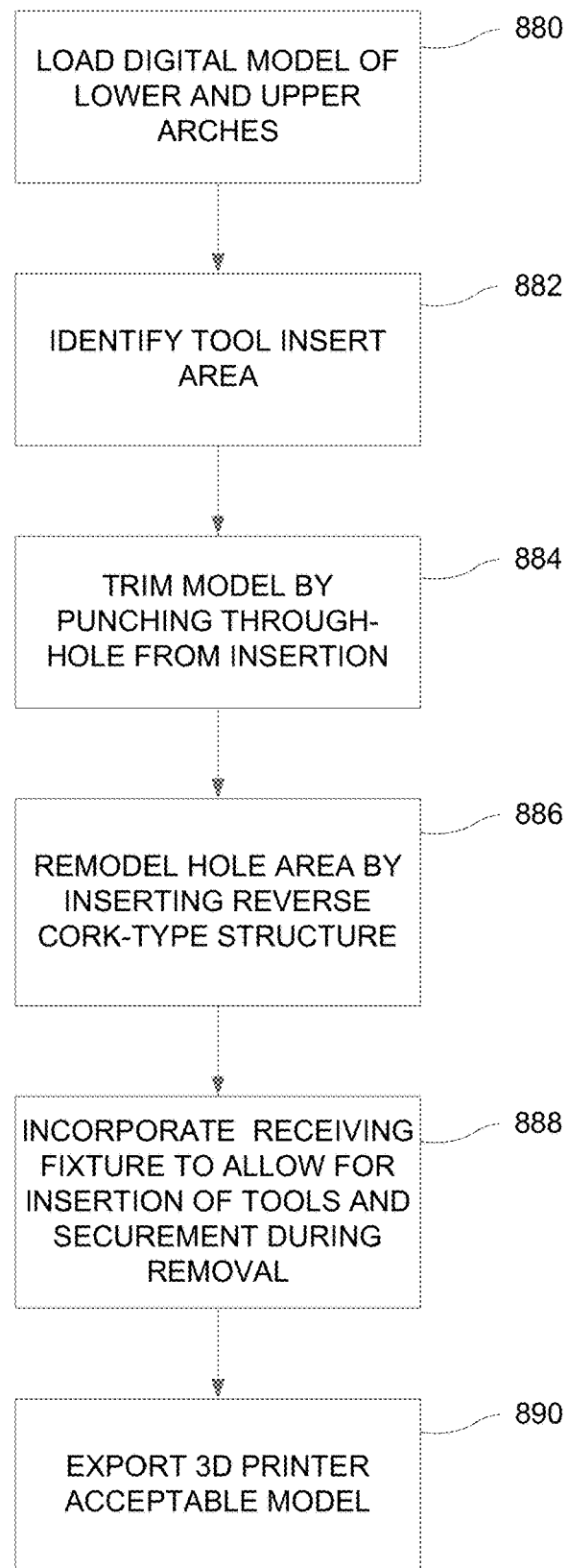
FIG. 37 shows an exemplary process for facilitating removal of the oral appliance via the wedged removal member.

FIG. 37 illustrates a flow diagram for removing the oral appliance fabricated upon a mold using the tapered structure 864, as described above. As previously described, the digital model of the lower and upper arches may be loaded into the computer system 880. The system may then identify an appropriate area along the model for tool insertion 882. Such an area may be located away from the dentition model and so as not to interfere with the fabrication of the oral appliance upon the mold. The system may trim the model by defining a through-hole from insertion 884 and to strengthen the through-hole, the system may then remodel the hole area by forming or inserting the tapered structure 864 (e.g., reverse cork-type structure) 886. The model may incorporate a receiving fixture to allow for the insertion of tools and/or allows for the securement of the mold during removal 888 of the oral appliance from the mold. Once the model has been completed, a 3D printer acceptable model may be exported 890.

The system or method described herein may be deployed in part or in whole through a computer system or machine having one or more processors that execute software programs with the methods as described herein. The software programs may be executed on computer systems such as a server, domain server, Internet server, intranet server, and other variants such as secondary server, host server, distributed server, or other such computer or networking hardware on a processor. The processor may be a part of a server, client, network infrastructure, mobile computing platform, stationary computing platform, or other computing platform. The processor may be any kind of computational or processing device capable of executing program instructions, codes, binary instructions or the like that may directly or indirectly facilitate execution of program code or program instructions stored thereon. In addition, other devices required for execution of methods as described in this application may be considered as a part of the infrastructure associated with the computer system or server.

The system or method described herein may be deployed in part or in whole through network infrastructures. The network infrastructure may include elements such as computing devices, servers, routers, hubs, firewalls, clients, wireless communication devices, personal computers, communication devices, routing devices, and other active and passive devices, modules or components as known in the art. The computing or non-computing device(s) associated with the network infrastructure may include, apart from other components, a storage medium such as flash memory, buffer, stack, RAM, ROM, or the like. The processes, methods, program codes, and instructions described herein and elsewhere may be executed by the one or more network infrastructural elements.

The elements described and depicted herein, including flow charts, sequence diagrams, and other diagrams throughout the figures, imply logical boundaries between the elements. However, according to software or hardware engineering practices, the depicted elements and the functions thereof may be implemented on machines through the computer executable media having a processor capable of executing program instructions stored thereon and all such implementations may be within the scope of this document. Thus, while the foregoing drawings and descriptions set forth functional aspects of the disclosed methods, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this document. As such, the depiction or description of an order for various steps should not be understood to require a particular order of execution for those steps, unless required by a particular application, or explicitly stated or otherwise clear from the context.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device, or other hardware. All such permutations and combinations are intended to fall within the scope of the present disclosure.

The applications of the devices and methods discussed above are not limited to the dental applications but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for developing a treatment plan via a processor for correcting one or more malocclusions in a subject, comprising:
   receiving a scanned dental model of a subject's dentition;
   determining a treatment plan having a plurality of incremental movements for repositioning one or more teeth of the subject's dentition, wherein one or more three-dimensional spheres of influence each having a pre-defined diameter is assigned to a model of each of the one or more teeth to define a safety envelope and to set a proximity distance between each tooth model as the tooth models move along a tooth movement path;
   displaying the tooth movement path of each tooth model; and
   fabricating one or more aligners correlating to a first subset of the plurality of incremental movements.

2. The method of claim 1 further comprising reassessing the subject's dentition after a predetermined period of time to monitor the repositioning of the one or more teeth.

3. The method of claim 1 further comprising fabricating one or more additional aligners correlating to a second subset of the plurality of incremental movements.

4. The method of claim 1 further comprising treating the one or more teeth via a non-aligner corrective measure.

5. The method of claim 1 wherein receiving a scanned dental model comprises receiving a digital image of the subject's dentition.

6. The method of claim 1 wherein determining a treatment plan further comprises:
   applying a label to one or more teeth within the dental model;
   simulating a rolling ball process along an exterior of the one or more teeth and gums within the dental model;
   determining a boundary between each of the one or more teeth and gums based on a path or trajectory of the rolling ball process;
   assigning a hard or soft region to each of the one or more teeth and gums within the dental model; and
   moving a position of the one or more teeth within the dental model to correct for malocclusions in developing a treatment plan.

7. The method of claim 6 wherein simulating a rolling ball process comprises detecting for changes in a path of the rolling ball.

8. The method of claim 6 wherein determining a boundary comprises determining a boundary between adjacent teeth based on a projected trajectory of the rolling ball between the teeth.

9. The method of claim 1 wherein determining a treatment plan further comprises:
   determining a movement for a plurality of digital tooth models in the dental model for correcting the malocclusions via a tooth movement manager module;
   assigning the spheres of influence on each of the tooth models via a collision manager module;
   monitoring an actual state of each tooth of the subject;
   comparing the actual state of each tooth against an expected state of each tooth model via a tooth manager module; and
   adjusting the movement of one or more teeth based on a comparison of the actual state and the expected state if a deviation is detected.

10. The method of claim 9 wherein determining a movement comprises independently executing a tooth movement plan for each of the tooth models.

11. The method of claim 9 wherein assigning a sphere of influence further comprises monitoring for a collision between tooth models.

12. The method of claim 11 further comprising communicating a collision warning to an adjacent tooth model such that one or more of the tooth models alter their movement to avoid the collision.

13. The method of claim 1 wherein fabricating one or more aligners further comprises:
   fabricating a support structure which corresponds to an outer surface of the dentition;
   forming one or more oral appliances upon an exterior surface of the support structure such that an interior of the one or more oral appliances conform to the dentition; and
   removing the support structure from the interior of the one or more oral appliances.

14. The method of claim 13 wherein forming one or more oral appliances comprises forming one or more dental attachments upon the oral appliances.

15. The method of claim 1 wherein fabricating one or more aligners further comprises:
   calculating a rule-based cutting loop path on the model for determining a path for trimming a mold replicating the patient's dentition;
   applying a drape wall from the cutting loop on the model to reduce a complexity of the model;
   determining a position of a cutting instrument relative to the mold for trimming the mold;
   generating a computer numerical control code based on the drape wall and position of the cutting instrument; and
   fabricating the mold based on the generated computer numerical control code.

16. The method of claim 15 wherein calculating a rule-based cutting loop path comprises identifying a first location and a second location opposite to the first location on the model at corresponding interface regions and extending a trim line between the first location and second location.

17. The method of claim 16 wherein applying a drape wall comprises identifying the trim line and replacing a volume below the trim line with a base region.

18. The method of claim 15 wherein applying a drape wall comprises limiting a height of the drape wall to avoid stretching an oral appliance formed upon the mold.

19. The method of claim 15 wherein fabricating the mold comprises securing the mold to a platform.

20. The method of claim 1 further comprising generating one or more manufacturing files based on the treatment plan.

21. The method of claim 20 further comprising transmitting the one or more manufacturing files to a location remote from the subject.

22. The method of claim 1 wherein displaying the tooth movement path further comprises receiving an input from the subject with respect to the treatment plan.

* * * * *